United States Patent
Uchida et al.

(12)

(10) Patent No.: US 6,277,994 B1
(45) Date of Patent: Aug. 21, 2001

(54) COLOR-DEVELOPING AGENT, SILVER HALIDE PHOTOGRAPHIC LIGHT-SENSITIVE MATERIAL AND IMAGE-FORMING METHOD

(75) Inventors: Osamu Uchida; Yasuhiro Ishiwata; Kiyoshi Takeuchi; Taiji Katsumata; Takashi Nakamura, all of Minami-ashigara (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 0 days.

(21) Appl. No.: 09/540,745

(22) Filed: Mar. 31, 2000

(30) Foreign Application Priority Data

| Mar. 31, 1999 | (JP) | 11-090618 |
| Mar. 31, 1999 | (JP) | 11-090669 |
| Mar. 31, 1999 | (JP) | 11-090734 |

(51) Int. Cl.$^7$ ............... C07D 285/05; C07D 284/14; C07D 513/00; C07D 417/00; G03C 7/413
(52) U.S. Cl. ............... 548/130; 548/128; 430/203; 430/218; 430/264; 430/380; 430/440; 430/483
(58) Field of Search ............... 548/128, 130; 430/380, 218, 264, 203, 440, 483

(56) References Cited

U.S. PATENT DOCUMENTS

| 5,851,749 | * | 12/1998 | Okawa et al. | 430/264 |
| 5,871,880 | * | 2/1999 | Makota et al. | 430/226 |
| 5,874,203 | | 2/1999 | Morita et al. | 430/380 |
| 5,976,756 | | 11/1999 | Nakamura et al. | 430/380 |

FOREIGN PATENT DOCUMENTS 9-152702   6/1997 (JP) .

* cited by examiner

Primary Examiner—Richard L. Schilling
(74) Attorney, Agent, or Firm—Burns, Doane, Swecker & Mathis, LLP

(57) ABSTRACT

There is disclosed a novel color-developing agent of a 1,2,4-thiadiazol-5-yl hydrazine type. There is also disclosed a silver halide photographic light-sensitive material which gives sufficient color formation by development and forms an image excellent in image quality and image storability, by using the color-developing agent. Further, there is disclosed an image-forming method using the light-sensitive material.

4 Claims, No Drawings

COLOR-DEVELOPING AGENT, SILVER HALIDE PHOTOGRAPHIC LIGHT-SENSITIVE MATERIAL AND IMAGE-FORMING METHOD

This application claims priority under 35 U.S.C. §§119 and/or 365 to Japanese Patent Application No's 11-90618, 11-90669 and 11-90734 filed in Japan on Mar. 31, 1999.

FIELD OF THE INVENTION

The present invention relates to a novel color-developing agent, a silver halide photographic light-sensitive material and image-forming method using the color-developing agent. Particularly, the present invention relates to a silver halide photographic light-sensitive material which is excellent in color-forming property in the developing stage and in storability of an image, and to an image-forming method utilizing the light-sensitive material.

Furhter, the present invention relates to a color diffusion transfer type silver halide photographic light-sensitive material comprising a novel diffusible dye-forming color-developing agent and a coupler, and to an image-forming method using the light-sensitive material. Particularly, the present invention relates to a color diffusion transfer type silver halide photographic light-sensitive material excellent in storability and sharpness of an image, and to an image-forming method using the light-sensitive material.

BACKGROUND OF THE INVENTION

In a color photographic light-sensitive material, when it is exposed and thereafter color-developed, the oxidized color-developing agent is reacted with a coupler to form an image.

The color-developing is attained, for instance, by dipping an exposed light-sensitive material in an aqueous alkali solution (a developing solution) in which a color-developing agent is dissolved. This technique have many problems, for example, a problem that the developing solution tends to be deteriorated with the lapse of time and problems concerning treatments of developing solution wastes.

As one effective measure to solve above problems, a method wherein an aromatic primary amine developing agent or its precursor is built in the hydrophilic colloid layer of a light-sensitive material is proposed. Further, a method wherein a sulfonylhydrazine-type developing agent is built in the hydrophilic colloid layer of a light-sensitive material is proposed. Examples of these include methods described, for example, in U.S. Pat. No. 803 783, JP-B-58-14671 ("JP-B" means examined Japanese patent publication), European Patent Nos. 545 491(A1) and 565 165(A1).

However, even these methods cannot attain satisfactory color formation when color-developed; and there is the problem of storage stability.

In the fields of silver halide photographic light-sensitive materials, a so-called color diffusion transfer method in which a diffusible dye is formed imagewise on a light-sensitive material and the image is transferred and fixed to an image-receiving material, to form a color image, is known technique, and many proposals concerned this have been made. Adopted in these methods is a method in which a diffusible dye is generally formed, as a function of developing of silver halide, from a compound (hereinafter called a colorant) produced by modifying a pre-colored image-forming dye (pre-formed dye) to one which is resistant to diffusion. In the method like this, when the colorant is added to the same layer as a silver halide emulsion, an unacceptable reduction in sensitivity to exposure is caused by a filter effect of a dye portion. Hence, generally, in order not to face the problem, a method is adopted in which an image-forming colorant is added to a layer more apart from the exposed surface with respect to the silver halide emulsion layer. In this method, although the above reduction in sensitivity which is caused by the filter effect is avoided, there is an inherent drawback that developing information is transferred from the silver halide emulsion to the colorant inefficiently because the physical distance between the silver halide emulsion and the colorant is large.

In order to improve these drawbacks, a so-called coupling system is proposed in U.S. Pat. No. 4,469,773 and JP-B-63-36487 in which system a dye is formed by a coupling reaction between an oxidized product of a developing agent, which is produced as a function of the developing of silver halide, and a coupler. However, the color-developing agent described therein has a difficulty in the compatibility of the storage stability and the activity of the coupling reaction and a difficulty in modifying both the color-developing agent and the coupler to those having resistance to diffusion.

Novel color-developing agents are proposed in JP-A-09-152702 ("JP-A" means unexamined published Japanese patent application) and JP-A-09-152705. In these methods, however, sufficient color-forming property is not obtained yet. Also, whether or not there are problems concerning the hue and color image stability of a dye to be formed, or the color image stability of a dye to be formed is not mentioned in those publications at all.

Particularly, the compounds described in the said JP-A-9-152705 have the drawbacks that sharpness of a magenta dye to be formed is insufficient and the storage stability of a color image is also insufficient.

In JP-A-9-152702, there is a proposal concerning a heterocyclic hydrazine developing agent having two or more nitrogen atoms. However, in this publication, there is no specific description concerning diffusion transfer type silver halide photographic light-sensitive materials and there is also nothing referring to specific properties (e.g., hue and stability) of a dye to be formed.

SUMMARY OF THE INVENTION

It is an object of the present invention to provide a novel color-developing agent. It is another object of the present invention to provide a silver halide photographic light-sensitive material which gives sufficient color formation by development and forms an image excellent in image quality and image storability, by using the color-developing agent. Still another object of the present invention is to provide an image-forming method using the light-sensitive material.

Further another object of the present invention is to provide a method for forming a diffusible magenta dye from a colorless color-developing agent and a colorless coupler, in which the magenta dye to be formed in this method is excellent in sharpness and storage stability. Still another object of the present invention is to provide a color diffusion transfer type silver halide photographic light-sensitive material which makes it possible to obtain sufficient color formation upon development and to form a color transfer image of excellent image quality. Another object of the present invention is to provide an image-forming method using the light-sensitive material.

Other and further objects, features, and advantages of the invention will appear more fully from the following description.

DETAILED DESCRIPTION OF THE INVENTION

The present inventors found that the above objects of the present invention can be attained by the following means.

(1) A color-developing agent represented by the following formula (1):

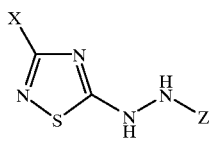

formula (1)

wherein X represents a substituent that has, as a substituent on the substituent, at least one substituent represented by —COOH, —NHSO$_2$R, —SO$_2$NHR, —SO$_2$NHCOR, —CONHSO$_2$R, —OH or —SH, in which R represents an alkyl group, an aryl group or an aromatic heterocyclic group, each of which may be substituted, and Z represents a carbamoyl group, an acyl group, an alkoxycarbonyl group or an aryloxycarbonyl group.

(2) The color-developing agent according to the above (1), wherein Z in the formula (1) is a carbamoyl group, which is a carbamoyl group having one or more hydrogen atoms bonded on the nitrogen atom of the carbamoyl group.

(3) A silver halide photographic light-sensitive material containing at least one color-developing agent represented by formula (1) stated in the above (1), in at least one hydrophilic colloid layer provided on a support.

(4) An image forming method, comprising subjecting the silver halide photographic light-sensitive material according to the above (3), to imagewise exposure, and subjecting the resultant light-sensitive material to development.

(5) The image forming method as stated in the above (4), wherein the development step comprises subjecting the silver halide photographic light-sensitive material to heat development.

(6) The image forming method as stated in the above (4), wherein the development step comprises subjecting the silver halide photographic light-sensitive material to development, in the presence of an alkali generated from a metal salt which is sparingly soluble in water and a complexing agent of the metal salt.

(7) The image forming method as stated in the above (4), wherein the development step comprises subjecting the color diffusion transfer type silver halide photographic light-sensitive material to development with an alkali processing solution.

(8) A color-developing agent represented by the following formula (2):

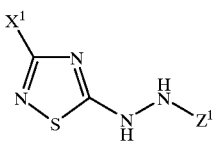

formula (2)

wherein $X^1$ represents a halogen atom, an alkylthio group, an alkylsulfinyl group, an alkylsulfonyl group, an arylthio group, an arylsulfinyl group, an arylsulfonyl group or a sulfamoyl group, provided that a further substituent which can be substituted on $X^1$ excludes a hydroxy group, a carboxyl group, a mercapto group, an aminosulfonyl group, a carbonylaminosulfonyl group, a sulfonylamino group and a sulfonylaminocarbonyl group, $Z^1$ represents a carbamoyl group, an acyl group, an alkoxycarbonyl group or an aryloxycarbonyl group.

(9) The color-developing agent according to the above (8), wherein $Z^1$ in the formula (2) is a carbamoyl group, which is a carbamoyl group having one or more hydrogen atoms bonded on the nitrogen atom of the carbamoyl group.

(10) A silver halide photographic light-sensitive material containing at least one color-developing agent represented by formula (2) stated in the above (8), in at least one hydrophilic colloid layer provided on a support.

(11) An image forming method, comprising subjecting the silver halide photographic light-sensitive material according to the above (10), to imagewise exposure, and subjecting the resultant light-sensitive material to development.

(12) The image forming method as stated in the above (11), wherein the development step comprises subjecting the silver halide photographic light-sensitive material to heat development.

(13) The image forming method as stated in the above (11), wherein the development step comprises subjecting the silver halide photographic light-sensitive material to development, in the presence of an alkali generated from a metal salt which is sparingly soluble in water and a complexing agent of the metal salt.

(14) The image forming method as stated in the above (11), wherein the development step comprises subjecting the color diffusion transfer type silver halide photographic light-sensitive material to development with an alkali processing solution.

(15) A color diffusion transfer type silver halide photographic light-sensitive material comprising at least one color-developing agent represented by the following formula (3) and at least one coupler represented by the following formula (4), in at least one hydrophilic colloid layer provided on a support:

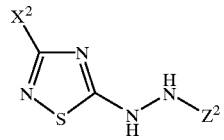

formula (3)

wherein $X^2$ represents an alkyl group or an aryl group, and $Z^2$ represents a carbamoyl group, an acyl group, an alkoxycarbonyl group or an aryloxycarbonyl group:

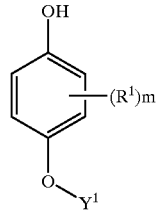

formula (4)

wherein $R^1$ represents a substituent, m is an integer from 0 to 4, in which when m is 2 or more, $R^1$s may be the same or different and may form a five- to seven-membered ring between them, $Y^1$ represents an aryl group, an unsaturated heterocyclic group, an acyl group, an alkoxycarbonyl group, an aryloxycarbonyl group, a carbamoyl group or a sulfonyl group, in which the groups each have an alkyl group and the sum of carbon atoms thereof are 6 or more in total.

(16) The color diffusion transfer type silver halide photographic light-sensitive material according to the above (15), wherein $Z^2$ in the formula (3) is a carbamoyl group, which is a carbamoyl group having one or more hydrogen atoms bonded on the nitrogen atom of the carbamoyl group.

(17) The color diffusion transfer type silver halide photographic light-sensitive material according to the above (15), wherein $Y^1$ in the formula (4) is an alkoxycarbonyl group or a carbamoyl group, in which the groups each have an alkyl group and the sum of carbon atoms thereof are 6 or more in total.

(18) An image forming method, comprising subjecting the color diffusion transfer type silver halide photographic light-sensitive material according to the above (15), (16) or (17), to imagewise exposure, and subjecting the resultant light-sensitive material to development.

(19) The image forming method as stated in the above (18), wherein the development step comprises subjecting the color diffusion transfer type silver halide photographic light-sensitive material to heat development.

(20) The image forming method as stated in the above (18), wherein the development step comprises subjecting the color diffusion transfer type silver halide photographic light-sensitive material to development, in the presence of an alkali generated from a metal salt which is sparingly soluble in water and a complexing agent of the metal salt.

(21) The image forming method as stated in the above (18), wherein the development step comprises subjecting the color diffusion transfer type silver halide photographic light-sensitive material to development with an alkali processing solution.

Herein, the color-developing agents as stated in the above (1) and (2), the silver halide photographic light-sensitive material as stated in the above (3), and the image-forming methods as stated in the above (4) to (7) are referred to as the first embodiment of the present invention.

Further, the color-developing agents as stated in the above (8) and (9), the silver halide photographic light-sensitive material as stated in the above (10), and the image-forming methods as stated in the above (11) to (14) are referred to as the second embodiment of the present invention.

In addition, the color diffusion transfer type silver halide photographic light-sensitive materials as stated in the above (15) to (17), and the image-forming methods as stated in the above (18) to (21) are referred to as the third embodiment of the present invention.

In the following description, the present invention means to include all of the above first, second, and third embodiments, unless otherwise specified.

Herein, in the present specification and claims, a group on a compound includes both a group having a substituent thereon and a group having no substituent (i.e. an unsubstituted group), unless otherwise specified.

The compound represented by the formula (1), which is used in the first embodiment of the present invention will be explained in detail below.

Examples of the substituent represented by X in the formula (1) include an alkyl group (e.g., a methyl group, ethyl group and benzyl group), an aryl group (e.g., a phenyl group, naphthyl group and m-nitrophenyl group), an alkylthio group (e.g., a methylthio group, ethylthio group and benzylthio group), an alkylsulfinyl group (e.g., a methanesulfinyl group and ethanesulfinyl group), an alkylsulfonyl group (e.g., a methanesulfonyl group, ethanesulfonyl group and benzylsulfonyl group), an arylthio group (e.g., a phenylthio group, naphthylthio group and 4-methoxyphenylthio group), an arylsulfinyl group (e.g., benzenesulfinyl group and naphthalenesulfinyl group), an arylsulfonyl group (e.g., benzenesulfonyl groups, p-toluenesulfonyl group and p-methanesulfonylbenzenesulfonyl group) and a sulfamoyl group (e.g., an N-butylsulfamoyl group and N,N-diethylsulfamoyl group). Preferably each of these groups has 1 to 50 carbon atoms and more preferably 1 to 20 carbon atoms. Further these groups respectively have at least one substituent represented by —COOH, —NHSO$_2$R, —SO$_2$NHR, —SO$_2$NHCOR, —CONHSO$_2$R, —OH or —SH, in which R represents an alkyl group, an aryl group or an aromatic heterocyclic group.

Among these groups, the substituent represented by X is preferably an alkyl group, aryl group, alkylthio group, alkylsulfonyl group, arylthio group or arylsulfonyl group.

The substituent that X has is preferably —NHSO$_2$R, —SO$_2$NHR, —SO$_2$NHCOR, —CONHSO$_2$R or —OH, and more preferably —NHSO$_2$R or —SO$_2$NHR, in which R represents an alkyl group (e.g., a methyl group, ethyl group or benzyl group), an aryl group (e.g., a phenyl group, naphthyl group or m-nitrophenyl group) or an aromatic heterocyclic group (e.g., a 2-pyridyl group, 4-pyridyl group or 2-furyl group), and preferably an alkyl group or aryl group.

Z represents a carbamoyl group, acyl group, alkoxycarbonyl group or aryloxycarbonyl group. Among these groups, a carbamoyl group is preferable and a carbamoyl group having one or two hydrogen atom(s), and more preferably one hydrogen atom bonded on the nitrogen atom is particularly preferable.

As the carbamoyl group, those having 1–50 carbon atoms are preferable and those having 8–40 carbon atoms are more preferable. Specific examples of the carbamoyl group include a hexadecylcarbamoyl group, octadecylcarbamoyl group, 3-(2,4-di-tert-pentylphenoxy)propylcarbamoyl group, 4-dodecyloxyphenylcarbamoyl group, 2-chloro-5-dodecyloxycarbonylphenylcarbamoyl group and naphthylcarbamoyl group.

The aforementioned groups each may further have a substituent, and examples of the further substituent include a cyano group, a carboxyl group, a sulfo group, a hydroxy group, a nitro group, a mercapto group, a halogen atom (a fluorine atom, chlorine atom, bromine atom and iodine atom), an alkyl group (an alkyl group which has generally 30 or less carbon atoms and preferably 8 or less carbon atoms and may be substituted, for example, a methyl group, trifluoromethyl group, benzyl group, dimethylaminomethyl group, ethoxycarbonylmethyl group, acetylaminomethyl group, ethyl group, carboxyethyl group, allyl group, n-propyl group, iso-propyl group, n-butyl group, t-butyl group, t-pentyl group, cyclopentyl group, n-hexyl group, t-hexyl group, cyclohexyl group, t-octyl group, n-decyl group, n-undecyl group and n-dodecyl group), an aryl group (an aryl group which has generally 30 or less carbon atoms and preferably 10 or less carbon atoms and may be substituted, for example, a phenyl group, naphthyl group, 3-hydroxyphenyl group, 3-chlorophenyl group, 4-acetylaminophenyl group, 2-methanesulfonylphenyl group, 4-methoxyphenyl group, 4-methanesulfonylphenyl group and 2,4-dimethylphenyl group), a heterocyclic group (a heterocyclic group which has generally 30 or less carbon atoms and preferably 10 or less carbon atoms and may be substituted, for example, a 1-imidazolyl group, 2-furyl group, 2-pyridyl group, 3-pyridyl group, 3,5-dicyano-2-pyridyl group, 5-tetrazolyl group, 5-phenyl-1-tetrazolyl group, 2-benzthiazolyl group, 2-benzimidazolyl group, 2-benzoxazolyl group, 2-oxazoline-2-yl group and morpholino group), an acyl group (an acyl group which has generally 20 or less carbon atoms and preferably 8 or less carbon atoms and may be substituted, for example, an acetyl group, propionyl group, butyroyl group, iso-butyroyl group, 2,2-dimethylpropionyl group, benzoyl group, 3,4- dichlorobenzoyl group, 3-acetylamino-4-methoxybenzoyl group and 4-methylbenzoyl group), a sulfonyl group (a sulfonyl group which has generally 20 or less carbon atoms and preferably 8 or less carbon atoms and may be substituted, for example, a methanesulfonyl group, ethanesulfonyl group, chloromethanesulfonyl group, propanesulfonyl group, butanesulfonyl group, n-octanesulfonyl group, n-dodecanesulfonyl group, benzenesulfonyl group and 4-methylphenylsulfonyl group), an alkoxy group (an alkoxy group which has generally 20 or less carbon atoms and preferably 8 or less carbon atoms and may be substituted, for example, a methoxy group, ethoxy group, n-propyloxy group, iso-propyloxy group and cyclohexylmethoxy group), an aryloxy group or heteroaryloxy group (an aryloxy group or heteroaryloxy group which has generally 20 or less carbon atoms and preferably 10 or less carbon atoms and may be substituted, for example, a phenoxy group, naphthyloxy group, 4-acetylaminophenoxy group, pyrimidine-2-yloxy group and 2-pyridyloxy group), a silyloxy group (a silyloxy group which has generally 10 or less carbon atoms and preferably 8 or less carbon atoms and may be substituted, for example, a trimethylsilyloxy group and tert-butyldimethylsilyloxy group), an alkylthio group (an alkylthio group which has generally 20 or less carbon atoms and preferably 8 or less carbon atoms and may be substituted, for example, a methylthio group, ethylthio group, n-butylthio group, n-octylthio group, t-octylthio group, ethoxycarbonylmethylthio group, benzylthio group and 2-hydroxyethylthio group), an arylthio group or heteroarylthio group (an arylthio or heteroarylthio group which has generally 20 or less carbon atoms and preferably 10 or less carbon atoms and may be substituted, for example, a phenylthio group, 4-chlorophenylthio group, 2-n-butoxy-5-t-octylphenylthio group, 4-nitrophenylthio group, 2-nitrophenylthio group, 4-acetylaminophenylthio group, 1-phenyl-5-tetrazolylthio group, 5-methanesulfonylbenzothiazole-2-yl group), a carbamoyl group (a carbamoyl group which has generally 20 or less carbon atoms and preferably 8 or less carbon atoms and may be substituted, for example, a carbamoyl group, methylcarbamoyl group, dimethylcarbamoyl group, bis-(2-methoxyethyl)carbamoyl group, diethylcarbamoyl group, cyclohexylcarbamoyl group and di-n-octylcarbamoyl group), a sulfamoyl group (a sulfamoyl group which has generally 20 or less carbon atoms and preferably 8 or less carbon atoms and may be substituted, for example, a sulfamoyl group, methylsulfamoyl group, dimethylsulfamoyl group, bis-(2-methoxyethyl)sulfamoyl group, diethylsulfamoyl group, di-n-butylsulfamoyl group, methyl-n-octylsulfamoyl group, 3-ethoxypropylmethylsulfamoyl group and N-phenyl-N-methylsulfamoyl group), an acylamino group (an acylamino group which has generally 20 or less carbon atoms and preferably 8 or less carbon atoms and may be substituted, for example, an acetylamino group, 2-carboxybenzoylamino group, 3-nitrobenzoylamino group, 3-diethylaminopropanoylamino group and acryloylamino group), a sulfonylamino group (a sulfonylamino group which has generally 20 or less carbon atoms and preferably 8 or less carbon atoms and may be substituted, for example, a methanesulfonylamino group, benzenesulfonylamino group and 2-methoxy-5-n-methylbenzenesulfonylamino group), an alkoxycarbonylamino group (an alkoxycarbonylamino group which has generally 20 or less carbon atoms and preferably 8 or less carbon atoms and may be substituted, for example, a methoxycarbonylamino group, ethoxycarbonylamino group, 2-methoxyethoxycarbonylamino group, iso-butoxycarbonylamino group, benzyloxycarbonylamino group, t-butoxycarbonylamino group and 2-cyanoethoxycarbonylamino group), an alkoxycarbonyloxy group (an alkoxycarbonyloxy group which has generally 20 or less carbon atoms and preferably 8 or less carbon atoms and may be substituted, for example, a methoxycarbonyloxy group, ethoxycarbonyloxy group and methoxyethoxycarbonyloxy group), an aryloxycarbonylamino group (an aryloxycarbonylamino group which has generally 20 or less carbon atoms and preferably 8 or less carbon atoms and may be substituted, for example, a phenoxycarbonylamino group, 2,4-nitrophenoxycarbonylamino group and 4-t-butoxyphenoxycarbonylamino group), an aminocarbonylamino group (an aminocarbonylamino group which has generally 20 or less carbon atoms and preferably 8 or less carbon atoms and may be substituted, for example, a methylaminocarbonylamino group, morpholinocarbonylamino group, diethylaminocarbonylamino group, N-ethyl-N-phenylaminocarbonylamino group, 4-cyanophenylaminocarbonylamino group and 4-methanesulfonylaminocarbonylamino group), an aminocarbonyloxy group (an aminocarbonyloxy group which has generally 20 or less carbon atoms and preferably 8 or less carbon atoms and may be substituted, for example, a dimethylaminocarbonyloxy group and pyrrolidinocarbonyloxy group),an aminosulfonylamino group (an aminosulfonylamino group which has generally 20 or less carbon atoms and preferably 8 or less carbon atoms and may be substituted, for example, a diethylaminosulfonylamino group, di-n-butylaminosulfonylamino group and phenylaminosulfonylamino group), an amino group (an amino group which has generally 30 or less carbon atoms and preferably 8 or less carbon atoms and may be substituted, for example, an amino group, methylamino group, dimethylamino group, ethylamino group, ethyl-3-carboxypropylamino group, ethyl-2-sulfoethylamino group, phenylamino group, methylphenylamino group and methyloctylamino group), an alkoxycarbonyl group (an alkoxycarbonyl group which has generally 20 or less carbon atoms and preferably 6 or less carbon atoms and may be substituted, for example, a methoxycarbonyl group, ethoxycarbonyl group and methoxyethoxycarbonyl group), an aryloxycarbonyl group (an aryloxycarbonyl group which has generally 20 or less carbon atoms and preferably 10 or less carbon atoms and may be substituted, for example, a phenoxycarbonyl group and p-methoxyphenoxycarbonyl group), an acyloxy group (an acyloxy group which has generally 20 or less carbon atoms and preferably 8 or less carbon atoms and may be substituted, for example, an acetoxy group, benzoyloxy group, 2-butenoyloxy group and 2-methylpropanoyloxy group), an aryloxycarbonyloxy group (an aryloxycarbonyloxy group which has generally 20 or less carbon atoms and preferably 8 or less carbon atoms and may be substituted, for example, a phenoxycarbonyloxy group, 3-cyanophenoxycarbonyloxy group, 4-acetoxyphenoxycarbonyloxy group and 4-t-butoxycarbonylaminophenoxycarbonyloxy group), and a sulfonyloxy group (a sulfonyloxy group which has generally 20 or less carbon atoms and preferably 8 or less carbon atoms and may be substituted, for example, a phenylsulfonyloxy group, methanesulfonyloxy group, chloromethanesulfonyloxy group, 4-chlorophenylsulfonyloxy group and dodecylsulfonyloxy group).

Next, examples of the color-developing agent represented by the formula (1) will be explained. However, the scope of the present invention is not limited to these exemplified examples.

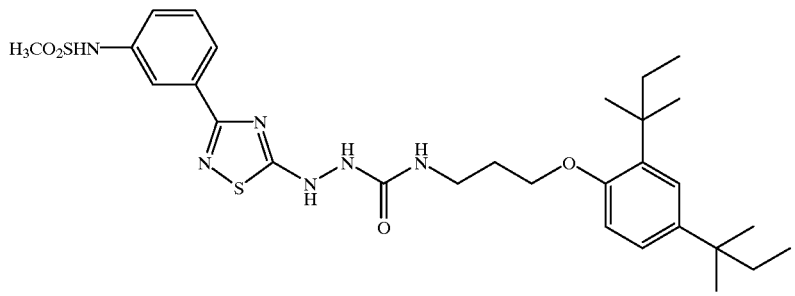
R-1
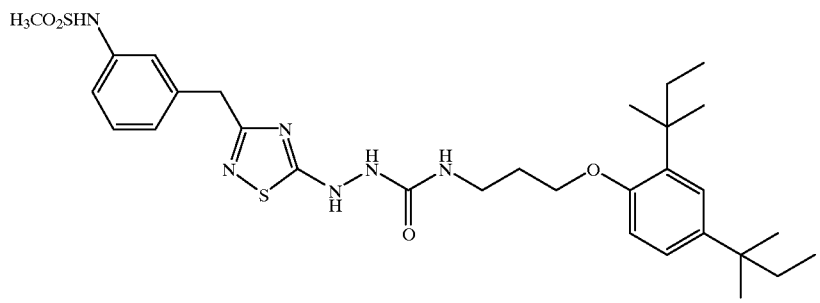
R-2
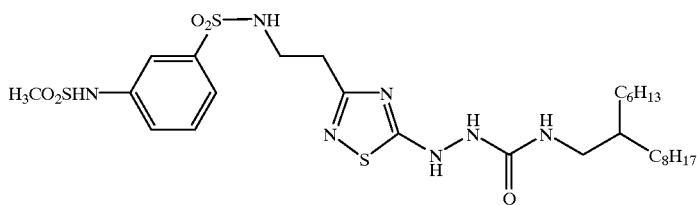
R-3
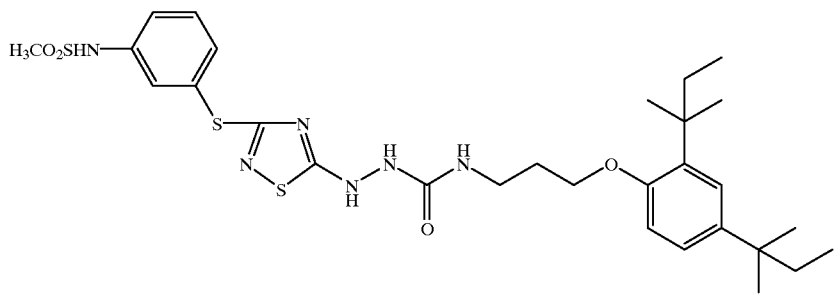
R-4
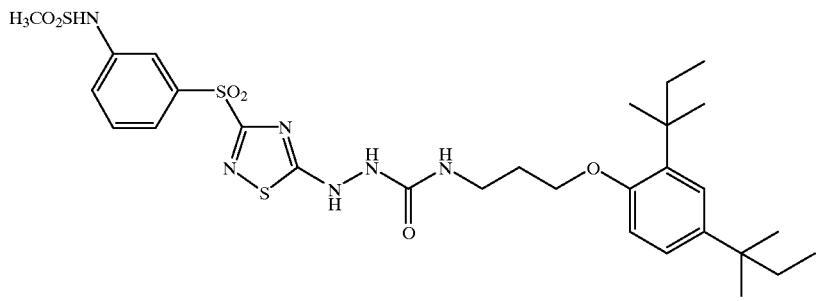
R-5

-continued
R-6
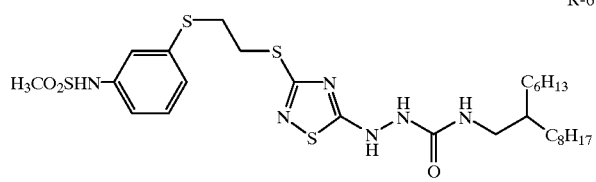
R-7
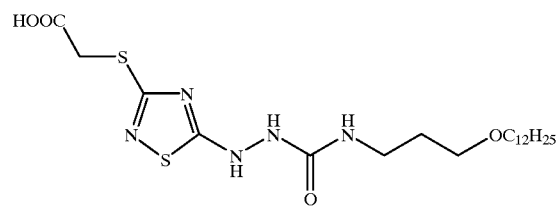
R-8
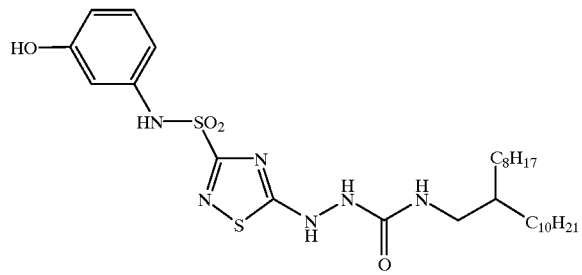
R-9
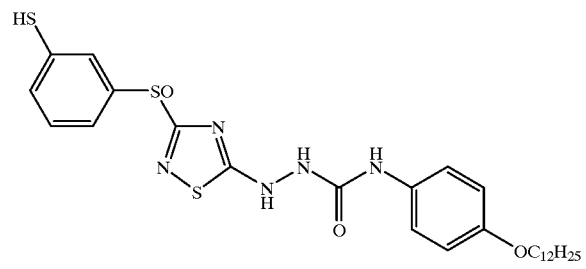
R-10
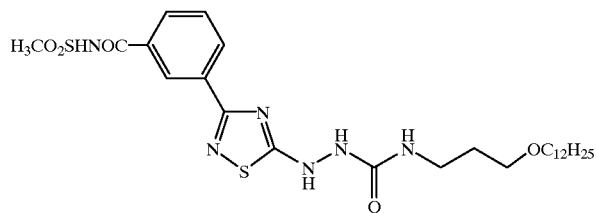
R-11
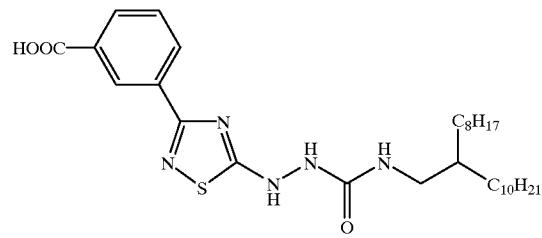
R-12
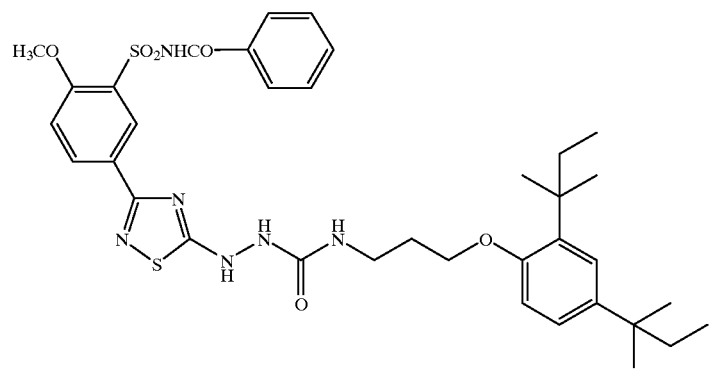
R-13
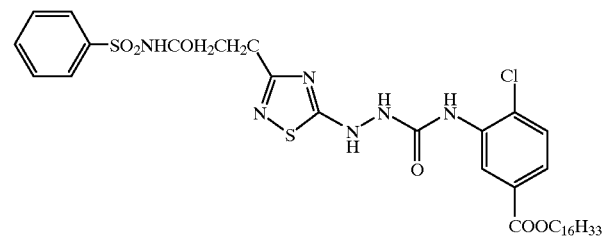
R-14
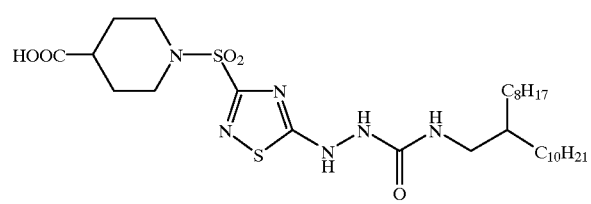

-continued
R-15
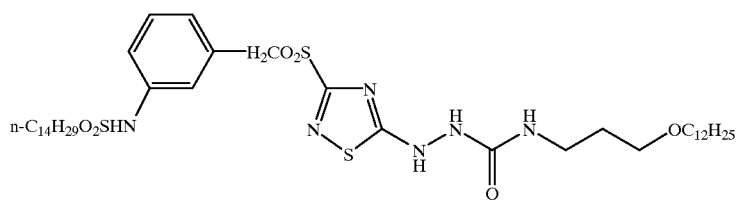
R-16
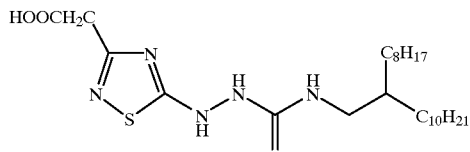
R-17
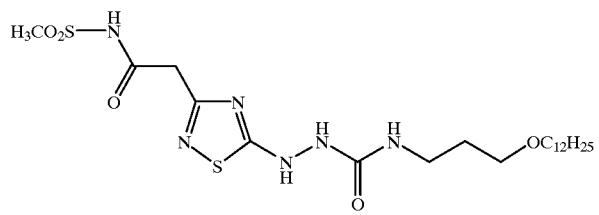
R-18
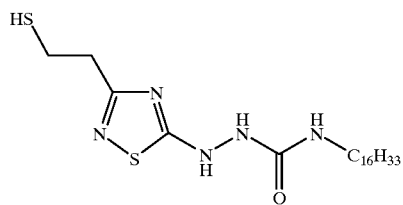
R-19
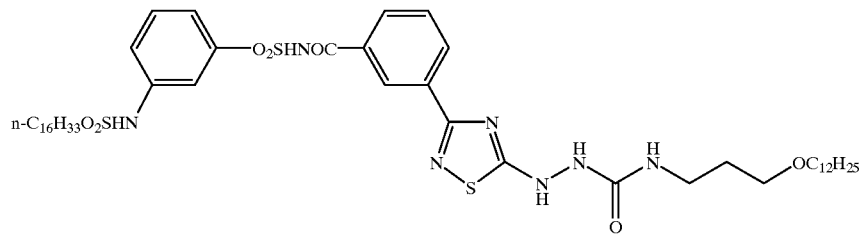
R-20
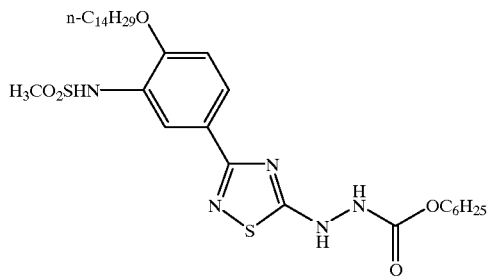
R-21
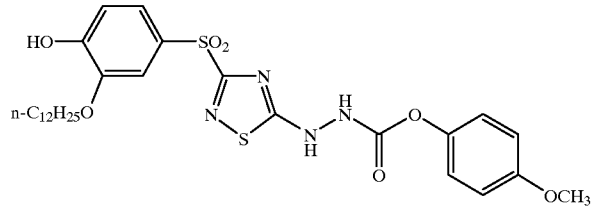
R-22
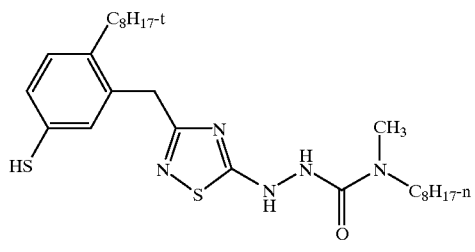
R-23
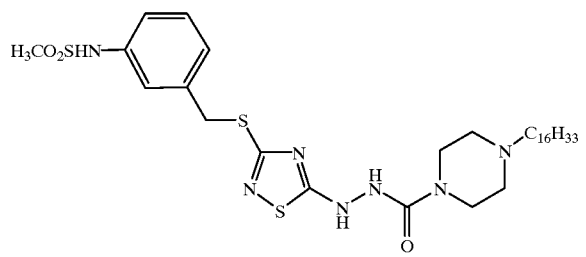

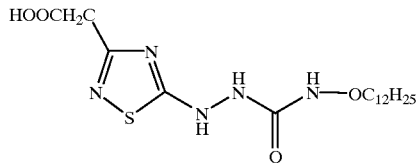

R-24

Next, the compound represented by the formula (2), which is used in the second embodiment of the present invention will be explained in detail.

$X^1$ in the formula (2) represents a halogen atom (e.g., a chlorine atom and bromine atom), an alkylthio group (e.g., a methylthio group, ethylthio group and cyanomethylthio group) which may have a substituent, an alkylsulfinyl group (e.g., a methanesulfinyl group and ethanesulfinyl group) which may have a substituent, an alkylsulfonyl group (e.g., a methanesulfonyl group, ethanesulfonyl group and benzylsulfonyl group) which may have a substituent, an arylthio group (e.g., a phenylthio group, naphthylthio group and 4-methoxyphenylthio group) which may have a substituent, an arylsulfinyl group (e.g., a benzenesulfinyl group and naphthalenesulfinyl group) which may have a substituent, an arylsulfonyl group (e.g., a benzenesulfonyl group, p-toluenesulfonyl group and p-methanesulfonylbenzenesulfonyl group) which may have a substituent, or a sulfamoyl group (e.g., N,N-disubstituted sulfamoyl group, for example, an N,N-diethylsulfamoyl group) which may have a substituent. The number of carbon atoms of each of these groups is preferably 1 to 50 and more preferably 1 to 20.

Among these groups, a halogen atom, an alkylthio group, an alkylsulfonyl group, an arylthio group and an arylsulfonyl group are preferable. These groups may have a substituent.

$Z^1$ represents a carbamoyl group, an acyl group, an alkoxycarbonyl group or an aryloxycarbonyl group. Among these groups, a carbamoyl group is preferable, and a carbamoyl group having one or two and more preferably one hydrogen atom bonded on the nitrogen atom is particularly preferable.

As the carbamoyl group, those having 1–50 carbon atoms are preferable and those having 8–40 carbon atoms are more preferable. Specific examples of the carbamoyl group include a hexadecylcarbamoyl group, octadecylcarbamoyl group, 3-(2,4-di-tert-pentylphenoxy)propylcarbamoyl group, 4-dodecyloxyphenylcarbamoyl group, 2-chloro-5-dodecyloxycarbonylphenylcarbamoyl group and naphthylcarbamoyl group.

As preferable examples of the aforementioned substituents, those mentioned as examples of the substituent that the group on the formula (1) may further have, can be mentioned. However, it is to be noted that a substituent that $X^1$ may have as a further substituent thereon, does not include a hydroxy group, carboxyl group, mercapto group, aminosulfonyl group, carbonylaminosulfonyl group, sulfonylamino group, and sulfonylaminocarbonyl group.

Next, examples of the color-developing agent represented by the formula (2) will be explained. However, the scope of the present invention is not limited to these specific examples.

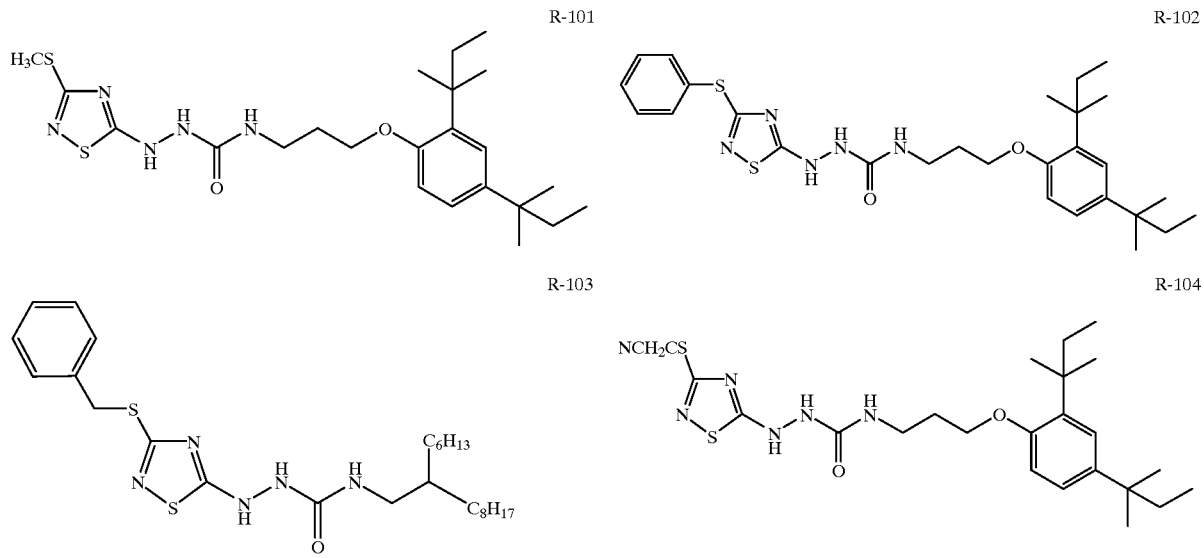

-continued
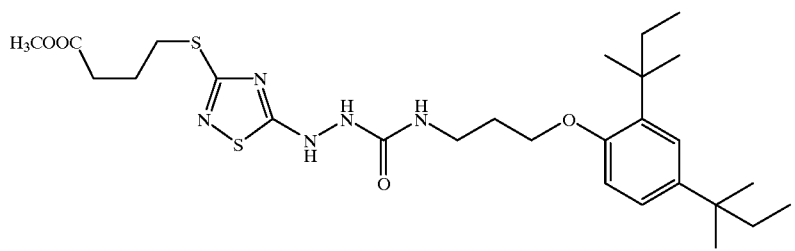
R-105
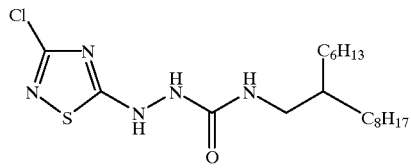
R-106
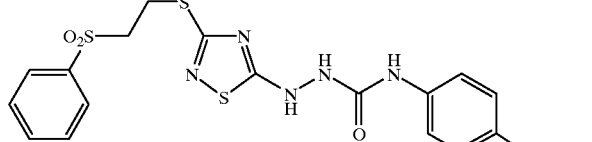
R-107
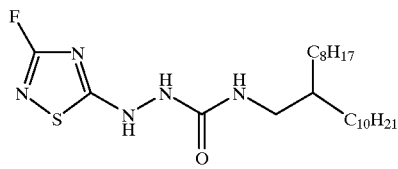
R-108
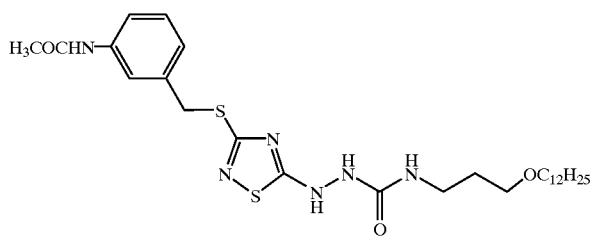
R-110
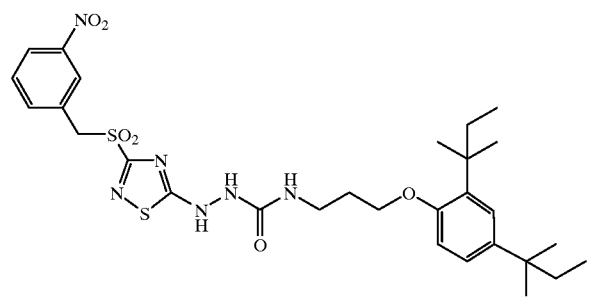
R-112
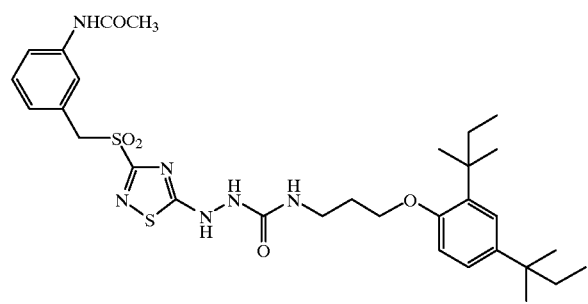
R-114
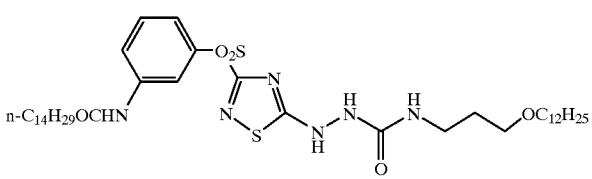
R-115

-continued

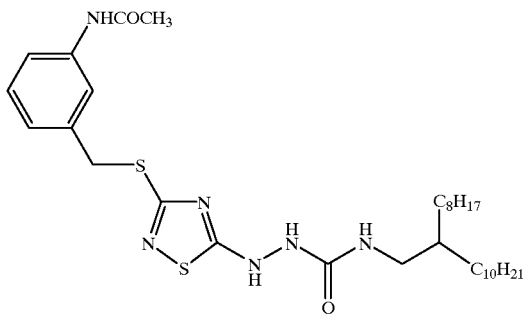
R-116

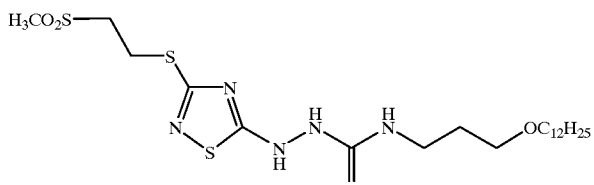
R-117

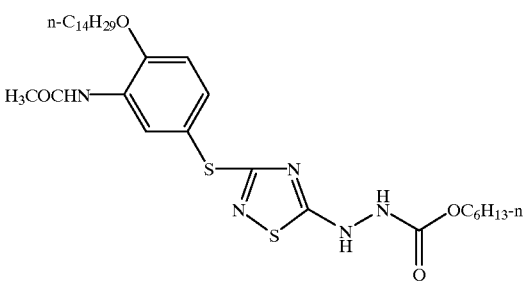
R-118

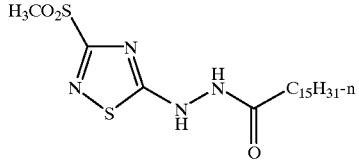
R-119

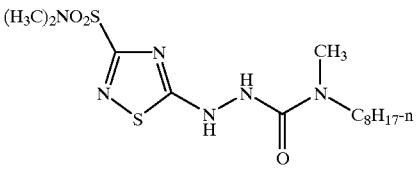
R-120

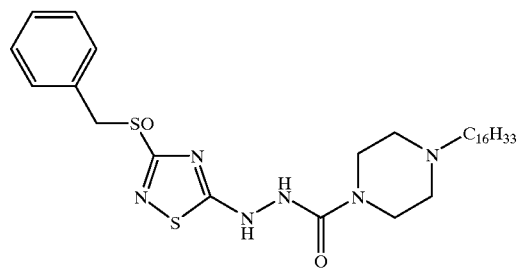
R-121

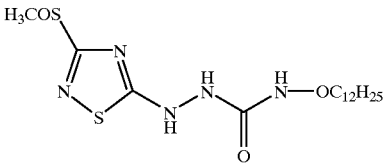
R-122

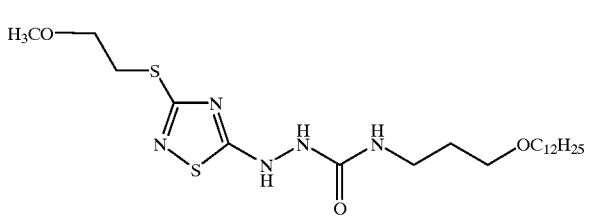
R-123

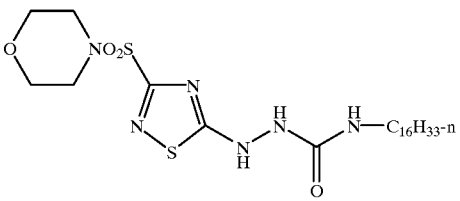
R-124

Next, the compounds represented by the formula (3) or (4) for use in the third embodiment of the present invention will be explained in detail.

$X^2$ in the formula (3) represents preferably an alkyl group having 1 to 8 carbon atoms which may have a substituent (e.g., a methyl group, ethyl group, trifluoromethyl group, trichloromethyl group or cyanomethyl group), or an aryl group having 6 to 15 carbon atoms which may have a substituent (e.g., a phenyl group, naphthyl group or m-nitrophenyl group).

$Z^2$ represents a carbamoyl group, acyl group, alkoxycarbonyl group or aryloxycarbonyl group. Among these groups, a carbamoyl group is preferable and a carbamoyl group having one or two and preferably one hydrogen atom bonded on the nitrogen atom is particularly preferable.

As the carbamoyl group, those having 1–50 carbon atoms are preferable and those having 8–40 carbon atoms are more preferable. Specific examples of the carbamoyl group include a hexadecylcarbamoyl group, octadecylcarbamoyl group, 3-(2,4-di-tert-pentylphenoxy)propylcarbamoyl group, 4-dodecyloxyphenylcarbamoyl group, 2-chloro-5-dodecyloxycarbonylphenylcarbamoyl group and naphthylcarbamoyl group.

In formula (4), $R^1$ represents a substituent. Examples of the substituent include a straight-chain or branched, chain or cyclic alkyl group having 1 to 8 carbon atoms (e.g. trifluoromethyl, methyl, ethyl, propyl, heptafluoropropyl, isopropyl, butyl, t-butyl, t-pentyl, cyclopentyl, cyclohexyl, octyl, and 2-ethylhexyl); a straight-chain or branched, chain or cyclic alkenyl group having 2 to 8 carbon atoms (e.g. vinyl, 1-methylvinyl, and cyclohexen-1-yl); an alkynyl group having 2 to 8 carbon atoms in all (e.g. ethynyl and 1-propinyl), an aryl group having 6 to 15 carbon atoms (e.g. phenyl, and naphthyl), an acyloxy group having 1 to 8 carbon atoms (e.g. acetoxy and benzoyloxy), a carbamoyloxy group having 1 to 8 carbon atoms (e.g. N,N-dimethylcarbamoyloxy), a carbonamido group having 1 to 8 carbon atoms (e.g. formamido, N-methylacetamido, acetamido, N-methylformamido, and benzamido), a sulfonamido group having 1 to 8 carbon atoms (e.g. methanesulfonamido, benzenesulfonamido, and p-toluenesulfonamido), a carbamoyl group having 1 to 8 carbon atoms (e.g. N-methylcarbamoyl, N,N-diethylcarbamoyl, and N-mesylcarbamoyl), a sulfamoyl group having 0 to 8 carbon atoms (e.g. N-butylsulfamoyl, N,N-diethylsulfamoyl, and N-methyl-N-(4-methoxyphenyl)sulfamoyl), an alkoxy group having 1 to 8 carbon atoms (e.g. methoxy, propoxy, isopropoxy, octyloxy, and t-octyloxy), an aryloxy group having 6 to 15 carbon atoms (e.g. phenoxy, 4-methoxyphenoxy, and naphthoxy), an aryloxycarbonyl group having 7 to 15 carbon atoms (e.g. phenoxycarbonyl and naphthoxycarbonyl), an alkoxycarbonyl group having 2 to 10 carbon atoms (e.g. methoxycarbonyl and t-butoxycarbonyl), an N-acylsulfamoyl group having 1 to 8 carbon atoms (e.g. N-propanoylsulfamoyl and N-benzoylsulfamoyl), an alkylsulfonyl group having 1 to 8 carbon atoms (e.g. methanesulfonyl, octylsulfonyl, and 2-methoxyethylsulfonyl), an arylsulfonyl group having 6 to 15 carbon atoms (e.g. benzenesulfonyl, and p-toluenesulfonyl), an alkoxycarbonylamino group having 2 to 8 carbon atoms (e.g. ethoxycarbonylamino), an aryloxycarbonylamino group having 7 to 15 carbon atoms (e.g. phenoxycarbonylamino and naphthoxycarbonylamino), an amino group having 0 to 8 carbon atoms (e.g. amino, methylamino, diethylamino, diisopropylamino, anilino, and morpholino), a cyano group, a nitro group, a carboxyl group, a hydroxyl group, a sulfo group, a mercapto group, an alkylsulfinyl group having 1 to 8 carbon atoms (e.g. methanesulfinyl and octanesulfinyl), an arylsulfinyl having 6 to 15 carbon atoms (e.g. benzenesulfinyl, 4-chlorophenylsulfinyl, and p-toluenesulfinyl), an alkylthio group having 1 to 8 carbon atoms (e.g. methylthio, octylthio, and cyclohexylthio), an arylthio group having 6 to 15 carbon atoms (e.g. phenylthio and naphthylthio), a ureido group having 1 to 15 carbon atoms (e.g. 3-methylureido, and 3,3-dimethylureido), a heterocyclic group having 2 to 10 carbon atoms (e.g. a 3-membered to 12-membered monocyclic ring or condensed ring having at least one hetero atom(s), such as nitrogen, oxygen, and sulfur, for example, 2-furyl, 2-pyranyl, 2-pyridyl, 2-thienyl, 2-imidazolyl, morpholino, 2-quinolyl, 2-benzimidazolyl, 2-benzothiazolyl, and 2-benzoxazolyl), an acyl group having 1 to 8 carbon atoms (e.g. acetyl, benzoyl, and trifluoroacetyl), a sulfamoylamino group having 0 to 10 carbon atoms (e.g. N-butylsulfamoylamino and N-phenylsulfamoylamino), a silyl group having 3 to 10 carbon atoms (e.g. trimethylsilyl, and dimethyl-t-butylsilyl), and a halogen atom (e.g. a fluorine atom, a chlorine atom, and a bromine atom).

The above substituents may further have a substituent, and examples of such a substituent include those mentioned above as examples of $R^1$. The total number of carbon atoms of the substituent is preferably 20 or less, more preferably 12 or less, and further preferably 8 or less.

m represents an inter of 0 to 4, and preferably 1 to 3.

When m is 2 or more, $R^1$s can be the same or different, and may bond together to form a 5- to 7-membered ring.

$Y^1$ represents an aryl group (e.g., a 4-hexadecyloxyphenyl group, 4-dodecanoylaminophenyl group or 2-chloro-4-hexadecyloxycarbonylaminophenyl group), an unsaturated heterocyclic group (e.g., a 2-(5-dodecanoylamino)pyridyl group, an acyl group (e.g., a dodecanoyl group or 4-decyloxybenzoyl group), an alkoxycarbonyl group (e.g., a tetradecylcarbonyl group or hexadecylcarbonyl group), an aryloxycarbonyl group (e.g., a 4-hexadecyloxyphenoxycarbonyl group or 4-dodecanoylaminophenoxycarbonyl group), a carbamoyl group (e.g., an N,N-dicyclohexylcarbamoyl group or N-dodecylcarbamoyl group) or a sulfonyl group (e.g., a dodecylsulfonyl group or hexadecylsulfonyl group), wherein these groups each have an alkyl group whose sum of carbon atoms is 6 or more, preferably 6 to 50, and more preferably 12 to 40, in total. Also, these groups may have a substituent. If the number of total carbon atoms of the alkyl group bonded to $Y^1$ is 6 or more, this is effective to make the coupler of the formula (4) immobilized in a hydrophilic colloid layer and it makes easy to dissolve the coupler in a high-boiling point organic solvent, which is hence preferable.

Examples of the substituent of $X^2$ in the formula (3) include the same substituents of $R^1$ in the formula (4) except for a sulfamoyl group, sulfonamide group, carboxyl group, hydroxyl group, mercapto group and sulfamoylamino group. Given as examples of the substituent of $Z^2$ in the formula (3) and of $Y^1$ in the formula (4) are the substituents having 1 to 50 carbon atoms explained for $R^1$ in the formula (4).

Next, examples of the color-developing agent represented by the formula (3) will be explained. However, the scope of the present invention is not limited to these specific examples.

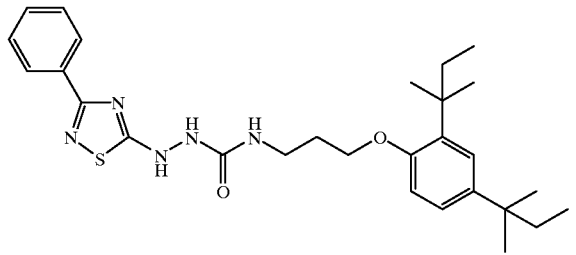

R-201

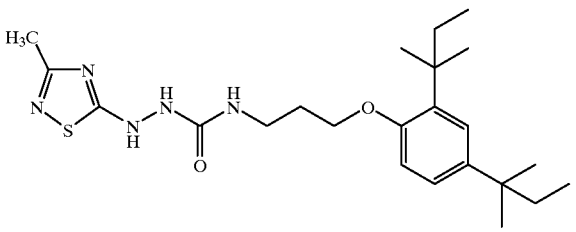

R-202

-continued

Next, examples of the coupler represented by the formula (4) will be explained. However, the scope of the present invention is not limited to these specific examples.

-continued
MC-5
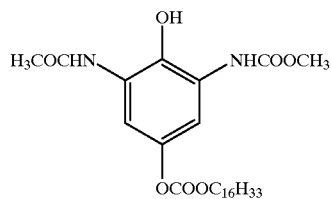
MC-6
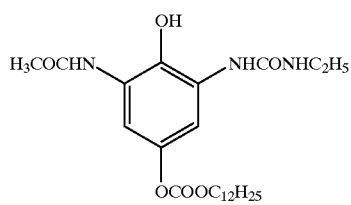
MC-7
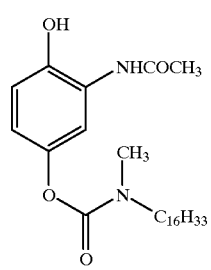
MC-8
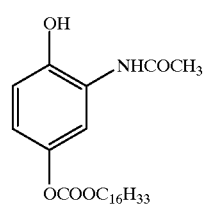
MC-9
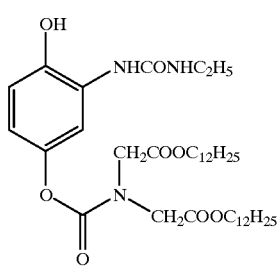
MC-10
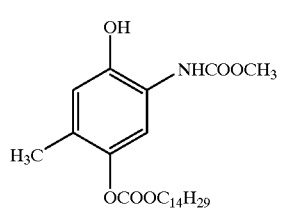
-continued
MC-11
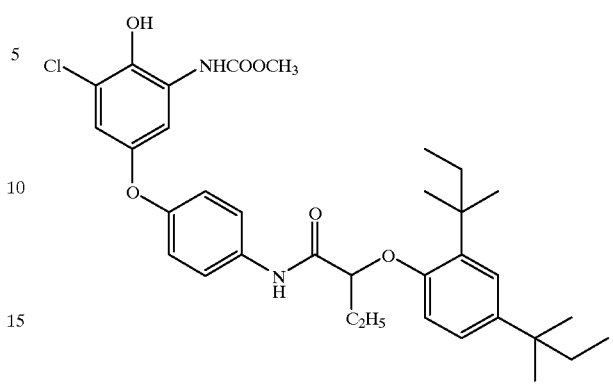
MC-12
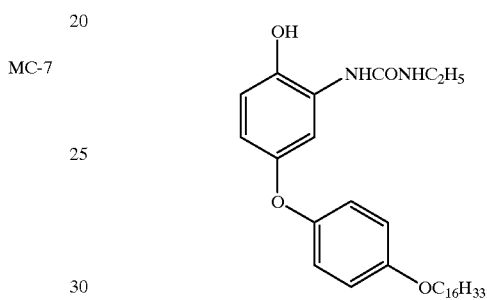
MC-13
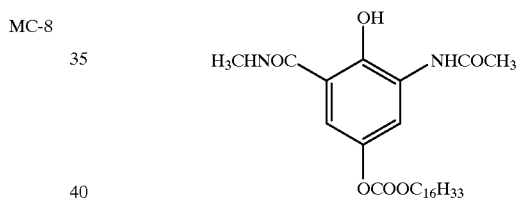
MC-14
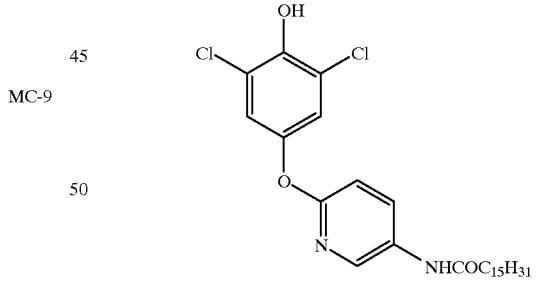
MC-15
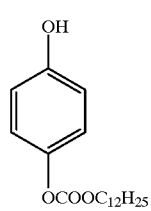

-continued

MC-16
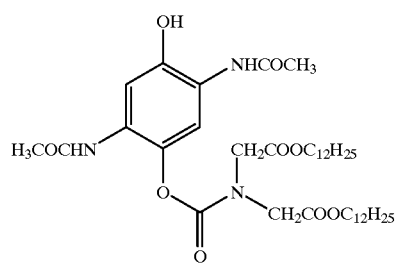

MC-17
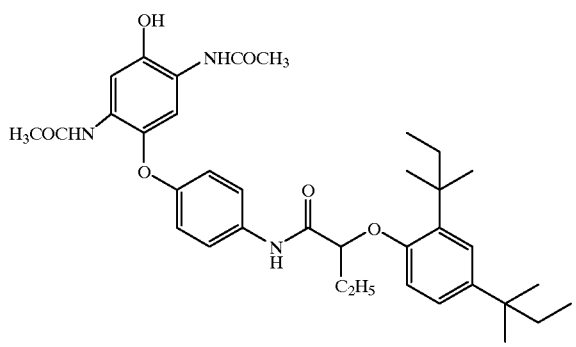

MC-18
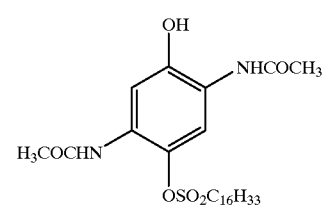

MC-19
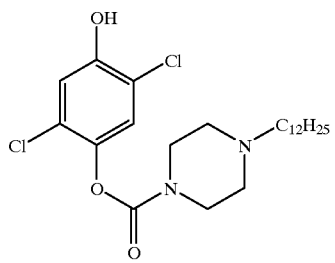

MC-20

-continued

MC-21
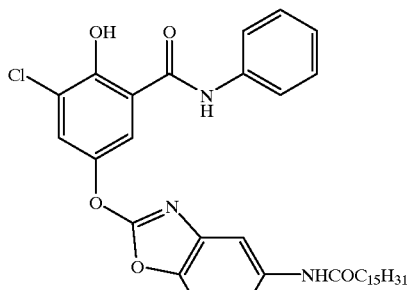

MC-22
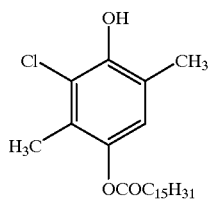

MC-23
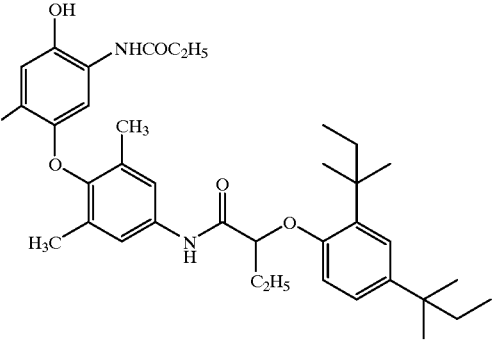

MC-24
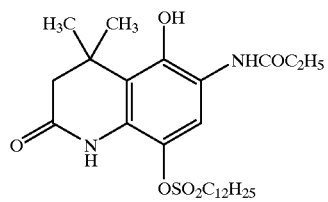

Next, a general method of synthesizing the compound of the present invention will be explained.

SYNTHETIC EXAMPLE 1

Synthesis of Exemplified Compound (R-1)

A method of the synthesis of an exemplified compound (R-1) may refers to the method described in JP-A-09-152702 and the compound (R-1) was synthesized in the following synthetic process according to JP-A-09-152702. Other compounds may be synthesized in the similar manner as above.

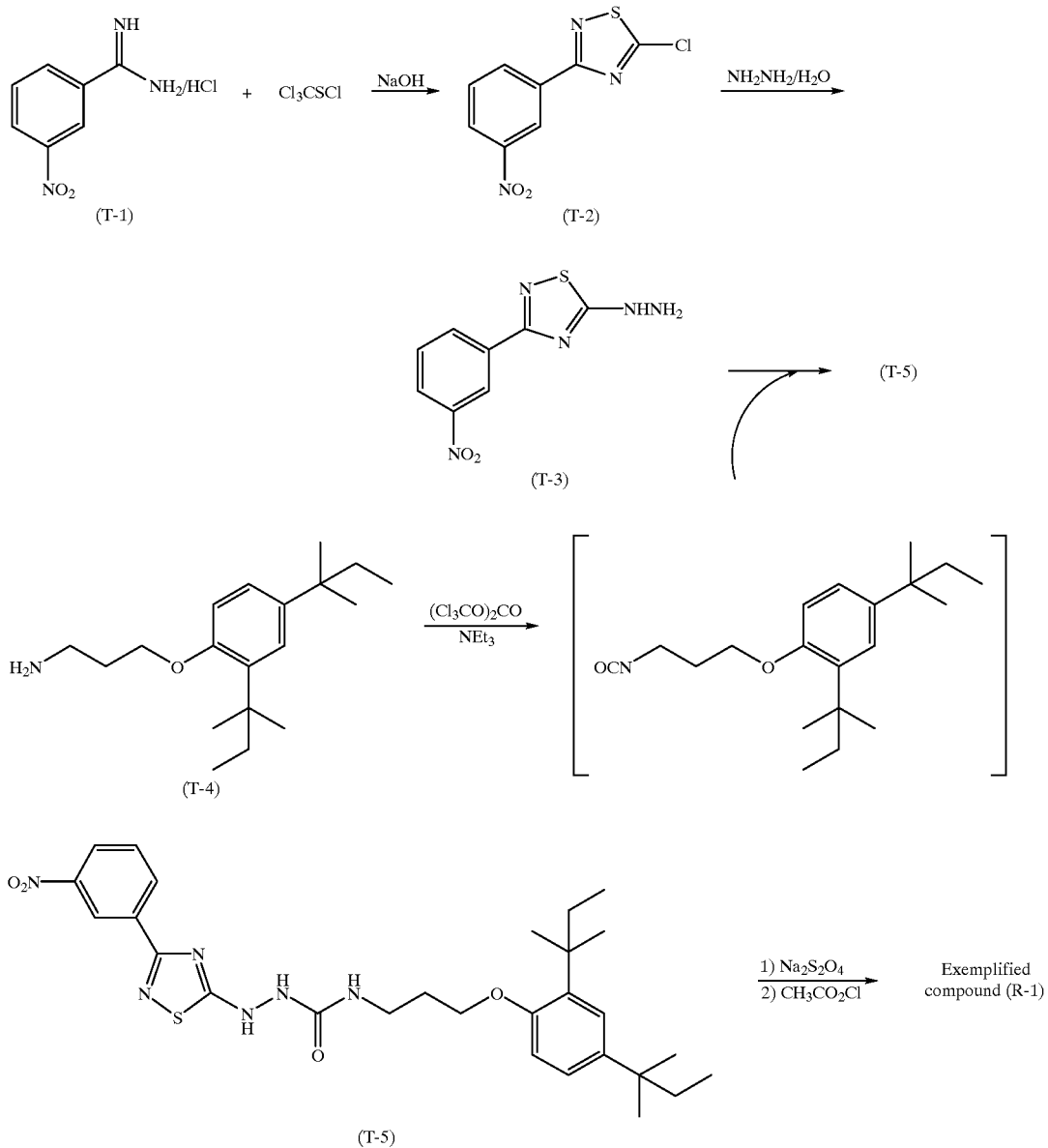

Synthesis of Exemplified Compound (R-1)

Synthesis of Compound (T-3)

102.1 g of the compound (T-1) was suspended in 1 liter of methylene chloride, to which was added 100 g of perchloromethylmercaptan. The reaction system was cooled to 0–5° C. and a solution in which 200 g of sodium hydroxide was dissolved in 600 ml of water was added dropwise to the reaction system such that the reaction temperature was kept at 15° C. or less. After the reaction was completed, the water phase was removed and 50 g of hydrazine hydrate was added dropwise to the organic layer at 15° C. or less. After the reaction was completed, 1 liter of water was added to the reaction solution to carry out an extraction operation. The organic layer was concentrated under reduced pressure to obtain an intermediate (T-3) in an amount of 137.5 g (58%).

Synthesis of Compound (T-5)

100.5 g of triphosgene was dissolved in 2 liter of tetrahydrofuran. Under cooling, 300.0 g of the compound (T-4) and then 150 ml of triethylamine were added dropwise to the mixture. After the dropwise addition was completed, the reaction was continued 1 hour at room temperature, then 237.5 g of the compound (T-3) was divided into five parts which were separately added to the reaction mixture. After the addition was completed, the reaction was further continued for 2 hours. To the reaction mixture were added 2 liters of ethyl acetate and 2 liters of water to carry out extraction, followed by washing further with 2 liter of water twice. Then, the organic layer was dried using magnesium sulfate anhydride and the solvent was distilled off under reduced pressure. The residue was recrystallized from acetonitrile to obtain 360.1 g (65%) of Compound (T-5) as white crystals.

Synthesis of Exemplified Compound (R-1)

27.7 g of the intermediate compound (T-5) was dissolved in 500 ml of ethyl acetate, 400 ml of water and 100 ml of ethanol, to which was further added 87 g of sodium hydrosulfite. The mixture was reacted for 2 hours and thereafter subjected to an extraction operation, followed by washing with 500 ml of water twice. The organic layer was dried using magnesium sulfate anhydride and the solvent was distilled off under reduced pressure. The residue was dissolved in 100 ml of DMAC and 7 ml of triethylamine, to which was added dropwise 4.0 ml of methanesulfonyl chloride under ice-cooling such that the internal temperature did not exceed 15° C. Then, the reaction was further run for 1 hour and the reaction mixture was poured into 500 ml of 1N hydrochloric acid. The precipitated crystals were collected by filtration and washed, followed by drying to obtain crude crystals. The crude crystals were recrystallized from acetonitrile to obtain 24.1 g (80%) of Exemplified compound (R-1) as white crystals.

SYNTHETIC EXAMPLE 2

Synthesis of Exemplified compound (R-101)

A method of the synthesis of an exemplified compound (R-101) may refers to the method described in JP-A-09-152702 and the compound (R-101) was synthesized in the following synthetic process according to JP-A-09-152702.

ice. After the dropwise addition was completed, the reaction was continued at 15° C. or less for 1 hour and the reaction mixture was then subjected to an extraction operation. The extract was washed with 200 ml of water twice. The organic layer was dried using magnesium sulfate anhydride and the solvent was distilled off under reduced pressure. To the residue was added 200 ml of tetrahydrofuran and was then added dropwise 101 g of hydrazine monohydrate under ice-cooling. In succession to the dropwise addition, the resulting mixture was reacted for one hour at room temperature, followed by addition of 200 ml of water to precipitate crystals. The crystals were collected by filtration and washed with 300 ml of acetonitrile, followed by drying. Thus, 58.3 g (72%) of a compound (T-6) was obtained as white crystals.

Synthesis of Exemplified Compound (R-101)

50.8 g of triphosgene was dissolved in 1 liter of tetrahydrofuran. 149.8 g of the compound (T-4) and then 104 g of triethylamine were added dropwise to the mixture while cooling. After the dropwise addition was completed, the reaction was continued for one hour at room temperature, then 64.8 g of the compound (T-6) was divided into five parts which were separately added to the reaction mixture. After the addition was completed, the reaction was further continued for 2 hours. To the reaction mixture were added 1 liter of ethyl acetate and 1 liter of water to carry out

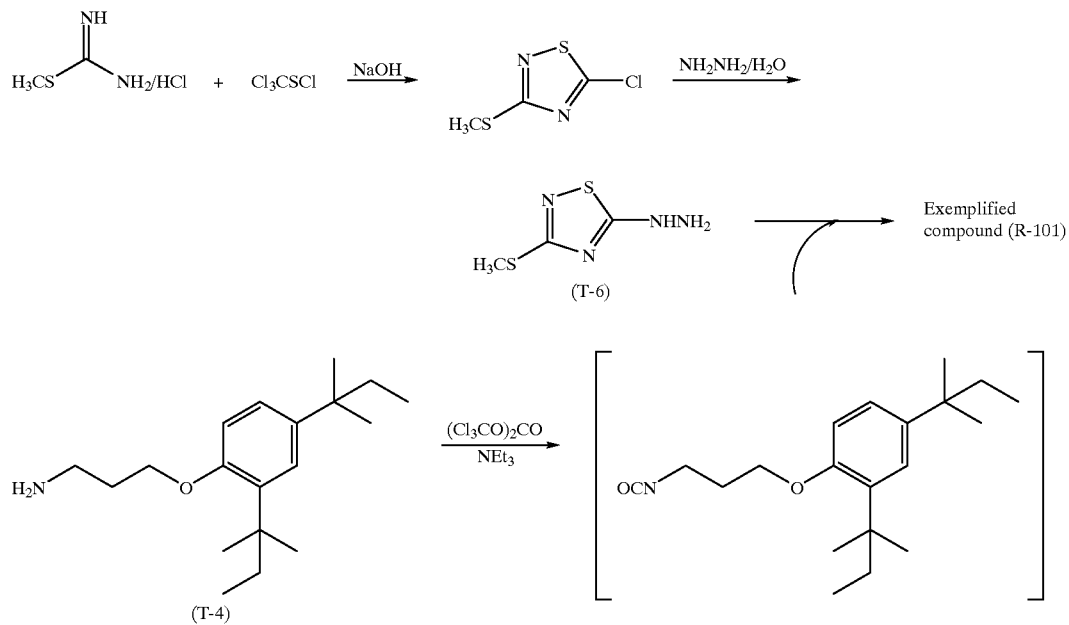

Synthesis of Compound (T-6)

69.5 g of methylisothiourea was dissolved in 500 ml of methylene chloride, to which was then added 92.9 g of perchloromethylmercaptan. A solution obtained by dissolving 100 g of sodium hydroxide in 200 ml of water was added dropwise to the mixture while controlling the internal temperature at 50° C. or less under cooling using methanol/dry extraction, followed by washing further with 1 liter of water twice. Then, the organic layer was dried using magnesium sulfate anhydride and the solvent was distilled off under reduced pressure. The residue was recrystallized from acetonitrile to obtain 118.9 g (62%) of Exemplified compound (R-101) as white crystals.

Synthesis of Exemplified Compounds (R-112) and (R-114)

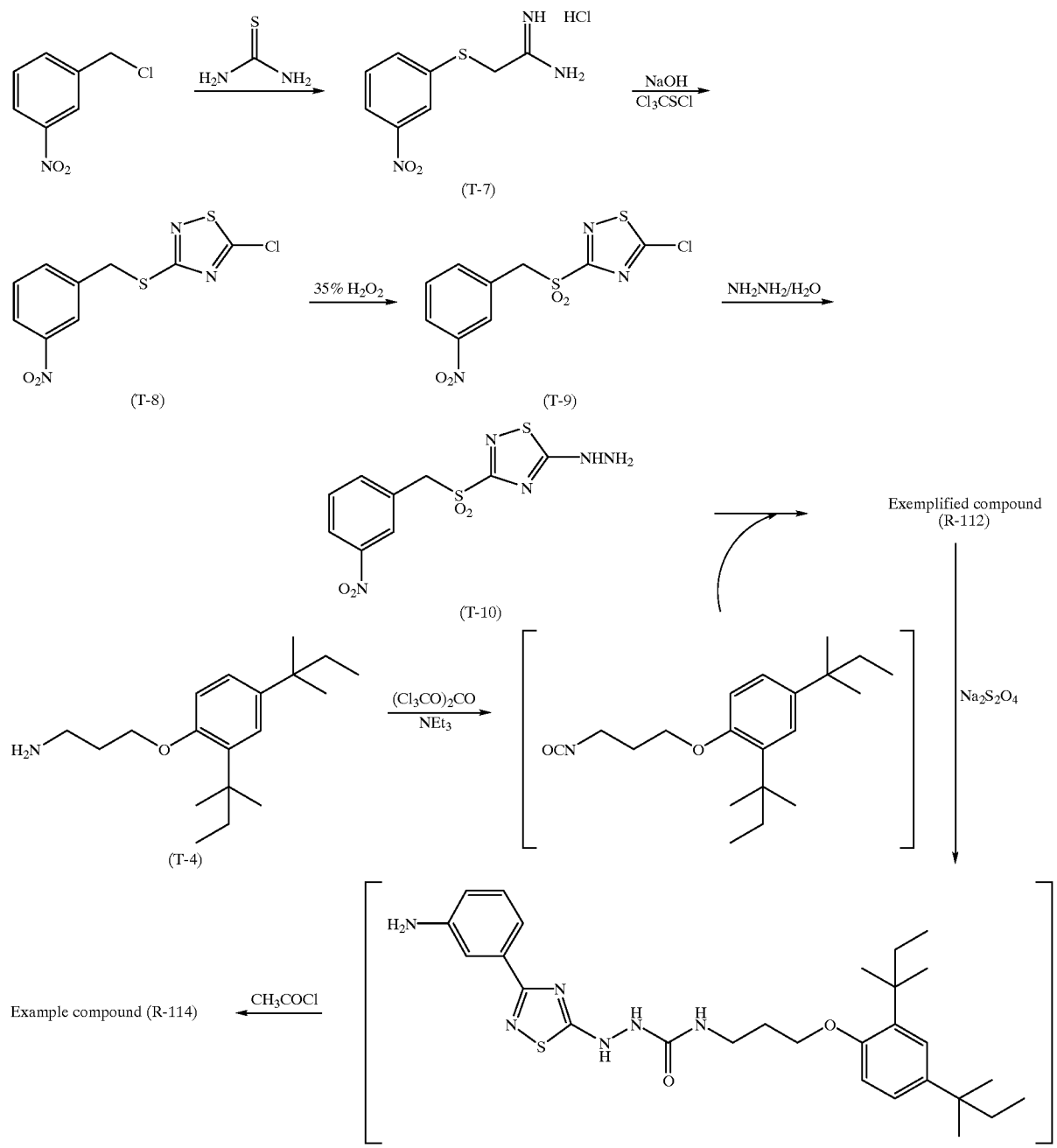

Synthesis of Compound (T-7)

171.5 g of m-nitrobenzyl chloride and 80 g of thiourea were dissolved in 1 liter of isopropyl alcohol and the mixture was heated under reflux for 2 hours. In succession to the reaction, the reaction mixture was cooled to room temperature to collect the precipitated crystals by filtration, which were then washed with 300 ml of isopropyl alcohol. Thus, 237.6 g (96%) of a compound (T-7) was obtained as white crystals.

A compound (T-8) was synthesized according to the synthetic method of the Exemplified compound (R-101).

Synthesis of Compound (T-9)

57.5 g of the compound (T-8) was suspended in 300 ml of acetic acid, to which was added dropwise 35 ml of aqueous 35% hydrogen peroxide solution at an internal temperature of 50° C. The reaction system was completely uniformed within one hour after the dropwise addition was finished and thus the reaction was completed. The reaction solution was poured into 1 liter of 1N hydrochloric acid to collect the precipitated crystals by filtration, which were then washed with water. The resulting crude crystals were subjected to a silica gel column chromatography to obtain 30.9 g (44%) of a compound (T-9) as white crystals from the eluate of hexane/ethyl acetate (3:1).

A compound (T-10) and Exemplified compound (R-112) were synthesized according to the synthetic method of Exemplified compound (R-101).

Synthesis of Exemplified Compound (R-114)

33.2 g of Exemplified compound (R-112) was dissolved in 500 ml of ethyl acetate, 400 ml of water and 100 ml of ethanol, to which was further added 87 g of sodium hydrosulfite. The mixture was reacted for 2 hours and thereafter subjected to an extraction operation, followed by washing with 500 ml of water twice. The organic layer was dried using magnesium sulfate anhydride and the solvent was distilled off under reduced pressure. The residue was dissolved in 100 ml of DMAC and 7 ml of triethylamine, to which was added dropwise 3.8 g of acetyl chloride under ice-cooling such that the internal temperature did not exceed 15° C. Then, the reaction was further run for 1 hour and the reaction mixture was poured into 500 ml of 1N hydrochloric acid. The precipitated crystals were collected by filtration and washed, followed by drying to obtain crude crystals. The crude crystals were recrystallized from acetonitrile to obtain 25.3 g (68%) of Exemplified compound (R-114) as white crystals. Synthetic Example 3 Synthesis of Exemplified compound (R-201)

A method of the synthesis of Exemplified compound (R-201) is described in detail in JP-A-09-152702 and the compound (R-201) was synthesized in the following synthetic process according to JP-A-09-152702.

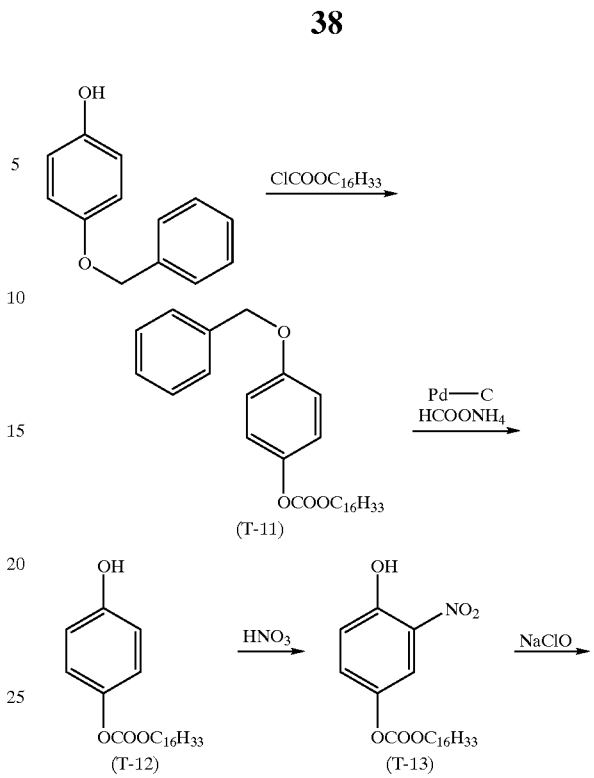

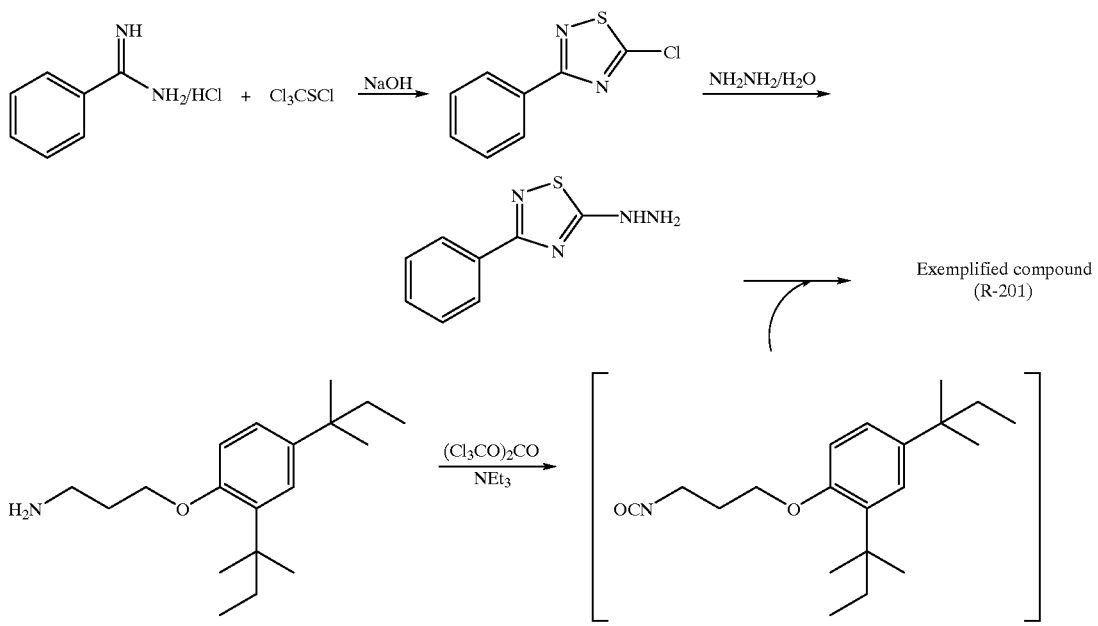

SYNTHETIC EXAMPLE 4

Synthesis of Exemplified Compound (MC-1)

The synthesis of the compound was carried out according to the following synthetic route.

-continued

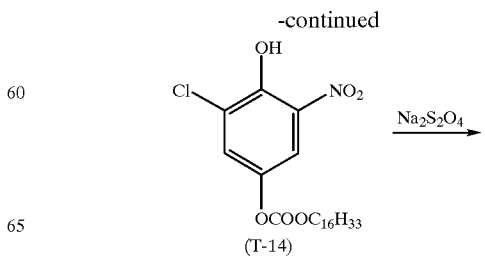

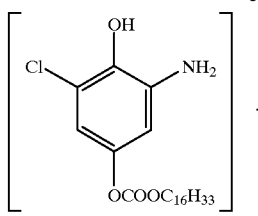 →AcCl→ Exemplified compound (MC-1)

Synthesis of Compound (T-11)

200 g of hydroquinone monobenzyl ether was dissolved in a mixture solvent of 500 ml of acetonitrile and 500 ml of dimethylacetoamide (hereinafter abbreviated to as DMAC), to which 167 ml of triethylamine was added. Then, 305 g of hexadecyl chloroformate was added dropwise to the mixture in a room temperature atmosphere while the internal temperature was controlled to be kept at 35° C. or less. After the addition was completed, the reaction was continued for 1 hour and thereafter the reaction solution was poured into 3 liter of 1N hydrochloric acid carefully. The precipitated crystals were collected by filtration and washed with 300 ml of acetonitrile, followed by drying. Thus 435 g (93%) of a compound (T-11) was obtained as white crystals.

Synthesis of Compound (T-12)

47 g of the compound (T-11), 1 g of 10% Pd-C and 22 g of ammonium formate were dissolved in 500 ml of methanol and the mixture was heated under reflux for 4 hours. After completion of the reaction, the catalyst was collected from the reaction solution by filtration using celite in a heated condition. 2 liter of water was poured into the filtrate and the precipitated crystals were collected by filtration and washed with 100 ml of methanol, followed by drying. Thus, a compound (T-12) was obtained in an amount of 36.3 g (98%) as white crystals.

Synthesis of Compound (T-13)

37.8 g of the compound (T-12) was dissolved in 500 ml of methylene chloride, to which was added dropwise 8 ml of nitric acid with a specific gravity of 1.38 in a room temperature atmosphere. The reaction was further continued for 1 hour and 1 liter of hexane was poured into the reaction solution and the precipitated crystals were collected by filtration and washed with 100 ml of isopropyl alcohol, followed by drying. Thus, a compound (T-13) was obtained in an amount of 34.7 g (82%) as yellow crystals.

Synthesis of Compound (T-14)

42.3 g of the compound (T-13) was dissolved in 200 ml of methanol, to which was then added dropwise 85 ml of an aqueous sodium hypochlorite solution having an effective chlorine concentration of 5% in a room temperature atmosphere. The mixture was further reacted for 2 hours. 500 ml of ethyl acetate and 800 ml of 1N hydrochloric acid were poured into the reaction solution to perform an extraction operation, followed by washing with 500 ml of water twice. Then, the organic layer was dried over magnesium sulfate anhydride and the solvent was distilled off under reduced pressure to obtain 35.2 g (77%) of a compound (T-14) as pale red crystals. Synthesis of Exemplified Compound (MC-1)

45.7 g of the compound (T-14) was dissolved in 500 ml of ethyl acetate, 400 ml of water and 100 ml of ethanol, to which was further added 87 g of sodium hydrosulfite. After the mixture was reacted for 2 hours, an extraction operation was performed, followed by washing with 500 ml of water twice. The organic layer was dried using magnesium sulfate anhydride and the solvent was distilled off under reduced pressure. The residue was dissolved in 100 ml of DMAC, to which was then added dropwise 8 ml of acetyl chloride in a room temperature atmosphere while the internal temperature did not exceed 35° C. After the addition was completed, the resulting mixture was further reacted for 1 hour and the reaction mixture was poured into 500 ml of 1N hydrochloric acid. The precipitated crystals were collected by filtration, washed with water and dried to obtain crude crystals. The crude crystals were recrystallized from acetonitrile to obtain 31.9 g (68%) of Exemplified compound (MC-1) as white crystals.

The color-developing agent of the present invention is used together with a compound (a coupler) that can form a dye by oxidation coupling reaction. This coupler may be a so-called "four-equivalent coupler" or "two-equivalent coupler", which is used in a conventional system using a p-phenylenediamine-series developing agent, but in the present invention, a "two-equivalent coupler" is preferable. Specific examples of the coupler are described in detail, for example, in "Theory of The Photographic Process" (4th Ed., edited by T. H. James, Macmillan, 1977), pages 291 to 334 and 354 to 361, and in JP-A-58-12353, JP-A-58-149046, JP-A-58-149047, JP-A-59-11114, JP-A-59-124399, JP-A-59-174835, JP-A-59-231539, JP-A-59-231540, JP-A-60-2951, JP-A-60-14242, JP-A-60-23474, and JP-A-60-66249.

Examples of a coupler that is preferably used in the present invention include couplers represented by formulae (1) to (12) described in JP-A-9-152705. Further, couplers (C-1) to (C-50) described in JP-A-9-152705, pages 24 to 37, and couplers (C-1) to (C-80) described in JP-A-8-286340, pages 29 to 44, can be mentioned as preferable examples, but the present invention is not limited to them.

Further, specific examples of a coupler that can be used in the present invention are shown below, but the present invention is not limited to them.

(C-1)
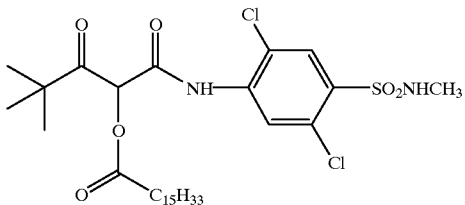

(C-2)
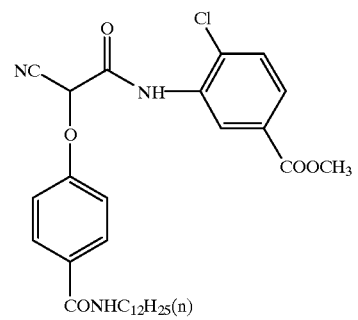

(C-3)
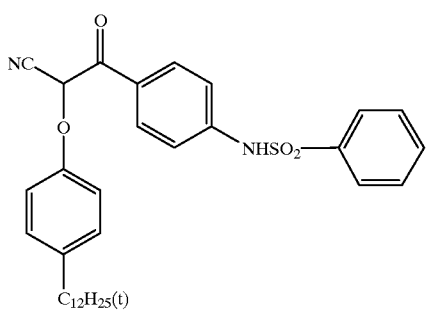

(C-4)
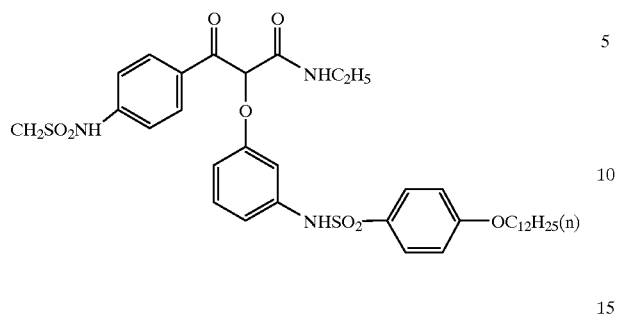
(C-8)
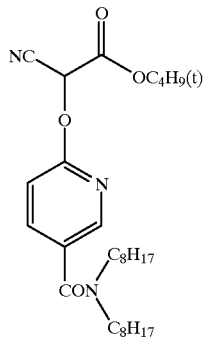
(C-5)
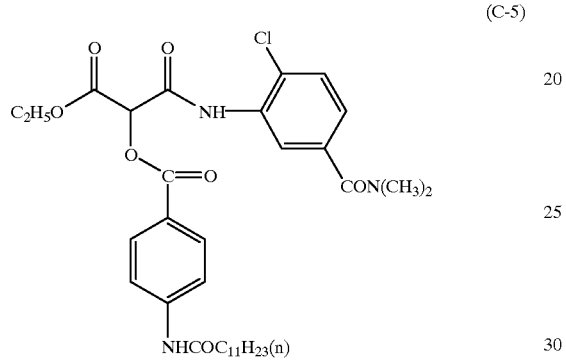
(C-9)
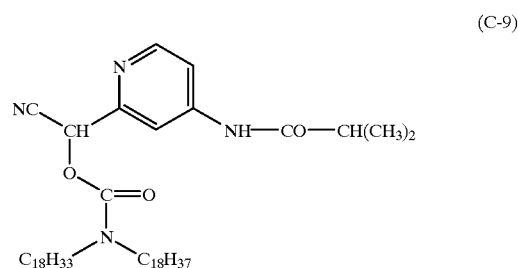
(C-6)
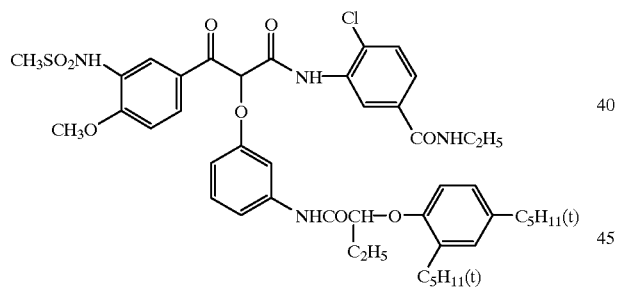
(C-10)
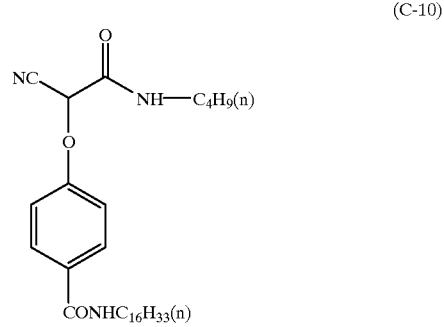
(C-7)
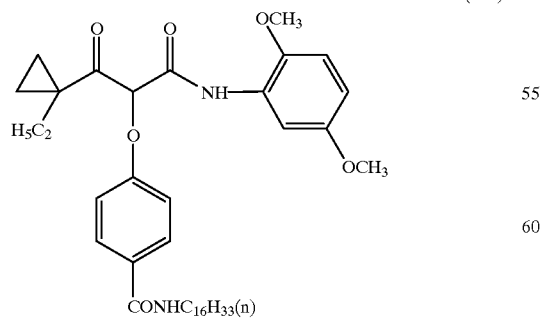
(C-11)
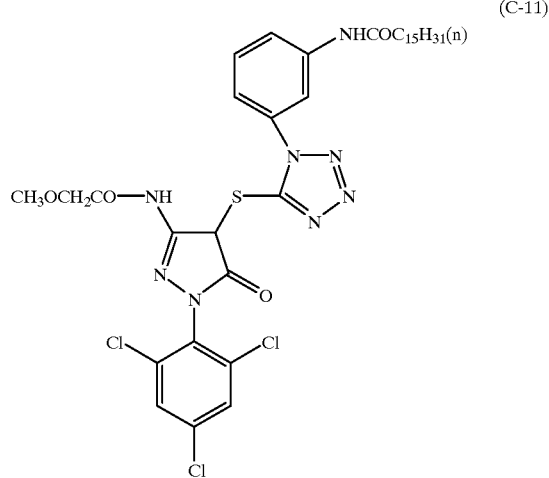

(C-12) 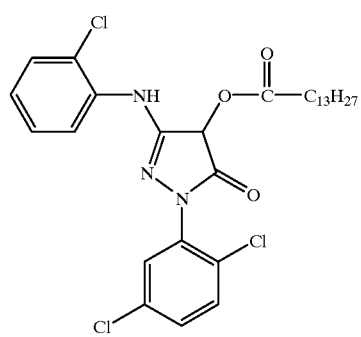
(C-17) 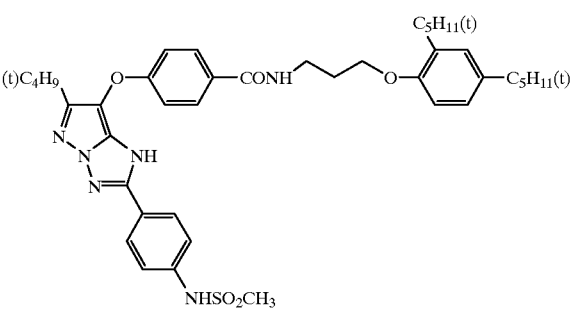
(C-13) 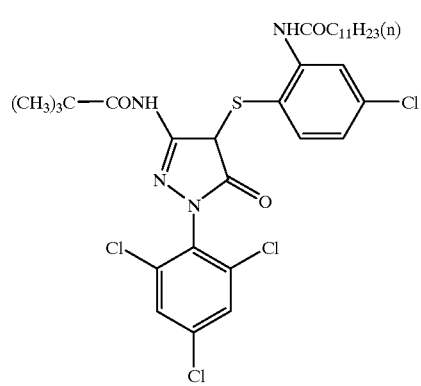
(C-18) 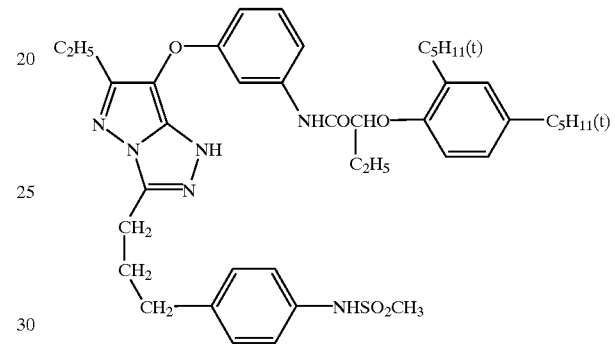
(C-14) 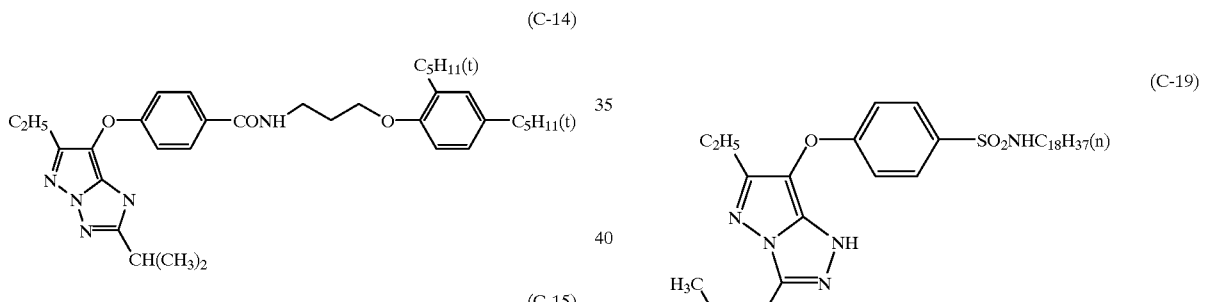
(C-15)
(C-19) 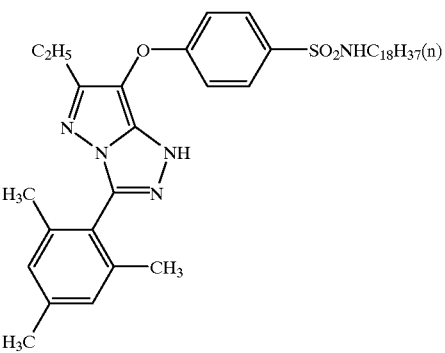
(C-16) 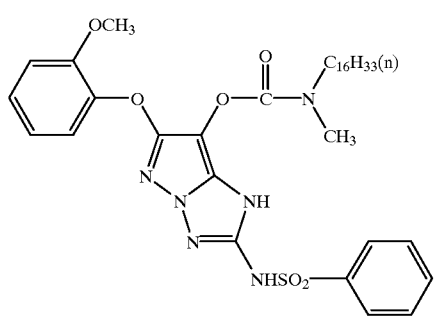
(C-20) 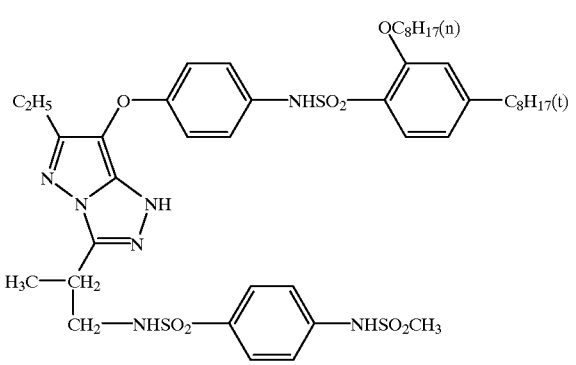
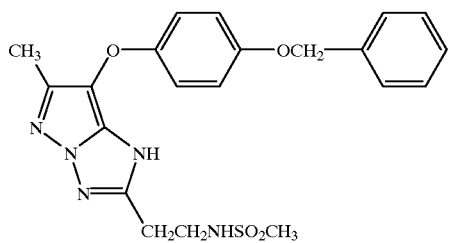

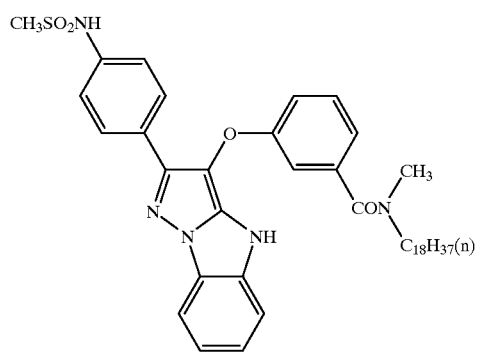
(C-21)
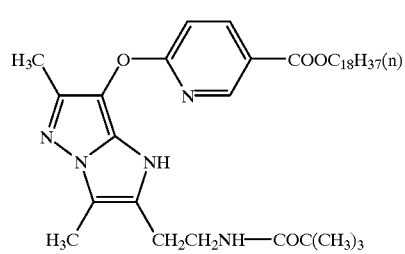
(C-22)
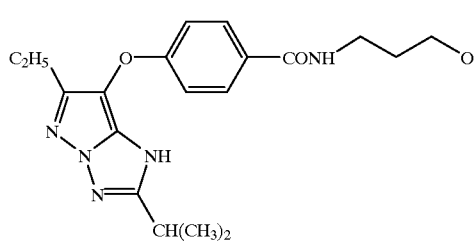
(C-23)
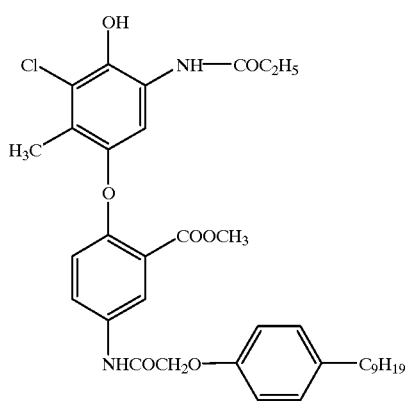
(C-24)
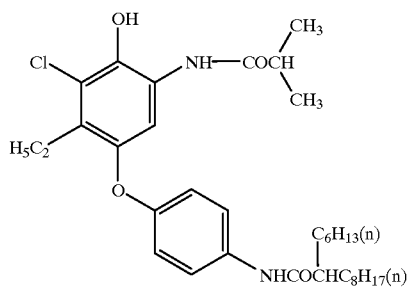
(C-25)
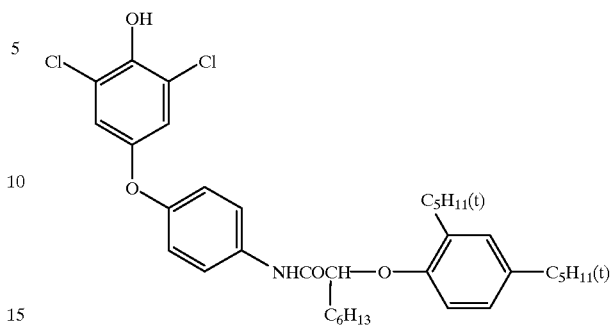
(C-26)
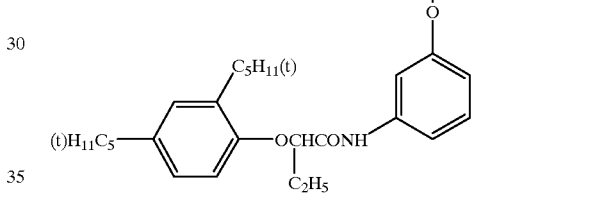
(C-27)
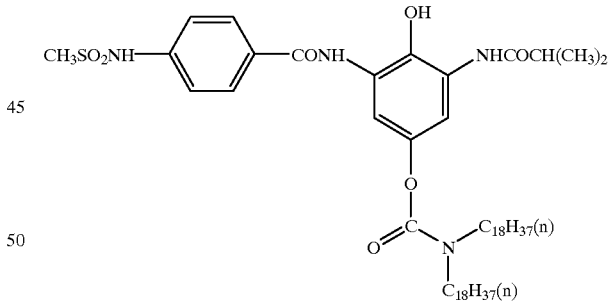
(C-28)
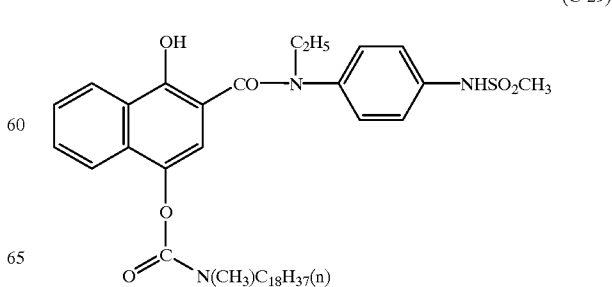
(C-29)

(C-30)
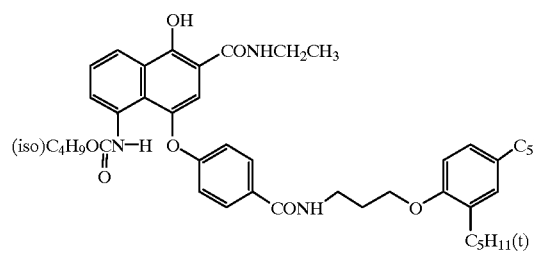
(C-31)
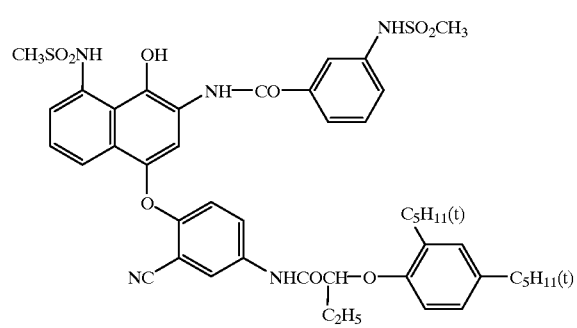
(C-32)
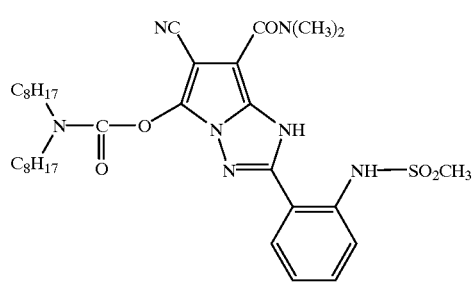
(C-33)
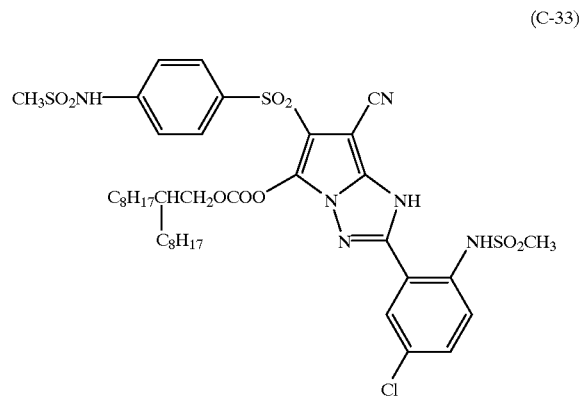
(C-34)
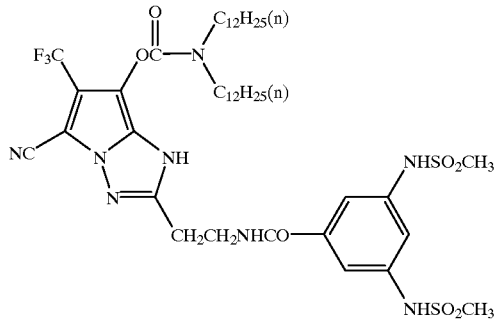
(C-35)
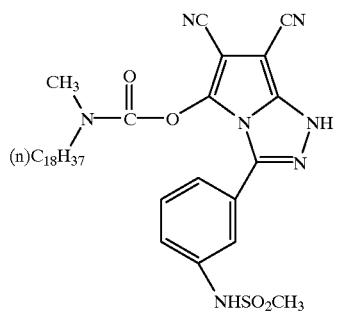
(C-36)
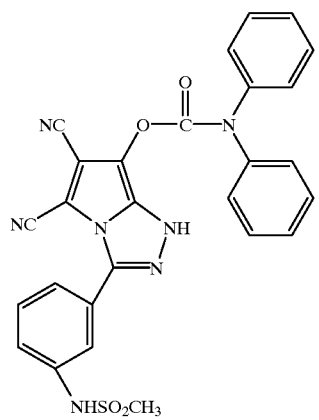
(C-37)
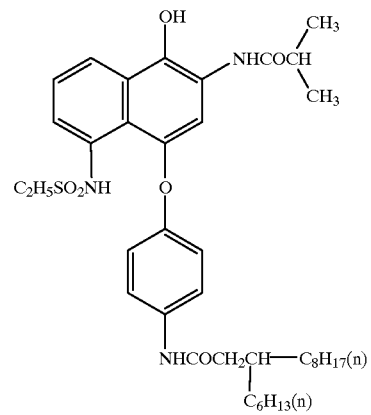

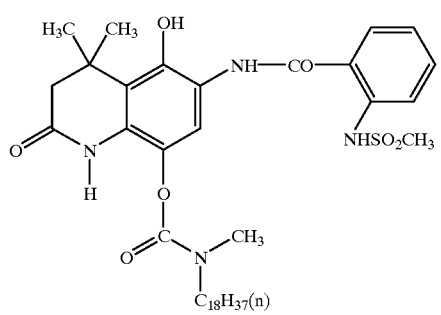
(C-38)
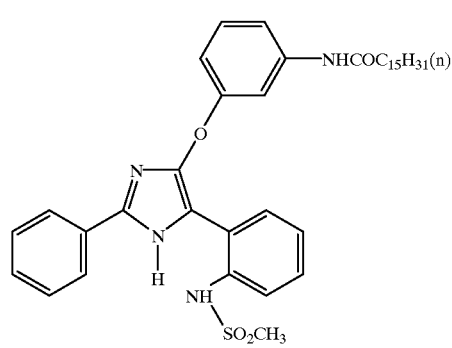
(C-39)
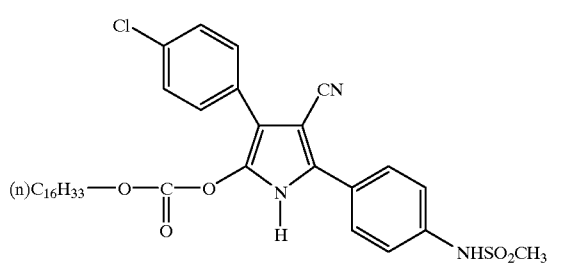
(C-40)
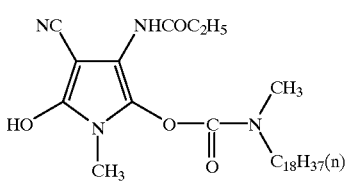
(C-41)
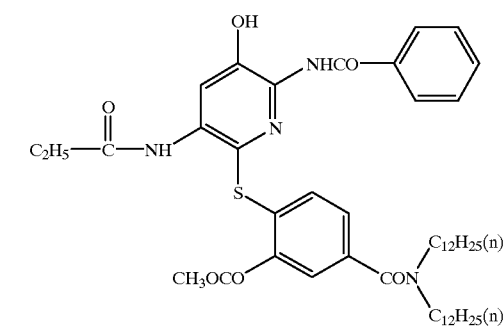
(C-42)
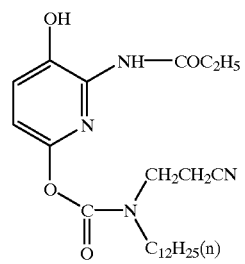
(C-43)
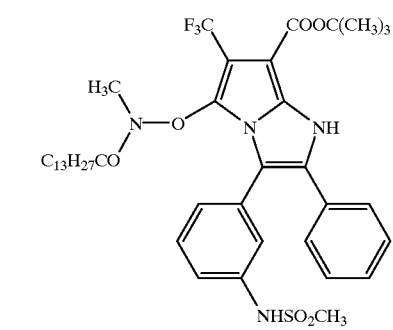
(C-44)
(C-45)
(C-46)
(C-47)

-continued (C-48)
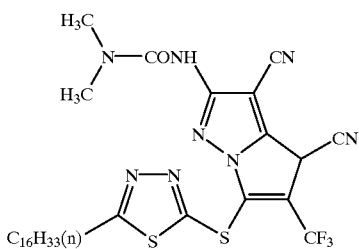

(C-49)
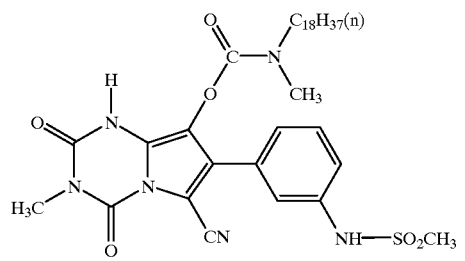

(C-50)
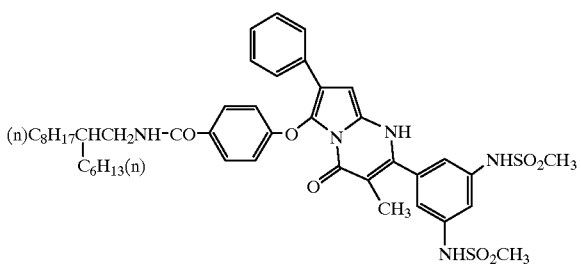

Although the amount to be added, of the couplers that are used with the color developing agent of the present invention, varies according to the molar extinction coefficient ($\epsilon$) of a produced dye, in order to obtain an image density of 1.0 or more in terms of reflection density, in the case of couplers wherein the $\epsilon$ of the dye that will be produced by coupling is of the order of 5,000 to 500,000, suitably the amount to be added, of the couplers that are used in the present invention, is of the order of generally 0.001 to 100 mmol/m$^2$, preferably 0.01 to 10 mmol/m$^2$, and more preferably 0.05 to 5 mmol/m$^2$, in terms of the coated amount.

The amount of the color-developing agent of the present invention to be added is generally 0.01 to 100 times, preferably 0.1 to 10 times, and more preferably 0.2 to 5 times, the amount of the coupler in molar ratio.

In the present invention, an auxiliary developing agent can be preferably used. Herein the term "an auxiliary developing agent" means a substance that functions to promote the transfer of electrons from the color-developing agent to silver halides in the development process of the silver halide development; and the auxiliary developing agent is a compound capable of releasing electrons according to the Kendall-Pelz rule.

As examples of these compounds, compounds (ETA-1) to (ETA-36) described in JP-A-9-152705, and compounds D-1 to D-35 described in JP-A-9-146248 can be mentioned.

In the present invention, a blocked photographic reagent that will release a photographically useful group at the time of processing can be used. As examples of these, those described in paragraphs 0073 to 0077 of JP-A-9-152705 can be mentioned.

The light-sensitive material of the present invention, preferably, has on a base, a photosensitive silver halide, at least one color-developing agent represented by the above formula (1), (2), or (3), a coupler (when the compound represented by formula (3) is used as the color-developing agent, at least one coupler represented by the above formula (4)), and a binder, and, if required, an organic metal salt oxidant, and the like can be contained. In many cases, these components are added to the same layer, but they can be separately added to different layers if they are in reactive states.

Hydrophobic additives such as a color-developing agent, a coupler, and an image-formation-promoter explained later, which are used in the present invention may be introduced into the layers of the light-sensitive material (i.e. photographic constitutional layers such as hydrophilic colloid layer) by a known method such as a method described in U.S. Pat. No. 2,322,027. The color-developing agent and the coupler can be preferably introduced into the same layer, although they may be introduced into separate layers. When they are introduced into the same layer, preferably they are introduced into the silver halide emulsion layer. Though an auxiliary developing agent may be added to any one of the photographic constitutional layers, it is preferably introduced into a layer, such as the intermediate layer or the protective layer, adjacent to the layers containing a silver halide emulsion. When these compounds are to be introduced into the photographic structure layer, a high-boiling point organic solvent as described in JP-A-59-83154, JP-A-59-178451, JP-A-59-178452, JP-A-59-178453, JP-A-59-178454, JP-A-59-178455 and JP-A-59-178457, U.S. Pat. Nos. 4,555,470, 4,536,466, 4,536,467, 4,587,206, 4,555,476, 4,599,296, JP-B-3-62256 may be used, as required, together with a low-boiling point organic solvent having a boiling point as low as 50° C. to 160° C.

Further, these dye-donative compounds such as a coupler and a color-developing agent, diffusion-proof reducing agents, high-boiling organic solvents, and the like can be used singly, or in the form of a combination of two or more. As the case of color-developing agents, the compound represented by formula (1), (2) or (3) can be used in combination with other compound that is not included in the formula.

The light-sensitive material of the third embodiment of the present invention may use couplers forming a yellow color, magenta color or cyan color in combination with the compounds represented by the formulae (3) and (4). As these couplers, known couplers may be used in combination of two or more.

The amount of the high-boiling point organic solvent to be used is generally 10 g or less, preferably 5 g or less, and more preferably 1 g to 0.1 g, per g of a color-image forming compound to be used. The amount of the solvent is generally 1 cc or less, preferably 0.5 cc or less and more preferably 0.3 cc or less based on 1 g of the binder.

For example, the amount of the high-boiling point organic solvent to be used is generally 10 g or less and preferably 5 g or less, per g of the total amount of the color-developing agent and the coupler to be used.

A dispersion method that use a polymer, as described in JP-B-51-39853 and JP-A-51-59943, and a method wherein the addition is made with them in the form of a dispersion of fine particles, as described, for example, in JP-A-6230242 and JP-A-63-271339, can also be used.

If the compounds are substantially insoluble in water, besides the above methods, a method can be used wherein the compounds may be made into fine particles to be dispersed and contained in a binder.

In dispersing the hydrophobic compound in a hydrophilic colloid, various surface-active agents can be used; examples are listed in JP-A-59-157636, pages (37) to (38), and in the RD publication shown in a table below.

In the photographic material of the present invention, use can be made of a compound that can activate the development and make the image stable. Preferable specific compounds for use are described in U.S. Pat. No. 4,500,626, the 51st column to the 52nd column.

In order to obtain colors ranging widely on the chromaticity diagram by using three primary colors: yellow, magenta, and cyan, use is made of a combination of at least three silver halide emulsion layers photosensitive to respectively different spectral regions. For examples, a combination of three layers of a blue-sensitive layer, a green-sensitive layer, and a red-sensitive layer, and a combination of a green-sensitive layer, a red-sensitive layer, and an infrared-sensitive layer, can be mentioned. The photosensitive layers can be arranged in various orders known generally for color photographic materials. Further, each of these photosensitive layers can be divided into two or more layers if necessary.

In the photographic material, various auxiliary layers can be provided, such as a protective layer, an underlayer, an intermediate layer, an antihalation layer, and a backing layer. Further, in order to improve the color separation, various filter dyes can be added.

The silver halide grains used in the present invention are made of silver bromide, silver chloride, silver chlorobromide, silver chloroiodide, silver iodobromide, or silver chloroiodobromide. Other silver salts, such as silver rhodanate, silver sulfide, silver selenide, silver carbonate, silver phosphate, or a silver salt of an organic acid, may be contained in the form of independent grains or as part of silver halide grains. If it is desired to make the development/desilvering (bleaching, fixing, and bleach-fix) step rapid, silver halide grains having a high silver chloride content are desirable. Further, if the development is to be restrained moderately, it is preferable to contain silver iodide. The preferable silver iodide content varies depending on the intended photographic material. For example, in the case of X-ray photographic materials, the preferable silver iodide content is in the range of 0.1 to 15 mol %, and in the case of graphic art and micro photographic materials, the preferable silver iodide content is in the range of 0.1 to 5 mol %. In the case of photographic materials for shooting represented by color negatives, preferably silver halide contains 1 to 30 mol %, more preferably 5 to 20 mol %, and particularly preferably 8 to 15 mol %, of silver iodide. It is preferable to incorporate silver chloride in silver iodobromide grains, because the lattice strain can be made less intense.

The grains of the silver halide emulsion for use in the present invention preferably have a distribution or a structure with respect to the halogen composition. Typical examples thereof are grains having a double structure, or core-shell-type grains wherein the halogen composition is different in the surface layer and the inside part of the grains, as disclosed, respectively, in JP-B-43-13162 and in JP-A-61-215540, JP-A-60-222845, and JP-A-61-75337. Instead of a simple double structure, a triple structure, as described in JP-A-60-222844, an even larger-number multilayer structure, or a structure wherein the surface of grains having a core-shell double structure has a thin silver halide layer different in composition from that of the said surface, can be used.

In order to make the inside of grains have a structure, not only the enclosing structure, as mentioned above, but also a so-call Functioned structure can be used to form grains.

Examples thereof are disclosed, for example, in JP-A-59-133540 and JP-A-58-108526, European Patent No. 199 290(A2), JP-B-58-24772, and JP-A-59-16254. Crystals to be junctioned have a composition different from that of host crystals, and they can be junctioned and formed at the edges, corners, or planes of the host crystals. Such Functioned crystals can be formed if host crystals have a uniform halogen composition or a core-shell-type structure.

In the case of a Functioned structure, not only a combination of silver halides but also a combination of a silver halide with a silver salt compound having no rock salt structure, such as silver rhodanate and silver carbonate, can be used for the functioned structure. A non-silver salt compound, such as lead oxide, may be used if a junctioned structure is possible.

In the case of grains of silver iodobromide or the like having these structures, a preferable mode is that the core part is higher in silver iodide content than the shell part. Reversely, in some cases, grains having a lower silver iodide content in the core part than in the shell part are preferable. Similarly, in the case of grains having a junctioned structure, the silver iodide content of the host crystals is relatively higher than that of the junctioned crystals, or this may be reversed. The boundary part of the grains having these structures in which different halogen compositions are present, may be distinct or indistinct. Also preferable is a mode wherein the composition is continuously changed positively.

It is important that in the case of that two or more silver halides are present as mixed crystals, or as silver halide grains having structures, the halogen composition distribution amoung grains is controlled. The method of measuring the halogen composition distribution among grains is described in JP-A-60-254032. A desirable property is that the halogen distribution among grains is uniform. In particular, a highly uniform emulsion having a deviation coefficient of 20% or below is preferable. Another preferable mode is an emulsion in which the grain size and the halogen composition are correlated. An example correlation is a larger grain size with a larger iodine content, and vice versa (smaller grain size, lower iodine content). Depending on the purpose, the reversed correlation or a correlation using some other halogen composition can be used. For this purpose, it is preferable to mix two or more emulsions different in composition.

It is important to control the silver halide composition near the surface of grains. An increase in the silver iodide content or the silver chloride content at the part near the surface changes the adsorption of a dye or the developing speed. Therefore, the silver halide composition can be chosen in accordance with the purpose. To change the halogen composition at the part near the surface, either the structure enclosing the whole of a grain or the structure wherein only part of a grain is attached another silver halide different in halogen composition, can be chosen. For example, in the case of a tetradecahedral grain having (100) and (111) planes, only one plane is changed in halogen composition, or in another case, one of the main plane and the side plane of a tabular grain is changed in halogen composition.

In the silver halide grains used in the present invention, in accordance with the purpose, any of regular crystals having no twin plane, and those described in "Shashin Kogyo no Kiso, Ginen Shashin-hen", edited by Nihon Shashin-gakkai (Corona Co.), page 163, such as single twins having one twin plane, parallel multiple twins having two or more parallel twin planes, and nonparallel multiple twins having two or more nonparallel twin planes, can be chosen and used. An example in which grains different in shape are mixed is disclosed in U.S. Pat. No. 4,865,964, and if necessary this method can be chosen. In the case of regular crystals, cubes having (100) planes, octahedrons having (111) planes, and dodecahedral grains having (110) planes, as disclosed in JP-B-55-42737 and JP-A-60-222842, can be used. Further, (h11) plane grains represented by (211), (hh1) plane grains represented by (331), (hk0) plane grains represented by (210) planes, and (hk1) plane grains represented by (321) planes, as reported in "Journal of Imaging Science", Vol. 30, page 247 (1986), can be chosen and used in accordance with the purpose, although the preparation is required to be adjusted. Grains having two or more planes in one grain, such as tetradecahedral grains having (100) and (111) planes in one grain, grains having (100) and (110) planes in one grain, or grains having (111) and (110) planes in one grain, can be chosen and used in accordance with the purpose.

The value obtained by dividing the diameter of the projected area, which is assumed to be a circle, by the thickness of the grain, is called an aspect ratio, which defines the shape of tabular grains. Tabular grains having an aspect ratio of more than 1 can be used in the present invention. Tabular grains can be prepared by methods described, for example, by Cleav in "Photography Theory and Practice" (1930), page 131; by Gutof in "Photographic Science and Engineering", Vol. 14, pages 248 to 257 (1970); and in U.S. Pat. Nos. 4,434,226, 4,414,310, 4,433,048, and 4,439,520, and British Patent No. 2 112 157. When tabular grains are used, such merits are obtained that the covering power is increased and the color sensitization efficiency due to a sensitizing dye is increased, as described in detail in the above-mentioned U.S. Pat. No. 4,434,226. The average aspect ratio of 80% or more of all the projected areas of grains is preferably 1 or more but less than 100, more preferably 2 or more but less than 20, and particularly preferably 3 or more but less than 10. As the shape of average grains, a triangle, a hexagon, a circle, and the like can be chosen. A regular hexagonal shape having six approximately equal sides, described in U.S. Pat. No. 4,798,354, is a preferable mode.

In many cases, the grain size of tabular grains is expressed by the diameter of the projected area assumed to be a circle, and grains having an average diameter of 0.6 microns or below, as described in U.S. Pat. No. 4,748,106, are preferable, because the quality of the image is made high. An emulsion having a narrow grain size distribution, as described in U.S. Pat. No. 4,775,617, is also preferable. It is preferable to restrict the shape of tabular grains so that the thickness of the grains may be 0.5 microns or below, and more preferably 0.3 microns or below, because the sharpness is increased. Further, an emulsion in which the grains are highly uniform in thickness, with the deviation coefficient of grain thickness being 30% or below, is also preferable. Grains in which the thickness of the grains and the plane distance between twin planes are defined, as described in JP-A-63-163451, are also preferable.

In the case of tabular grains, the dislocation lines can be observed by a transmission electron microscope. In accordance with the purpose, it is preferable to choose grains having no dislocation lines, grains having several dislocation lines, or grains having many dislocation lines. Dislocation introduced straight in a special direction in the crystal orientation of grains, or curved dislocation, can be chosen, and it is possible to choose from, for example, dislocation introduced throughout grains, dislocation introduced in a particular part of grains, and dislocation introduced limitedly to the fringes of grains. In addition to the case of introduction of dislocation lines into tabular grains, also preferable is the case of introduction of dislocation lines into regular crystalline grains or irregular grains, represented by potato grains. In this case, a preferable mode is that introduction is limited to a particular part of grains, such as vertexes and edges.

The silver halide emulsion used in the present invention may be subjected to a treatment for making grains round, as disclosed, for example, in European Patent No. 96 412(B1), or it may be improved in the surface, as disclosed in West Germany Patent No. 2 306 447(C2) and JP-A-60-221320.

Generally, the grain surface has a flat structure, but it is also preferable in some cases to make the grain surface uneven intentionally. Examples are a technique in which part of crystals, for example, vertexes and the centers of planes, are formed with holes, as described in JP-A-58-106532 and JP-A-60-221320, and ruffled grains, as described in U.S. Pat. No. 4,643,966.

The grain size of the emulsion used in the present invention is evaluated, for example, by the diameter of the projected area equivalent to a circle using an electron microscope; by the diameter of the grain volume equivalent to a sphere, calculated from the projected area and the grain thickness; or by the diameter of a volume equivalent to a sphere, using the Coulter Counter method. A selection can be made from ultrafine grains having a sphere-equivalent diameter of 0.05 microns or below, and coarse grains having a sphere-equivalent diameter of 10 microns or more. Preferably, grains of 0.1 microns or more but 3 microns or below are used as photosensitive silver halide grains.

As the emulsion used in the present invention, an emulsion having a wide grain size distribution, that is, a so-called polydisperse emulsion, or an emulsion having a narrow grain size distribution, that is, a so-called monodisperse emulsion, can be chosen and used in accordance with the purpose. As the scale for representing the size distribution, the diameter of the projected area of the grain equivalent to a circle, or the deviation coefficient of the sphere-equivalent diameters, is used. If a monodisperse emulsion is used, it is good to use an emulsion having such a size distribution that the deviation coefficient is preferably 25% or below, more preferably 20% or below, and further more preferably 15% or below.

In some cases, a monodisperse emulsion is defined by the average grain size distribution based on the weight or number of grains. Further, in order to allow the photographic material to satisfy the intended gradation, in an emulsion layer having substantially the same color sensitivity, two or more monodisperse silver halide emulsions different in grain size are mixed and applied to the same layer or are applied as overlaid layers. Further, two or more polydisperse silver halide emulsions can be used as a mixture; or they can be used to form overlaid layers; or a combination of a monodisperse emulsion and a polydisperse emulsion can be used as a mixture; or the combination can be used to form overlaid layers.

As an emulsion used in the present invention, use can be made of an emulsion containing the above grains. One mode of carrying out the present invention is that the color-developing agent of the present invention and the emulsion comprising tabular grains whose silver chloride content is 50 mol % or more, are not used in combination.

As the photographic emulsion used in the present invention, any silver halide emulsion prepared by a method described, for example, by P. Glafkides in "Chemie et Phisique Photographique," Paul Montel, 1967; by G. F. Duffin in "Photographic Emulsion Chemistry," Focal Press, 1966; or by V. L. Zelikman et al. in "Making and Coating Photographic Emulsion," Focal Press, 1964, can be used. That is, any of the acid process, the neutral process, the ammonia process, and the like can be used; and to react a soluble silver salt with a soluble halogen salt, any of the single-jet method, the double-jet method, a combination thereof, and the like can be used. A method wherein grains are formed in the presence of excess silver ions (the so-called reverse precipitation process) can also be used. As one type of the double-jet method, a method wherein pAg in the liquid phase, in which a silver halide will be formed, is kept constant, that is, the so-called controlled double-jet method, can also be used. According to this method, a silver halide emulsion wherein the crystals are regular in shape and whose grain size is approximately uniform, can be obtained.

A method in which previously precipitated silver halide grains are added to a reaction vessel for the preparation of an emulsion, and the methods described, for example, in U.S. Pat. Nos. 4,334,012, 4,301,241, and 4,150,994, are preferable in some cases. These can be used as seed crystals, or they are effective when they are supplied as a silver halide for growth. In the latter case, it is preferable to add an emulsion whose grains are small in size, and as an addition method, one of the following can be chosen: all of the volume is added at one stroke, or the volume is separated and added in portions, or it is added continuously. Further, in some cases, it is also effective to add grains having different halogen compositions in order to modify the surface.

The method in which a large part or only a small part of the halogen composition of silver halide grains is converted by the halogen conversion method is disclosed, for example, in U.S. Pat. Nos. 3,477,852 and 4,142,900, European Patent Nos. 273 429 and 273 430, and West German Publication Patent No. 3 819 241, and it is an effective method for forming grains. To convert to a more hardly soluble silver salt, it is possible to add a solution of a soluble halogen or to add silver halide grains. Selection can be made from respective methods in which the conversion is made at one stroke, in several steps, and continuously.

In addition to the method in which the grain growth is made by adding a soluble silver salt and a halogen salt at constant concentrations and at constant flow rates, grain formation methods wherein the concentration is changed or the flow rate is changed, as described in British Patent No. 1 469 480 and U.S. Pat. Nos. 3,650,757 and 424,445, are preferable methods. By changing the concentration or increasing the flow rate, the amount of the silver halide to be supplied can be changed as a linear function, a quadratic function, or a more complex function, of the addition time. Further, if required, the amount of the silver halide to be supplied is decreased, which is preferable in some cases. Also effective is an addition method wherein, when several soluble silver salts different in solution composition are added, or when several soluble halogen salts different in solution composition are added, one of them is increased and the other is decreased.

A mixing vessel that is used when a solution of a soluble silver salt and a solution of a soluble halogen salt are reacted can be selected for use from methods described in U.S. Pat. Nos. 2,996,287, 3,342,605, 3,415,650, and 3,785,777, and West German Publication Patent Nos. 2 556 885 and 2 555 364.

For the purpose of promoting the ripening, a silver halide solvent is useful. For example, it is known to allow an excess amount of halide ions to be present in the reaction vessel, to promote the ripening. Further, other ripening agent can be used. All of the amount of these ripening agents may be blended in the dispersion medium in the reaction vessel before silver and halide salts are added, or their introduction into the reaction vessel may be carried out together with the addition of a halide, a silver salt, or a peptizer. As another modified mode, a method is possible wherein a ripening agent is added independently at the step of adding a halide salt and a silver salt.

For example, ammonia, thiocyanates (e.g. potassium rhodanate and ammonium rhodanate), organic thioether compounds (e.g. compounds described, for example, in U.S. Pat. Nos. 3,574,628, 3,021,215, 3,057,724, 3,038,805, 4,276,374, 4,297,439, 3,704,130, and 4,782,013, and JP-A-57-104926), thion compounds (e.g. tetra-substituted thioureas described, for example, in JP-A-53-82408 and JP-A-55-77737, and U.S. Pat. No. 4,221,863; and compounds described in JP-A-53-144319), mercapto compounds capable of promoting the growth of silver halide grains, as described in JP-A-57-202531, and amine compounds (e.g. described in JP-A-54-100717), can be mentioned.

As a protective colloid and as a binder of other hydrophilic colloid layers that are used when the emulsion according to the present invention is prepared, gelatin is used advantageously, but another hydrophilic colloid can also be used.

Use can be made of, for example, a gelatin derivative, a graft polymer of gelatin with another polymer, a protein, such as albumin and casein; a cellulose derivative, such as hydroxycellulose, carboxymethylcellulose, and cellulose sulfate; sodium alginate, a starch derivative, acacia, a saccharide derivative of a natural compound, such as a polysaccharide, including dextran and pullulan; and many synthetic hydrophilic polymers, including homopolymers and copolymers, such as a polyvinyl alcohol, a polyvinyl alcohol partial acetal, a poly-N-vinylpyrrolidone, a polyacrylic acid, a polymethacrylic acid, a polyacrylamide, a polyvinylimidazole, and a polyvinylpyrazole. Further, use can be made of a high-water-absorptive polymer described, for example, in U.S. Pat. No. 4,960,681 and JP-A-62-245, 260, that is, a copolymer of a vinyl monomer having —COOM or —$SO_3$M (wherein M represents a hydrogen atom or an alkali metal), or a copolymer of these vinyl monomers, or a copolymer of this vinyl monomer with another vinyl monomer (e.g. sodium methacrylate, ammonium methacrylate, and Sumikagel L-5H [trade name; manufactured by Sumitomo Chemical Co., Ltd.]). Two or more of these binders can be used in combination. A combination of gelatin with these binders is also preferable.

As the gelatin, one of lime-processed gelatin, acid-processed gelatin, and so-called de-ashed gelatin wherein the content of calcium or the like is reduced, can be selected, or a combination of them is also preferable. Enzyme-processed gelatin described in Bull. Soc. Sci. Photo. Japan, No. 16, page 30 (1966), may also be used, and a hydrolyzate or enzymolyzate of gelatin can also be used. For the preparation of tabular grains, it is preferable to use a low-molecular-weight gelatin described in JP-A-1-158426.

In the case of a heat-developable photographic material, an organic silver salt oxidizing agent may be used together with a photosensitive silver halide emulsion, and, as organic compounds capable of being used to form it, there are benzotriazoles described in U.S. Pat. No. 4,500,626, columns 52 to 53, aliphatic acids, and other compounds. An acetylene silver described in U.S. Pat. No. 4,775,613 is also useful. It is possible to use the organic silver salts in the form of a combination of two or more.

These organic silver salts are used in an amount of generally 0.01 to 10 mol, and preferably 0.01 to 1 mol, per mol of the photosensitive silver halide. The total coating amount of the photosensitive silver halide emulsion and the organic silver salt is generally 0.05 to 10 g/m², and more preferably 0.1 to 4 g/m², in terms of silver.

Preferably, the emulsion according to the present invention is washed with water for desalting and is dispersed in a freshly prepared protective colloid. The temperature at which the washing with water is carried out can be selected in accordance with the purpose, and preferably the temperature is selected in the range of 5 to 20° C. The pH at which the washing is carried out can be selected in accordance with the purpose, and preferably the pH is selected in the range of 2 to 10, and more preferably in the range of 3 to 8. The pAg at which the washing is carried out can be selected in accordance with the purpose, and preferably the pAg is selected in the range of 5 to 10. As a method of washing with water, one can be selected from the noodle washing method, the dialysis method using a diaphragm, the centrifugation method, the coagulation settling method, and the ion exchange method. In the case of the coagulation settling method, selection can be made from, for example, the method wherein sulfuric acid is used, the method wherein an organic solvent is used, the method wherein a water-soluble polymer is used, and the method wherein a gelatin derivative is used.

When the emulsion according to the present invention is prepared, in accordance with the purpose, it is preferable to allow a salt of a metal ion to be present, for example, at the time when grains are formed, in the step of desalting, at the time when the chemical sensitization is carried out, or before the application. When the grains are doped, the addition is preferably carried out at the time when the grains are formed; or after the formation of the grains, when the surface of the grains is modified or when the salt of a metal ion is used as a chemical sensitizer; or before the completion of the chemical sensitization. As to the doping of grains, selection can be made from a case in which the whole grains are doped, one in which only the core parts of the grains are doped, one in which only the shell parts of the grains are doped, one in which only the epitaxial parts of the grains are doped, and one in which only the substrate grains are doped. For example, Mg, Ca, Sr, Ba, Al, Sc, Y, La, Cr, Mn, Fe, Co, Ni, Cu, Zn, Ga, Ru, Rh, Pd, Re, Os, Ir, Pt, Au, Cd, Hg, Tl, In, Sn, Pb, and Bi can be used. These metals can be added if they are in the form of a salt that is soluble at the time when grains are formed, such as an ammonium salt, an acetate, a nitrate, a sulfate, a phosphate, a hydroxide, a six-coordinate complex, and a four-coordinate complex. Examples include $CdBr_2$, $CdCl_2$, $Cd(NO_3)_2$, $Pd(NO_3)_2$, $Pb(CH_3COO)_2$, $K_3[Fe(CN)_6]$, $(NH_4)_4[Fe(CN)_6]$, $K_3IrCl_6$, $(NH_4)_3RhCl_6$, and $K_4Ru(CN)_6$. As a ligand of the coordination compound, one can be selected from halo, aquo, cyano, cyanate, thiocyanate, nitrosyl, thionitrosyl, oxo, and carbonyl. With respect to these metal compounds, only one can be used, but two or more can also be used in combination.

In some cases, a method wherein a chalcogen compound is added during the preparation of the emulsion, as described in U.S. Pat. No. 3,772,031, is also useful. In addition to S, Se, and Te, a cyanate, a thiocyanate, a selenocyanate, a carbonate, a phosphate, or an acetate may be present.

The silver halide grains according to the present invention can be subjected to at least one of sulfur sensitization, selenium sensitization, tellurium sensitization (these three are called chalcogen sensitization, collectively), noble metal sensitization, and reduction sensitization, in any step of the production for the silver halide emulsion. A combination of two or more sensitizations is preferable. Various types of emulsions can be produced, depending on the steps in which the chemical sensitization is carried out. There are a type wherein chemical sensitizing nuclei are embedded in grains, a type wherein chemical sensitizing nuclei are embedded at parts near the surface of grains, and a type wherein chemical sensitizing nuclei are formed on the surface. In the emulsion according to the present invention, the location at which chemical sensitizing nuclei are situated can be selected in accordance with the purpose, and generally preferably at least one type of chemical sensitizing nucleus is formed near the surface.

Chemical sensitizations that can be carried out preferably in the present invention are chalcogen sensitization and noble metal sensitization, which may be used singly or in combination; and the chemical sensitization can be carried out by using active gelatin as described by T. H. James in "The Photographic Process," 4th edition, Macmillan, 1997, pages 67 to 76, or by using sulfur, selenium, tellurium, gold, platinum, palladium, or iridium, or a combination of these sensitizing agents, at a pAg of 5 to 10, a pH of 5 to 8, and a temperature of 30 to 80° C., as described in Research Disclosure, Item 12008 (April 1974); Research Disclosure, Item 13452 (June 1975); Research Disclosure, Item 307105 (November 1989); U.S. Pat. Nos. 2,642,361, 3,297,446, 3,772,031, 3,857,711, 3,901,714, 4,266,018, and 3,904,415, and British Patent No. 1 315 755.

In the sulfur sensitization, an unstable sulfur compound is used, and specifically, thiosulfates (e.g. hypo), thioureas (e.g. diphenylthiourea, triethylthiourea, and allylthiourea), rhodanines, mercaptos, thioamides, thiohydantoins, 4-oxooxazolidin-2-thions, di- or poly-sulfides, polythionic acids, and elemental sulfur, and known sulfur-containing compounds described in U.S. Pat. Nos. 3,857,711, 4,266, 018, and 4,054,457, can be used. In many cases, sulfur sensitization is used in combination with noble metal sensitization.

A preferable amount of a sulfur sensitizing agent used for the silver halide grains accrding to the present invention is $1 \times 10^{-7}$ to $1 \times 10^{-3}$ mol, and more preferably $5 \times 10^{-7}$ to $1 \times 10^{-4}$ mol, per mol of the silver halide.

In the selenium sensitization, known unstable selenium compounds are used, such as those described, for example, in U.S. Pat. Nos. 3,297,446 and 3,297,447, specific such selenium compounds are colloidal metal selenium, selenoureas (e.g. N,N-dimethylselenourea and tetramethylselenourea), selenoketones (e.g. selenoacetone), selenoamides (e.g. selenoacetamide), selenocarboxylic acids and esters, isoselenocyanates, selenides (e.g. diethylselenides and triphenylphosphine selenide), and selenophosphates (e.g. tri-p-tolylselenophosphate). In some cases, preferably the selenium sensitization is used in combination with one or both of sulfur sensitization and noble metal sensitization.

The amount of the selenium sensitizing agent to be used varies depending on the selenium compound, the silver halide grains, the chemical ripening conditions, and the like that are used, and the amount is generally of the order of $10^{-8}$ to $10^{-4}$ mol, and preferably $10^{-7}$ to $10^{-5}$ mol, per mol of the silver halide.

As the tellurium sensitizing agent used in the present invention, compounds described in Canadian Patent No. 800 958, British Patent Nos. 1 295 462 and 1 396 696, and JP-A-2-333819 and 3-131598 can be used, and specific tellurium sensitizing agents include colloidal tellurium, telluroureas (e.g. tetramethyltellurourea, N-carboxylethyl-N', N'-dimethyltellurourea, and N,N'-dimethylethylenetellurourea), isotellurocyanates, telluroketones, telluroamides, tellurohydrazides, telluroesters, phosphine tellurides (e.g. tributylphosphine telluride and butylisopropylphosphine telluride), and other tellurium compounds (e.g. potassium tellurocyanate and sodium telluropentathionate).

The amount of the tellurium sensitizing agent to be used is of the order of generally $10^{-7}$ to $5 \times 10^{-2}$ mol, and more preferably $5 \times 10^{-7}$ to $10^{-3}$ mol, per mol of the silver halide.

In the noble metal sensitization, a salt of a noble metal, such as platinum, gold, palladium, and iridium, can be used, and specifically gold sensitization, palladium sensitization, and a combination thereof are particularly preferable. In the case of gold sensitization, a known compound, such as chloroauric acid, potassium chloroaurate, potassium auriothiocyanate, gold sulfide, and gold selenide, can be used. The palladium compound means salts of divalent or tetravalent palladium salt. A preferable palladium compound is represented by $R_2PdX_6$ or $R_2PdX_4$, wherein R represents a hydrogen atom, an alkali metal atom, or an ammonium radical; and X represents a halogen atom, i.e. a chlorine atom, a bromine atom, or an iodine atom.

Specifically, $K_2PdCl_4$, $(NH_4)_2PdCl_6$, $NaPdCl_4$, $(NH_4)_2PdCl_4$, $Li_2PdCl_4$, $Na_2PdCl_6$, or $K_2PdBr_4$ is preferable. Preferably a gold compound and a palladium compound are used in combination with a thiocyanate or a selenocyanate.

Preferably the emulsion according to the present invention is used in combination with gold sensitization. A preferable amount of the gold sensitizing agent is $1 \times 10^{-7}$ to $1 \times 10^{-3}$ mol, and more preferably $5 \times 10^{-7}$ to $5 \times 10^{-4}$ mol, per mol of the silver halide. A preferable amount of the palladium compound is in the range of $5 \times 10^{-7}$ to $1 \times 10^{-3}$ mol. A preferable amount of the thiocyan compound and the selenocyan compound is in the range of $1 \times 10^{-6}$ to $5 \times 10^{-2}$ mol.

Preferably that the silver halide emulsion according to the present invention is subjected to reduction sensitization during the formation of the grains, after the formation of the grains but before the chemical sensitization, or during or after the chemical sensitization.

Herein, the reduction sensitization can be selected from a method wherein a reduction sensitizer is added to a silver halide emulsion; a method called silver ripening, wherein the growth or ripening is made in an atmosphere having a pAg as low as 1 to 7; and a method called high-pH ripening, wherein the growth or ripening is made in an atmosphere having a pH as high as 8 to 11. Two or more methods can also be used in combination.

The method wherein a reduction sensitizer is added is preferable, because the level of reduction sensitization can be adjusted subtly.

As the reduction sensitizer, known reduction sensitizers can be selected and used, such as stannous salts, ascorbic acid and its derivatives, amines and polyamines, hydrazine and its derivatives, formamidinesufinic acid, silane compounds, and boran compounds; and two or more compounds can be used in combination. As the reduction sensitizer, preferable compounds are stannous chloride, aminoiminomethanesulfinic acid (popularly called thiourea dioxide), dimethylamineboran, and ascorbic acid and its derivatives. Since the amount of the reduction sensitizer to be added depends on the conditions of the production of the emulsion, the amount must be selected, but preferably it is in the range of $10^{-7}$ to $10^{-3}$ mol per mol of the silver halide.

The chemical sensitization can be carried out in the presence of a so-called chemical sensitization auxiliary. As a useful chemical sensitization auxiliary, a compound is used that is known to suppress fogging and to increase the sensitivity in the process of chemical sensitization, such as azaindene, azapyridazine, and azapyrimidine. Examples of chemical sensitization auxiliary improvers are described in U.S. Pat. Nos. 2,131,038, 3,411,914, and 3,554,757, JP-A-58-126526, and by G. F. Duffin in "Photographic Emulsion Chemistry" mentioned above, pages 138 to 143.

Preferably, an oxidizing agent for silver is added during the process of the production of the emulsion according to the present invention. The oxidizing agent for silver refers to a compound that acts on metal silver to convert it to silver ions. Particularly useful is a compound that converts quite fine silver grains, which are concomitantly produced during the formation of silver halide grains and during the chemical sensitization, to silver ions. The thus produced silver ions may form a silver salt that is hardly soluble in water, such as a silver halide, silver sulfide, and silver selenide, or they may form a silver salt that is readily soluble in water, such as silver nitrate. The oxidizing agent for silver may be inorganic or organic. Example inorganic oxidizing agents include ozone, hydrogen peroxide and its adducts (e.g. $NaBO_2$, $H_2O_2 \cdot H_2O$, $2NaCO_3 \cdot H_2O_2$, $Na_4P_2O_7 \cdot H_2O_2$, and $2NaSO_4 \cdot H_2O_2 \cdot 2H_2O$); oxygen acid salts, such as peroxyacid salts (e.g. $K_2S_2O_8$, $K_2C_2O_6$, and $K_2P_2O_8$), peroxycomplex compounds (e.g. $K_2[Ti(O_2)C_2O_4] \cdot 3H_2O$, $4K_2SO_4 \cdot Ti(O_2)OH \cdot SO_4 \cdot 2H_2O$, and $Na_3[VO(O_2)(C_2O_4)_2] \cdot 6H_2O$), permanganates (e.g. $KMnO_4$), and chromates (e.g. $K_2CrO_7$); halogen elements, such as iodine and bromine; perhalates (e.g. potassium periodate), salts of metals having higher valences (e.g. potassium hexacyanoferrate(III), and thiosulfonates.

Examples of the organic oxidizing agents include quinones, such as p-quinone; organic peroxides, such as peracetic acid and perbenzoic acid; and compounds that can release active halogen (e.g. N-bromosuccinimido, chloramine T, and chloramine B).

Preferable oxidizing agents used in the present invention are such inorganic oxidizing agents as ozone, hydrogen peroxide and its adducts, halogen elements, and thiosulfonates, and such organic oxidizing agents as quinones. Use of a combination of the above reduction sensitization with the oxidizing agent for silver is a preferable mode. Use is made of one selected from a method wherein after an oxidizing agent is used, reduction sensitization is carried out; a method wherein after reduction sensitization is carried out, an oxidizing agent is used; and a method wherein an oxidizing agent and a reduction sensitizer are present simultaneously. These methods can be used in the step of forming grains or in the step of chemical sensitization, which step will be chosen.

In the photographic emulsion used in the present invention, various compounds can be incorporated for the purpose of preventing fogging during the process of the production of the photographic material, during the storage of the photographic material, or during the photographic processing, or for the purpose of stabilizing the photographic performance. That is, compounds known as antifoggants or stabilizers can be added, such as thiazoles including benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly 1-phenyl-5-mercaptotetrazole), mercaptopyrimidine, mercaptotriazine; thioketo compounds, such as oxazolinthione; and azaindenes, such as triazaindenes; tetraazaindenes (particularly 4-hydroxy-6-methyl-1,3,3a,7-tetraazaindenes), and pentaazaindenes. For examples, those described in U.S. Pat. Nos. 3,954,474 and 3,982,947, and JP-B-62-28660, can be used. A preferable compound is a compound described in Japanese Patent Application No. 62-47225. In accordance with the purpose, the antifoggant and the stabilizer can be added at various times, for example, before the formation of the grains, during the formation of the grains, after the formation of the grains, in the step of washing with water, at the time of dispersion after the washing with water, before the chemical sensitization, during the chemical sensitization, after the chemical sensitization, and before the application. In addition to the case wherein the antifoggant and the stabilizer are added during the preparation of the emulsion, so that the antifogging effect and the stabilizing effect, which are their essential effects, may be achieved, they can be used for various other purposes, for example, for controlling the habit of the crystals of the grains, for making the grain size small, for reducing the solubility of the grains, for controlling the chemical sensitization, and for controlling the arrangement of the dyes.

When the photosensitive silver halide used in the present invention is made to have color sensitivities of green sensitivity, red sensitivity, and infrared sensitivity, the photosensitive silver halide emulsion is spectrally sensitized with methine dyes or the like. If required, the blue-sensitive emulsion may be spectrally sensitized in the blue region.

Dyes that can be used include a cyanine dye, a merocyanine dye, a composite cyanin dye, a composite merocyanine dye, a halopolar cyanine dye, a hemicyanine dye, a styryl dye, and a hemioxonol dye. Particularly useful dyes are those belonging to a cyanine dye, a merocyanine dye, and a composite merocyanine dye. In these dyes, any of nuclei generally used in cyanine dyes as base heterocyclic ring nuclei can be applied. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, and a pyridine nucleus; and a nucleus formed by fusing an cycloaliphatic hydrocarbon ring or an aromatic hydrocarbon ring to these nuclei, that is, 5- to 6-heterocyclic ring nuclei, such as an indolenine nucleus, a benzindolenine nucleus, an indole nucleus, a benzoxazole nucleus, a naphthooxazole nucleus, a benzothiazole nucleus, a naphthothiazole nucleus, a benzoselenazole nucleus, a benzimidazole nucleus, a rhodanine nucleus, and a thiobarbituric acid nucleus, can be applied. These nuclei may be substituted on the carbon atom. Specifically, sensitizing dyes described, for example, in U.S. Pat. No. 4,617,257 and JP-A-59-180550, JP-A-64-13546, JP-A-5-45828, and JP-A-5-45834 can be mentioned. In addition, specific examples include thermally decolorant sensitizing dyes described in JP-A-59-180550, JP-A-60-140335 and Journal of Research & Disclosure, the June issue, pp12–13 (1978) (RD-17029).

In the merocyanine dye or the composite merocyanine dye, as a nucleus having a ketomethylene structure, a 5- to 6-membered heterocyclic ring nucleus, such as a pyrazolin-5-one nucleus, a thiohydantoine nucleus, a 2-thiooxazolidin-2,4-dione nucleus, a thiazolidin-2,4-dione nucleus, a rhodanine nucleus, and a thiobarbituric acid nucleus, can be applied.

These dyes can be used singly or in combination, and a combination of these sensitizing dyes is often used, particularly for the purpose of adjusting the wavelength of the spectral sensitivity, and for the purpose of supersensitization. Typical examples thereof are described in U.S. Pat. Nos. 2,688,545, 3,397,060, 2,977,229, 3,522,052, 3,527,64, 3,617,293, 3,628,964, 3,672,989, 3,679,428, 3,703,377, 3,769,301, 3,814,609, 3,837,862, and 4,026,707, British Patent Nos. 1 344 218 and 1 507 803, JP-B-43-4936, JP-B-53-12375, JP-A-52-110618 and JP-A- 52-109925.

Together with the sensitizing dye, a dye having no spectral sensitizing action itself, or a compound that does not substantially absorb visible light and that exhibits supersensitization, may be included in the emulsion (e.g. those described, for example, in U.S. Pat. No. 3,615,641 and JP-A-63-23145).

The time when these sensitizing dyes are added to the emulsion may be at any stage of the preparation of the emulsion that is known to be useful.

Most usually, the sensitizing dye is added at a time after the completion of chemical sensitization but before the application, but the sensitizing dye may be added at the same time as the addition of the chemical sensitizer, to carry out spectral sensitization and chemical sensitization simultaneously, as described in U.S. Pat. Nos. 3,628,969 and 4,225,666, or the sensitizing dye may be added before the chemical sensitization, as described in JP-A-58-113928. Further, the sensitizing dye may be added before the completion of the precipitation of the silver halide grains, to start the spectral sensitization. Further, the sensitizing dye may be added before or after the formation of nuclei of the silver halide grains, in accordance with U.S. Pat. Nos. 4,183,756 and 4,225,666, or it may be added in portions, such that part of the sensitizing dye is added before the chemical sensitization, and the rest is added after the chemical sensitization.

Further, these sensitizing dyes and supersensitizing dyes may be added in the form of a solution of an organic solvent, such as methanol, or in the form of a dispersion of gelatin, or in the form of a solution of a surface-active agent.

Generally the amount of the sensitizing dye to be added is of the order of $4 \times 10^{-6}$ to $8 \times 10^{-3}$ mol per mol of the silver halide, but when the silver halide grain size is 0.2 to 1.2 $\mu$m, which is more preferable, the amount of the sensitizing dye to be added is more effectively about $5 \times 10^{-5}$ to $2 \times 10^{-3}$ mol per mol of the silver halide.

To the photographic material related to the present technique, may be added the above-mentioned various additives, and also other various additives in accordance with the purpose.

These additives are described in more detail in Research Disclosure, Item 17643 (December 1978); Research Disclosure, Item 18176 (November 1979); and Research Disclosure, Item 307105 (November 1989), and the particular parts are given below in a Table.

| Additive | RD 17643 | RD 18716 | Rd 307105 |
| --- | --- | --- | --- |
| 1 Chemical sensitizers | p. 23 | p. 648 (right column) | p. 996 |
| 2 Sensitivity-enhancing agents | — | p. 648 (right column) | — |
| 3 Spectral sensitizers and Supersensitizers | pp. 23–24 | pp. 648 (right column)-649 (right column) | pp. 996–998 |
| 4 Brightening agents | p. 24 | pp. 647 (right column) | p. 998 |
| 5 Light absorbers, Filter dyes, and UV Absorbers | pp. 25–26 | pp. 649 (right column)-650 (left column) | p. 1003 |
| 6 Binders | p. 26 | p. 651 | pp. 1003–1004 |

| Additive | RD 17643 | RD 18716 | Rd 307105 |
|---|---|---|---|
| 7 Plasticizers and Lubricants | p. 27 | p. 650 | p. 1006 |
| 8 Coating aids and Surfactants | pp. 26–27 | p. 650 | pp. 1005 (left)-1006 (right) |
| 9 Antistatic agents | p. 27 | p. 650 (right column) | pp. 1006–1007 |
| 10 Antifogging agents and Stabilizers | pp. 24–25 | p.649 | pp. 998–1000 |
| 11 Anti-staining agents | p. 25 (right column) | p. 650 (left to right) | |
| 12 Image-dye stabilizers | p. 25 | | |
| 13 Hardeners | p. 26 | p. 651 (left column) | pp. 1004 (right)-1005 (left) |

In addition to the above hardeners, other hardeners are described, for example, in U.S. Pat. No. 4,678,739, 41st column; U.S. Pat. No. 4,791,042, and JP-A-59-116655, 62-245261, 61-18942, and 4-218044. More specifically, aldehyde hardeners (e.g. formaldehyde), aziridine hardeners, epoxy hardeners, vinyl sulfone hardeners (e.g. N,N'-ethylene-bis(vinylsulfonylacetamide)ethane), N-methylol hardeners (e.g. dimethylol urea), or polymer hardeners (e.g. compounds described, for example, in JP-A-62-234157) can be mentioned.

These hardeners are used in an amount of 0.001 to 1 g, and preferably 0.005 to 0.5 g, per g of the coated gelatin. The layer into which the hardeners are added may be any of layers that constitute the photographic material (another name, a photographic element) or the dye-fixing material (another name, a dye-fixing element or an image receiving element), or the hardener may be divided into two or more parts, which are added into two or more layers.

In the photographic material of the present invention, a matting agent can be used for the purpose of adhesion prevention, improvement of slipping property, matting, etc. Example matting agents icnclude silicon dioxide, polyolefins, polymethacrylates, and the like described in JP-A-61-88256, page 29, as well as compounds, including benzoguanamine resin beads, polycarbonate resin beads, ABS resin beads, and the like, described in JP-A-63-274944 and 63-274952. Other matting agents described in the above RD can be used. These matting agents are added into the uppermost layer (protective layer), and also into a lower layer if required.

Further, the constitutional layers of a heat-developable photographic material may contain a heat solvent, an antifoaming agent, a germ-proofing agent, a mildew-proofing agent, colloidal silica, etc. Specific examples of these additives are described, for example, in JP-A-61-88256, pages 26 to 32; JP-A-3-11338, and JP-B-51-51496.

In the constitutional layers of the photographic material of the present invention, use can be made of various surface-active agents for various purposes of, for example, serving as a coating aid, improving releasability and slipping property, preventing electrification, or promoting development. Specific examples of the surface-active agents are described, for example, in the above Research Disclosures and JP-A-62-173463 and 62-183457. In the case of a heat-developable photographic material, also preferably an organofluoro compound is contained in the constitutional layer, for example, for the purposes of improving slipping properties, preventing electrification, and improving releasability. Typical examples of the organofluoro compound are hydrophobic fluoro compounds, including solid fluoro compound resins, such as ethylene tetrafluoride resins; oily fluoro compounds, including fluoro oils; or fluorine-containing surface-active agents described, for example, in JP-B-57-9053, 8th column to the 17th column, and JP-A-61-20944 and 62-135836.

In the photographic material of the present invention, known antifading agents can be used. Example organic antifading agents include hydroquinones, 5-hydroxychromans, 5-hydroxycoumarans, paraalkoxyphenols, hindered phenols, including bisphenols; gallic acid derivatives, methylenedioxybenzenes, aminophenols, hindered amines, and ether or ester derivatives produced by silylating or alkylating the phenolic hydroxyl group of these compounds. Further, metal complexes, represented by (bissalicylaldoximato)nickel complex and (bis-N,N-dialyldithiocarbamato)nickel complex, can also be used.

To prevent a yellow dye image from being deteriorated by heat, humidity, and light, the addition of a compound having both the structures of a hindered amine and a hindered phenol in the same molecule, as described in U.S. Pat. No. 4,268,593, gives a good result. Further, to prevent a magenta dye image from being deteriorated particularly by light, spiroindanes described in JP-A-56-159644, and chromans substituted with a hydroquinone diether or monoether, described in JP-A-55-89835, give a good result.

In the constitutional layers of the photographic material of the present invention, various antifoggants or photographic stabilizers and their precursors can be used. Specific examples thereof are compounds described, for example, in the above-mentioned Research Disclosures, U.S. Pat. Nos. 5,089,378, 4,500,627, and 4,614,702, JP-A-64-13546 (pages 7 to 9, 57 to 71, and 81 to 97), U.S. Pat. Nos. 4,775,610, 4,626,500, and 4,983,494, JP-A-62-174747, 62-239148, 63-264747, 1-150135, 2-110557, and 2-178650, and Research Disclosure No. 17 643 (1978), pages 24 to 25.

These compounds are preferably used in an amount of $5 \times 10^{-6}$ to $1 \times 10^{-1}$ mol, and more preferably $1 \times 10^{-5} \times 1 \times 10^{-2}$ mol, per mol of silver.

Suitable bases that can be used in the present invention include a synthetic plastic film, for example, made of polyolefins, such as polyethylenes and polypropylenes, polycarbonates, cellulose acetates, polyethylene terephthalates, polyethylene naphthalates, and polyvinyl chlorides; a paper base, for example, made of photographic base paper, printing paper, baryta paper, and resin-coated paper; a base formed by providing the above plastic film with a reflective layer; and a base described in JP-A-62-253159, pages 29 to 31.

Those described in the above Research Disclosure No. 17643, page 28; Research Disclosure No. 18716, page 647, right column, to page 648, left column; and Research Disclosure No. 307105, page 879, are preferably used. These bases may be subjected to heat treatment at or below Tg, as described in U.S. Pat. No. 4,141,735, so that they may be hardly core-set. The surface of the bases may be surface-treated, to improve the adhesion between the base and the emulsion undercoat layer. In the present invention, the surface treatment can be carried out by glow discharge treatment, ultraviolet-ray-irradiation treatment, corona treatment, or flame treatment.

Further, bases described in Kochi Gijutsu No. 5 (published by Azutekku Yugen-kaisha, Mar., 22, 1991), pages 44 to 149, can also be used.

Transparent bases made, for example, of polyethylenedinaphthalene dicarboxylates, and bases produced by coating these transparent bases with a transparent magnetic product, can also be used.

In a heat-developable photographic material, in order to obtain a constant image all the time against changes in the processing temperature and the processing time at the time of development, various development inhibitors can be used. Herein, the term "a development inhibitor" means a compound that neutralizes bases quickly or reacts quickly with bases after suitable development, to lower the base concentration in the film, to stop the development; or a compound that interacts with silver and silver salts, to inhibit the development. Specific examples include acid precursors that release an acid when heated, electrophilic compounds that undergo a substitution reaction with coexisting bases when heated, nitrogen-containing heterocyclic compounds, mercapto compounds, and their precursors. Details are described in JP-A-62-253159, pages 31 to 32.

When the photographic material of the present invention is used as a heat-developable photographic material, to supply a base, a method wherein a base is generated from a base precursor, is preferable.

Preferable base precursors used in the present invention include a salt of a base with an organic acid that is decarboxylated when heated; a compound that is decomposed by such a reaction as an intramolecular nucleophilic substitution reaction, Lossen rearrangement, or Beckmann rearrangement, to release amines; a compound that undergoes some reaction when heated, to release a base; and a compound that undergoes hydrolysis or a complex formation reaction, to generate a base. Examples of the above base precursor that generates a base when heated include bases of trichloroacetic acid described, for example, in British Patent No. 998 959; bases of α-sulfonylacetic acid that are further improved in stability, as described in U.S. Pat. No. 4,060,420; bases of propiolic acid described in Japanese Patent Application No. 58-55700; 2-carboxycarbodiamide derivatives described in U.S. Pat. No. 4,088,496; salts of heat-decomposable acids that are formed using, in addition to an organic base, an alkali metal or an alkali earth metal (Japanese Patent Application No. 58-69597); hydroxamcarbamates that use Lossen rearrangement, as described in Japanese Patent Application No. 58-43860; and aldoxime-carbamates that produce nitrile when heated, as described in Japanese Patent Application No. 58-31614.

Also useful are base precursors described, for example, in British Patent Nos. 998 945 and 2 079 480, JP-A-50-226225, U.S. Pat. Nos. 3,220,846, 4,514,493, and 4,657,848, and Kochi Gijutsu No. 5 (published by Azutekku Yugen-kaisha, Mar. 22, 1991), pages 55 to 86.

Examples methods of exposing the photographic material of the present invention with light and recording the image, include a method wherein a landscape, a man, or the like is directly photographed by a camera or the like; a method wherein a reversal film or a negative film is exposed to light using, for example, a printer, or an enlarging apparatus; a method wherein an original picture is subjected to scanning exposure through a slit by using an exposure system of a copying machine or the like; a method wherein light-emitting diodes and various lasers (e.g. laser diodes and gas lasers) are allowed to emit light, to carry out scanning exposure through image information and electrical signals (methods described, for example, in JP-A-2-129625 and Japanese Patent Application Nos. 3-338182, 4-9388, and 4-281442); and a method wherein image information is outputted to an image display apparatus, such as a CRT, a liquid crystal display, an electroluminescence display, and a plasma display, and exposure is carried out directly or through an optical system.

Light sources that can be used for recording an image on the photographic material, as mentioned above, include natural light and light sources and exposure methods described in U.S. Pat. No. 4,500,626, 56th column, and JP-A-2-53378 and 2-54672, such as a tungsten lamp, a light-emitting diode, a laser light source, and a CRT light source.

Image-wise exposure can be carried out by using a wavelength-converting element that uses a nonlinear optical material and a coherent light source, such as laser rays, in combination. Herein the term "nonlinear optical material" refers to a material that can develop nonlinearity of the electric field and the polarization that appears when subjected to a strong photoelectric field, such as laser rays, and inorganic compounds, represented by lithium niobate, potassium dihydrogenphosphate (KDP), lithium iodate, and $BaB_2O_4$; urea derivatives, nitroaniline derivatives, nitropyridine-N-oxide derivatives, such as 3-methyl-4-nitropyridine-N-oxide (POM); and compounds described in JP-A-61-53462 and 62-210432 can be preferably used. As the form of the wavelength-converting element, for example, a single crystal optical waveguide type and a fiber type are known, both of which are useful.

The above image information can employ, for example, image signals obtained from video cameras, electronic still cameras, and the like; television signals, represented by Nippon Television Singo Kikaku (NTSC); image signals obtained by dividing an original picture into a number of picture elements by a scanner or the like; and an image produced by a computer, represented by CG or CAD.

The color-developing agent of the present invention can be used for all silver halide photographic materials, including color negatives, color papers, X-ray photographic materials and photomechanical reproduction materials for color instant photography and color reversal, and X-ray photographic materials and reproduction photographic materials for forming color images. Further, the color-developing agent of the present invention can be added into a silver halide photographic material, and also into a processing solution. The color-developing agent for use in the present invention is contained in at least one hydrophilic colloid layer provided on a support, when it is used in a silver halide light-sensitive material. As a silver halide light-sensitive material containing a color-developing agent for use in the present invention, a color diffusion transfer silver halide photographic light-sensitive material is preferable.

If the color-developing agent for use in the present invention is added into a silver halide photographic material, the development can be carried out by heating treatment or activator treatment.

The heating treatment of photographic materials is known in the art, and heat-developable photographic materials and the process thereof are described, for example, in "Shashin Kogaku no Kiso" (published by Corona-sha, 1979), pages 553 to 555; "Eizo Joho" (published April 1978), page 40; "Nebletts Handbook of Photography and Reprography," 7th edition (Van Nostrand and Reinhold Company), pages 32 to 33; U.S. Pat. Nos. 3,152,904, 3,301,678, 3,392,020, and 3,457,075, British Patent Nos. 1 131 108 and 1 167 777, and Research Disclosure (June 1978), pages 9 to 15 (RD-17029).

The activator treatment refers to a treatment wherein a color developing agent is built in a photographic material and the photographic material is developed with a processing solution free from any color-developing agent. In this case, the processing solution is characterized in that it does not contain a color-developing agent, which is normally contained as a development processing solution component, but the processing solution may contain other components (e.g. an alkali and an auxiliary developing agent). Examples of the activator treatment are shown in known publications, such as European Patent Nos. 545 491(A1) and 565 165 (A1).

In the present invention, the term "a developing solution" means a processing solution containing a color-developing agent or a processing solution not containing a developing agent (for activator).

Processing materials and processing methods used in the case of the activator treatment in the present invention will now be described in detail. In the present invention, the photographic material is developed (silver development/ cross oxidation of the built-in color-developing agent), desilvered, washed with water, and stabilized. In some cases, after the washing with water or the stabilizing processing, a treatment of alkalinization for color formation intensification (alkali treatment) is carried out.

When the photographic material of the present invention is developed with a developing solution, preferably the developing solution contains a compound that functions as a developing agent of silver halides and/or allows the developing agent oxidation product resulting from the silver development to cross-oxidize the color-developing agent built in the photographic material (auxiliary developing agent). Preferably, pyrazolidones, dihydroxybenzenes, reductones, and aminophenols are used, and particularly preferably pyrazolidones are used.

Among pyrazolidones, 1-phenyl-3-pyrazolidones are preferable, and they include 1-phenyl-3-pyrazolidone, 1-phenyl-4,4-dimethyl-3-pyrazolidone, 1-phenyl-4-methyl-4-hydroxylmethyl-3-pyrazolidone, 1-phenyl-4,4-dihydroxydimethyl-3-pyrazolidone, 1-phenyl-5-methyl-3-pyrazolidone, 1-phenyl-5-phenyl-3-pyrazolidone, 1-p-tolyl-4-methyl-4-hydroxymethyl-3-pyrazolidone, 1-p-chlorophenyl-4-methyl-4-hydroxymethyl-3-pyrazolidone, 1-phenyl- 2-hydroxymethyl-4,4-dimethyl-3-pyrazolidone, 1-phenyl-2-acetyl-3-pyrazolidone, 1-phenyl-2-hydroxymethyl-5-phenyl-3-pyrazolidone, and 1-(2-chlorophenyl)-4-hydroxymethyl-4-methyl-3-pyrazolidone.

Dihydroxybenzenes include hydroquinone, chlorohydroquinone, bromohydroquinone, isopropylhydroquinone, methylhydroquinone, 2,3-dichlorohydroquinone, 2,5-dichlorohydroquinone, 2,5-dimethylhydroquinone, and potassium hydroquinonemonosulfonate.

Reductones include N-methyl-p-aminophenol, N-(β-hydroxyethyl)-p-aminophenol, N(4-hydroxyphenyl)glycine, and 2-methyl-p-aminophenol.

Although these compounds are generally used singly, use of two or more of them in combination is also preferable, to enhance the development and cross oxidation activity.

The amount of these compounds to be used in the developing solution is generally $2.5 \times 10^{-4}$ to 0.2 mol/liter, preferably 0.0025 to 0.1 mol/liter, and more preferably 0.001 to 0.05 mol/liter.

Example preservatives for use in the developing solution according to the present invention include sodium sulfite, potassium sulfite, lithium sulfite, formaldehyde sodium bisulfite, and hydroxylamine sulfate, which are preferably used in an amount in the range of 0.1 mol/liter or below, and more preferably 0.001 to 0.02 mol/liter. If a high-silver-chloride emulsion is used in the photographic material, the above compound is used in an amount of generally 0.001 mol/liter or below, and preferably it is not used at all in some cases.

In the present invention, instead of the above hydroxylamine or sulfite ions, an organic preservative can be preferably used.

Herein the term "organic preservatives" refers generally to organic compounds that reduce the deterioration speed of the above developing agent when added to the developing solution. That is, organic preservatives are organic compounds that have a function of preventing developing agents from being oxidized with air or the like; and particularly effective organic preservatives are other hydroxylamine derivatives (excluding hydroxylamine), hydroxamic acids, hydrazines, phenols, α-hydroxyketones, α-aminoketones, saccharides, monoamines, diamines, polyamines, quaternary ammoniums, nitroxy radicals, alcohols, oximes, diamide compounds, and fused-ring-type amines. These are described, for example, in JP-A-63-4235, 63-5341, 63-30845, 63-21647, 63-44655, 63-46454, 63-53551, 63-43140, 63-56654, 63-58346, 63-43138, 63-146041, 63-44657, and 63-44656, U.S. Pat. Nos. 3,615,503 and 2,494,903, and JP-B-48-30496. Further, other reservatives that may be contained, if required, include, for example, various metals described in JP-A-57-44148 and 57-53749, salicylic acids described in JP-A-59-180588, alkanolamines described in JP-A-54-3532, polyethyleneamines described in JP-A-61-94349, and aromatic polyhydroxy compounds described in U.S. Pat. No. 3,746,544. In particular, preferably contained are alkanolamines described in JP-A-4-97355, pages 631 to 632, and dialkylhydroxylamines described therein, pages 627 to 630. Further, it is also preferable to use a combination of dialkylhydroxylamines and/or hydrazine derivatives with alkanolamines, or a combination of α-amino acids, represented by glycine, with dialkylhydroxylamines, as described in European Patent No. 530 921(A1).

These compounds are preferably used in an amount of $1 \times 10^{-3}$ to $5 \times 10^{-1}$ mol, and more preferably $1 \times 10^{-2}$ to $2 \times 10^{-1}$ mol, per liter of the developing solution.

In the present invention, the developing solution contains halide ions, such as chloride ions, bromide ions, and iodide ions. Preferably, when a high silver-chloride emulsion is used, chloride ions are contained in an amount of $3.5 \times 10^{-3}$ to $3.0 \times 10^{-1}$ mol/liter, and more preferably $1 \times 10^{-2}$ to $2 \times 10^{-1}$ mol/liter, and/or bromide ions in an amount of $0.5 \times 10^{-5}$ to $1.0 \times 10^{-3}$ mol/liter, and more preferably $3.0 \times 10^{-5}$ to $5 \times 10^{-4}$ mol/liter.

Herein the halide ions may be added directly to the developing solution, or they may be dissolved out from the photographic material into the developing solution during the development processing.

If the halide ions are added to the developing solution, the halide ion source may be a sodium salt, a potassium salt, an ammonium salt, a lithium salt, or a magnesium salt, of the halide ion.

When the halide ions are dissolved out from the light-sensitive material, the halide ions are supplied mainly from the silver halide emulsion, but they may also be supplied from some other source.

The developing solution used in the present invention preferably has a pH of 8 to 13, and more preferably 9 to 12.

To retain the above pH, it is preferable to use various buffers, examples of which are carbonates, phosphates, brorates, tetraborates, hydroxybenzoates, glycinates, N,N-dimethylglycinates, leucinates, norleucinates, guaninates, 3,4-dihydroxyphenylalaninates, alaninates, aminobutylates, 2-amino-2-methyl-1,3-propandiol salts, valerates, prolinates, trishydroxylaminomethane salts, and lysinates. In particular, carbonates, phosphates, tetraborates, and hydroxybenzoates are excellent in solubility and buffering function at a pH in the range of 9.0 or over, and when they are added to the developing solution, the photographic performance is not adversely affected, so that they are preferably used.

Specific examples of these buffers are lithium carbonate, sodium carbonate, potassium carbonate, potassium bicarbonate, tripotassium phosphate, trisodium phosphate, dipotassium phosphate, disodium phosphate, potassium borate, sodium borate, sodium tetraborate, potassium tetraborate, sodium o-hydroxybenzoate (sodium salicylate), and potassium 5-sulfo-2-hydroxybenzoate (potassium 5-sulfosalicylate).

The amount of the buffers to be added to the developing solution is preferably 0.05 mol/liter or over, and particularly preferably 0.1 to 0.4 mol/liter.

In addition, in the developing solution, as a sediment-preventive agent against calcium and magnesium, or as an agent for stabilizing the developing solution, various chelating agents can be used. Examples are nitrilotriacetic acid, diethylenetriaminepentaacetic acid, ethylenediaminetetraacetic acid, N,N,N-trimethylenephosphonic acid, ethylenediamine-N,N,N',N'-tetramethylenesulfonic acid, 1,2-diaminopropanetetraacetic acid, glycol ether diaminetetraacetic acid, ethylenediamine orthohydroxyphenylacetic acid, 2-phosphonobutane-1,2,4-tricarboxylic acid, 1-hydroxyethylidene-1,1-diphosphonic acid, and 1,2-dihydroxybenzene-4,6-disulfonic acid, and their alkali metal salts. Two or more of these chelating agents may be used in combination, if necessary.

With respect to the amount of these chelating agents to be added, preferably the amount is enough to sequester the metal ions in the developing solution, and, for example, these chelating agents are used in an amount in the order of 0.1 to 10 g per liter.

In the present invention, if required, an arbitrary antifoggant can be added. As the antifoggant, nitrogen-containing heterocyclic compounds, and alkali metal halide, such as sodium chloride, potassium bromide, and potassium iodide, are used. Typical examples of the nitrogen-containing heterocyclic compounds are benzotriazole, 5-nitrobenzotriazole, 5-methylbenzotriazole, 5-nitrobenzimidazole, 5-nitroindazole, 2-thiazolylbenzimidazole, indazole, hydroxyazaindolizine, adenine, and 1-phenyl-5-mercaptotetrazole, or their derivatives.

The amount of the nitrogen-containing heterocyclic compounds to be added is $1 \times 10^{-5}$ to $1 \times 10^{-2}$ mol/liter, and preferably $2.5 \times 10^{-5}$ to $1 \times 10^{-3}$ mol/liter.

In the developing solution, if necessary, an arbitrary development accelerator can be added, examples of which are the following compounds: thioether compounds described, for example, in JP-B-37-16088, 37-5987, 38-7826, 44-12380, and 45-9019, and U.S. Pat. No. 3,813,247; p-phenylenediamine compounds described in JP-A-52-49829 and 50-15554; quaternary ammonium salts described, for example, in JP-A-50-137726, JP-B-44-30074, and JP-A-56-156826 and 52-43429; amine compounds described, for example, in U.S. Pat. Nos. 2,494,903, 3,128,182, 4,230,796, and 3,253,919, JP-B-41-11431, and U.S. Pat. Nos. 2,482, 546, 2,596,926, and 3,582,346; and imidazoles and polyalkylene oxides described, for example, in JP-B-37-16088 and 42-25201 and U.S. Pat. No. 3,532,501.

Preferably the developing solution contains a fluorescent whitening agent. In particular, it is preferable to use 4,4-diamino-2,2'-disulfostilbene-type compounds. Specifically, commercially available fluorescent whitening agents, such as compounds described, for example, in "Senshoku Note," 19th edition, pages 165 to 168, and compounds described in JP-A-4-242943, pages 3 to 7, can be used. The amount to be added is generally 0.1 to 10 g/liter, and preferably 0.5 to 5 g/liter.

The processing temperature of the developing solution to be applied to the present invention is 20 to 50° C., and preferably 30 to 45° C. The processing time is 5 sec to 2 min, and preferably 10 sec to 1 min. With respect to the replenishing rate, although a small amount is preferable, the replenishing rate is 15 to 600 ml, preferably 25 to 200 ml, and more preferably 35 to 100 ml, per $m^2$ of the photographic material.

The photographic material of the present invention may be in a form having an electro-conductive heat-generating element layer, which serves as a heating means for heat processing. In this case, as the heat-generating element, those described, for example, in JP-A-61-145544 can be employed.

The heating temperature in the heat development step is generally about 65 to 180° C., preferably 70 to 180° C., more preferably 75 to 180° C., further more preferably 80 to 150° C., and particularly preferably 80 to 135° C. The heating time is preferably 0.1 to 120 sec, more preferably 0.1 to 60 sec, and particularly preferably 0.1 to 30 sec.

Example heating methods in the development step include one wherein the photographic material is brought in contact with a heated block or plate; a method wherein the photographic material is brought in contact with a hot plate, a hot presser, a hot roller, a hot drum, a halogen lamp heater, an infrared lamp heater, or a far-infrared lamp heater; and a method wherein the photographic material is passed through a high-temperature atmosphere. As a method wherein the heat-developable photographic material and a dye-fixing material are placed one upon the other, methods described in JP-A-62-253159 and 61-147244 (page 27) can be applied.

After the development, a desilvering process can be carried out. The desilvering process comprises a fixing process, or both bleaching process and a fixing process. When both bleaching and fixing are carried out, the bleaching process and the fixing process may be carried out separately or simultaneously (bleach-fixing process). Also, according to the purpose, the processing may be carried out in a bleach-fixing bath having two successive tanks; or the fixing process may be carried out before the bleach-fixing process; or the bleach-fixing may be carried out after the bleach-fixing process.

In some cases, it is preferable to carry out the stabilizing process, to stabilize silver salts and dye images, without carrying out the desilvering process after the development.

Example bleaching agents for use in the bleaching solution or the bleach-fix solution include, for example, compounds of polyvalent metals, such as iron(III), cobalt(III), cromium(IV), and copper(II); peracids; qunones; and nitro compounds. Typical compounds are iron chloride, ferricyanides, dichromates, organic complex salts of iron (III) (e.g. metal salts of ethylenediaminetetraacetic acid, diethylenetriaminepentaacetic acid, cyclohexanediaminetetraacetic acid, 1,3-diaminopropanetetraacetic acid, methyliminodiacetic acid; and aminopolycarboxylic acids and their salts, as described in JP-A-4-365036, pages 5 to 17), persulfates, permanganates, bromates, hydrogen peroxide and compounds releasing thereof (e.g. percarbonic acid and perboric acid), and nitrobenzenes. Among them, ethylenediaminetetraacetatic acid iron(III) complex salts, aminopolycarboxylic acid iron(III) of 1,3-diaminopropanetetraacetate iron(III) complex salts, hydrogen peroxide, persulfates, and the like are preferred, in view of rapid processing and the prevention of enviromental pollution. The bleaching solution and bleach-fix solution that use these aminopolycarboxylic acid irons(III) are used at a pH of 3 to 8, and preferably 5 to 7. The bleaching solution that uses persulfates and hydrogen peroxide is used at a pH of 4 to 11, and preferably 5 to 10.

In the bleaching solution, the bleach-fix solution, and the bath preceding them, if required, a bleach-accelerating agent can be used. Specific examples of useful bleach-accelerating agents include compounds having a mercapto group or a disulfide bond, as described, for example, in U.S. Pat. No. 3,893,856, West German Patent No. 1 290 812, JP-A-53-95630, and Research Disclosure No. 17129 (July 1978); thiazolidine derivatives described in JP-A-50-140129; thiourea derivatives described in U.S. Pat. No. 3,706,561; iodide salts described in JP-A-58-16235; polyoxyethylene compounds described in West Germany Patent No. 2 748 430; and iodide ions and polyamine compounds described in JP-B-45-9936.

Above all, compounds having a mercapto group or a disulfide group are preferable, because they are high in accelerating effect. When color photographic materials for photography are desilvered, these bleach- accelerating agents are particularly effective.

With respect to the accelerating agent for persulfate bleaching, complex salts of 2,6-pyridinedicarboxylic acid or 2-pyridinecarboxylic acid with iron (III) ion, as described in JP-A-6-214365 (European Patent No. 0 602 600(A1)), are effective. With respect to the accelerating agent for hydrogen peroxide bleaching, metal salts of organic acids, described in JP-B-61-16067 and 61-19024, are effective.

In the bleaching solution, the bleach-fix solution, and the fixing solution, use can be made of known additives, such as a rehalogenating agent, including ammonium bromide and ammonium chloride; a pH buffering agent, including ammonium nitrate, acetic acid, boric acid, citric acid or its salt, tartaric acid or its salt, succinic acid or its salt, and imidazole; and a metal corrosion-preventive agent, including ammonium sulfate. In particular, it is preferable to contain an organic acid, to prevent bleach stain. The organic acid is a compound having an acid dissociation constant (pKa) of 2 to 7, and specifically acetic acid, succinic acid, citric acid, and propionic acid are preferable.

Example fixing agents for use in the fixing solution and the bleach-fix solution include thiosulfates, thiocyanates, thioureas, a large amount of iodide salts, and thioether compounds, metho-ionic compounds, and nitrogen-containing heterocyclic compounds, having a sulfide group, as described in JP-A-4-365037, pages 11 to 21, and JP-A-5-66540, pages 1088 to 1092. Among these, use of thiosulfates is usual, and ammonium thiosulfate is most widely used. A combination of thiosulfates with thiocyanates, thioether compounds, thiourea, or metho-ionic compounds, is also preferable.

Preferable preservatives for the fixing solution and the bleach-fix solution are sulfites, bisulfites, carbonylbisulfite adducts, and sulfinic acid compounds described in European Patent No. 294 769(A). In the fixing solution, the bleaching solution, and the bleach-fix solution, to stabilize the solutions, it is preferable to add any of various aminopoly-carboxylic acids, organic phosphonic acids (e.g. 1-hydroxyethylidene-1,1-diphosphonic acid, N,N,N',N'-ethylenediaminetetraphosphonic acid, and 2-phosphonobutane-1,2,4-ticarboxylic acid) and sodium stannate.

In the fixing solution and the bleach-fix solution, further, for example, any of various fluorescent whitening agents, antifoaming agents, surface-active agents, polyvinylpyrolidones, and methanol can be contained.

The processing temperature of the desilvering step is 20 to 50° C., and preferably 30 to 45° C. The processing time is 5 sec to 2 min, and preferably 5 sec to 1 min. Although a small replenishing rate is preferable, the replenishing rate is 15 to 600 ml, preferably 25 to 200 ml, and more preferably 35 to 100 ml, per $m^2$ of the photographic material. The processing is also preferably carried out without replenishment in such a way that the evaporated amount is supplemented with water.

The photographic material of the present invention is generally passed through a washing (rinsing) step after the desilvering process. If a stabilizing process is carried out, the washing step can be omitted. In such a stabilizing process, processes described in JP-A-57-8543, 58-14834, and 60-220345, and all known processes described in JP-A-58-127926, 58-137837, and 58-140741, can be used. A washing-stabilizing process, in which a stabilizing bath containing a dye stabilizer and a surface-active agent typically used for the processing of color photographic materials for photographing is used as a final bath, can be carried out.

In the washing liquid and stabilizing solution, use can be made of a water softener, such as sulfites, inorganic phosphoric acids, polyaminocarboxylic acids, and organic aminophosphoric acids; a metal salt, such as Mg salts, Al salts, and Bi salts; a surface-active agent, a hardener, a pH buffer, a fluorescent whitening agent, and a silver-salt-forming agent, such as nitrogen-containing heterocyclic compounds.

Example dye-stabilizing agents of the stabilizing solution include, for example, aldehydes, such as formaldehyde and glutaraldehyde; N-methylol compounds, hexamethylenetetramine, or aldehyde sulfite adducts.

The pH of the washing liquid and the stabilizing solution is 4 to 9, and preferably 5 to 8. The processing temperature is 15 to 45° C., and preferably 25 to 40° C. The processing time is 5 sec to 2 min, and preferably 5 sec to 40 sec.

The overflow liquid associated with the replenishment of the above washing liquid and/or the stabilizing solution, can be reused in other processes, such as the desilvering process.

The amount of the washing liquid and/or the stabilizing solution can be set in a wide range depending on various conditions, and the replenishing rate is preferably 15 to 360 ml, and more preferably 25 to 120 ml, per $m^2$ of the photographic material. To reduce the replenishing rate, it is preferable to use multiple tanks and a multi-stage counter-current system. In particular, it is preferable to use 2 to 5 tanks. In order to prevent the propagation of bacteria and adhesion stain of suspended matter on the photographic material that will result from reduction in the amount of these solutions, use can be made of bactericides, such as sodium chlorinated isocynurate, cyapentazoles, and isothiazolone compounds described in JP-A-57-8542; other benzotriazoles; and bactericides described by Hiroshi Horiguchi in "Bokin-bobaizai no Kagaku" (1986, Sankyo-shuppan); in "Biseibutsu no Mekkin, Sakkin, Bobai Gijutsu," edited by Eisei Bobai-gakkai (1982, Kogyo Gijutsu-kai); and in "Bokin Babai-zai Jiten," edited by Nihon Bokin Bobai-gakkai (1986). Further, a method of reducing Mg and Ca ions, as described in JP-A-62-288838, is particularly preferably used.

In the present invention, in order to save water, water can be used that has been obtained by treating the overflow liquid or the in-tank liquid using a reverse osmosis membrane. For example, the treatment by reverse osmosis is preferably carried out for water from the second tank, or the more latter tank of the multi-stage countercurrent washing process and/or the stabilizing process. Specifically, in the case of a two-tank system, the water in the second tank is treated by a reverse osmosis membrane, and in the case of a four-tank system, the water in the third tank and the fourth tank is treated by a reverse osmosis membrane, and then the passed water is returned to the first tank (the tank from which water for the reverse osmosis treatment has been taken) or is brought to a washing tank and/or a stabilizing tank situated downstream. It is also one mode that the concentrated liquid is returned to a tank situated upstream of that particular tank and further to the desilvering bath.

As the material of the reverse osmosis membrane, for example, cellulose acetates, crosslinked polyamides, polyethers, polysulfons, polyacrylic acids, and polyvinylene carbonates can be used. The pressure of the pumped liquid used for these membranes is preferably 2 to 10 kg/cm$^2$ and particularly preferably 3 to 7 kg/cm$^2$.

In the present invention, preferably the stirring is intensified as much as possible. To intensify the stirring, specifically a method wherein a jet stream of a processing liquid is caused to impinge on the emulsion surface of a photographic material, as described in JP-A-62-183460 and 62-183461; a method wherein a rotating means is used to increase the stirring effect, as described in JP-A-62-183461; a method wherein a photographic material is moved, with the emulsion surface of the material being in contact with a wiper blade provided in a liquid, so that a turbulent flow may occur near the emulsion surface, to improve the stirring effect; and a method wherein the total amount of a processing solution to be circulated is increased, can be mentioned. These means of improving the stirring are useful in any of the developing solution, the bleaching solution, the bleach-fix solution, the stabilizing solution, and the washing liquid. These methods are effective in that the effective constituents in the solution are supplied to the photographic material and the diffusion of unnecessary components in the photographic material is promoted.

In the present invention, any state of a liquid opening rate [contact area of air (cm$^2$)/liquid volume (cm$^3$)] of any of the baths can exhibit excellent performance, but in view of the stability of the liquid components, preferably the liquid opening rate is 0 to 1.0 cm$^{-1}$. In the continuous processing, from a practical point of view, the liquid opening rate is preferably 0.001 to 0.05 cm$^{-1}$, and more preferably 0.002 to 0.03 cm$^{-1}$.

The automatic processor used for the photographic material of the present invention is preferably provided with a means of transporting a photographic material, as described in JP-A-60-191257, 60-191258, and 60-191259. Such a transporting means can reduce remarkably the carry-in of the processing solution from a preceding bath to a succeeding bath. Therefore, it is high in the effect of preventing the performance of a processing solution from being deteriorated. Such an effect is effective in shortening the processing time of each process and in reducing the process replenishing rate. To shorten the processing time, it is preferable to shorten the crossover time (the aerial time), and a method wherein a photographic material is transported between processes through a blade having a screening effect, as described, for example, in JP-A-4-86659, FIG. 4, 5, or 6, and JP-A-5-66540, FIGS. 4 or 5, is preferable.

Further, if each of the processing solutions in the continuous process is concentrated due to evaporated, preferably water is added to compensate for the evaporation.

The processing time in each process according to the present invention means the time required from the start of the processing of the photographic material at any process, to the start of the processing in the next process. The actual processing time in an automatic processor is determined generally by the linear speed and the volume of the processing bath, and in the present invention, as the linear speed, 500 to 4,000 mm/min can be mentioned as a guide. Particularly in the case of a small-sized processor, 500 to 2,500 mm/min is preferable.

The processing time in the whole processing steps, that is, the processing time from the activator development process to the drying process, is preferably 360 sec or below, more preferably 120 sec or below, and particularly preferably 90 to 30 sec. Herein the processing time means the period from the dipping of the photographic material into the activator solution, till the emergence from the drying part of the processor.

The color-developing agent and coupler used in the present invention may be used for a light-sensitive element for color diffusion transfer method in which it is developed using a treating solution at around room temperature and for a thermal developing light-sensitive element which is developed by heating.

The silver halide which may be used for the above light-sensitive element may be any one of silver chloride, silver bromide, silver chlorobromide, silver chloroiodide and silver chloroiodobromide.

Specifically, any one of silver halide emulsions described in U.S. Pat. No. 4,500,626, 50th column, Journal of Research & Disclosure, the June issue, pp9–10 (1978) (RD17029), JP-A-61-107240, JP-A-62-85241 and JP-A-62-87957 may be used.

The silver halide emulsion used in the present invention may be either a surface latent image type in which a latent image is primarily formed on the surface of a grain or an internal latent image type in which a latent image is formed inside of a grain. The silver halide emulsion used in the present invention may also be a core/shell emulsion in which the inside and surface of a grain are formed of different layers. In the present invention, a direct reverse emulsion in which an internal latent image type emulsion is combined with a core-forming agent and/or a light cablace may be used.

Although a silver halide emulsion may be used just without after-ripening, it is usually used after it is chemically sensitized. In the case of normal light-sensitive material emulsions, a well-known sulfur sensitization method, reduction sensitization method and noble metal sensitization method may be used either singly or in combination. These chemical sensitizations may be carried out in the presence of a nitrogen-containing heterocyclic compound (JP-A-58-126526 and JP-A-58-215644). Usually the coating amount of the light-sensitive silver halide used in the present invention is 1 mg to 10 g/m$^2$, in terms of silver.

Also, the color-developing agent and coupler of the present invention may be used together with known dye-donating compounds including dye developing agents described later and compounds releasing a diffusible dye by a redox reaction in the same photographic element. For instance, a method may be used in which yellow and cyan images are formed by the color-developing agent represented by formula (1) or (2) and coupler of the present invention and a magenta image is formed by other dye image-forming compounds. Further, for instance, a method may be used in which a magenta image is formed by the color-developing agent represented by formula (3) and coupler represented by formula (4) defined in the present invention and yellow and cyan images are formed by other dye image-forming compounds.

As the dye image-forming compound which may be used together in the present invention, first, combinations of known developers and couplers which can react therewith may be typified. This system using a coupler is to form a dye by reacting an oxidized product of developer, which is produced by a redox reaction between a silver salt and the developing agent, with the coupler and is described in abundant literature. This coupler may be either a four-equivalent coupler or a two-equivalent coupler. It is also preferable to use a two-equivalent coupler which has a diffusion resistant group in an elimination group and produces a diffusible dye by the reaction with the oxidized product of the developer. Specific examples of the developing agent and the coupler are described in detail, for example, in "Theory of The Photographic Process" (4th Ed., edited by T. H. James), pages 291 to 334 and 354 to 361, and in JP-A-58-12353, 58-149046, 58-149047, 59-111148, 59-124399, 59-174835, 59-231539, 6-231540, 60-2950, 60-2951, 60-14242, 60-23474, and 60-66249.

In addition, as dye-image forming compounds, for example, dye silver compounds formed by combining an organic silver salt with a dye can be mentioned. Examples of dye silver compound is described in, for example, Research Disclosure, May, 1978, pages 54 to 58 (RD-16966).

Further, azo dyes used in the heat-developable silver dye bleach process can be mentioned as an example of dye-image forming compound. Specific examples of azo dyes and bleaching methods are described in, for example, U.S. Pat. No. 4,235,957 and Research Disclosure, April, 1976, pages 30 to 32 (RD-14433). In addition, leuco dyes described in, for example, U.S. Pat. No. 3,985,565 and U.S. Pat, No. 4,022,617 can be mentioned as an example.

Further, as an example of other dye-image forming compound, compounds having a function of releasing or diffusing a diffusion dye imagewise can be mentioned.

The compounds of this type can be represented by the following formula [LI]:

$$(Dye-X)_n-Y \quad [LI]$$

Dye represents a dye group, a dye group whose wavelength is temporarily shortened, or a dye precursor group, X represents a mere single bond or a linking group, Y represents a group which has such a property that produces a difference in the diffusibility of the compound represented by $(Dye-X)_n-Y$ correspondingly or inversely-correspondingly to the light-sensitive silver salt having a latent image imagewise, or that releases Dye, to produce a difference in the diffusibility between Dye released and $(Dye-X)_n-Y$. n is 1 or 2, and when n is 2, a plurality of Dye-Xs may be the same or different.

As specific examples of the dye-donating material represented by the formula [LI], dye developers in which a hydroquinone type developer is combined with a dye component are described in U.S. Pat. No. 3,134,764, U.S. Pat. No. 3,362,819, U.S. Pat. No. 3,597,200, U.S. Pat. No. 3,544,545 and U.S. Pat. No. 3,482,972. Also, materials releasing a diffusible dye by an intermolecular nucleophilic substitution reaction and by an intermolecular rollback reaction of isoxazolone ring are described in JP-A-51-63618 and JP-A-49-111628 respectively. In all of these methods, a diffusible dye is released or diffused in undeveloped parts, but neither released nor diffused in developed parts.

A further method has been devised in which a dye-releasing compound is made to be an oxidized product type incapable of releasing a dye and to coexist together with a reducing agent or its precursor and after being developed, the dye-releasing compound is reduced by a reducing agent left non-oxidized to thereby release a diffusible dye. Specific examples of the dye image-forming compound used in this method are described in JP-A-53-110,827, JP-A-54-130, 927, JP-A-56-164,342 and JP-A-53-35,533.

As materials releasing a dye in developed parts, materials releasing a diffusible dye by a reaction between a coupler having a diffusible dye in an elimination group and an oxidized product of a developer are described in U.K. Patent No. 1,330,524, JP-B-48-39,165 and U.S. Pat. No. 3,443,940.

In the system using these color-developers, image contaminations with oxidation-decomposed products of the developer cause a serious problem. A dye-releasing compound which needs no developing agent and itself has reducibility has been devised to solve the problem. Typical examples of the dye-releasing compound include dye image-forming compounds described in U.S. Pat. No. 3,928,312, U.S. Pat. No. 4,053,312, U.S. Pat. No. 4,055,428 and U.S. Pat. No. 4,336,322, JP-A-59-65839, JP-A-59-69839, JP-A-51-104,343, Journal of Research & Disclosure No. 17465, U.S. Pat. No. 3,725,062, U.S. Pat. No. 3,728,113 and U.S. Pat. No. 3,443,939, JP-A-58-116537, JP-A-57-179840 and U.S. Pat. No. 4,500,626.

In the system forming an image by diffusion transfer of a dye by using the light-sensitive material of the present invention, the light-sensitive materials are generally divided into two types: one type in which a light-sensitive element and an image-receiving element (dye-fixing element) are formed separately by application on two supports (these may be referred to a light-sensitive material and dye-fixing material, respectively) and another type in which the both are formed by application on the same support.

The mutual relations of the light-sensitive element to the dye-fixing element, to the supports and to a white reflecting layer which are described in the specification of JP-A-61-147244, pp58–59 and U.S Pat. No. 4,500,626, 57th column may be applied to the light-sensitive material of the present invention.

A typical type of film unit in which a light-sensitive element and an image receiving element are formed on the same support is one in which the image-receiving element and the light-sensitive element are laminated on one transparent support and which eliminates the necessity of peeling the light-sensitive element from the image-receiving element after a transferred image is completed. To state in more detail, the image-receiving element comprises at least one mordant layer (also called an image-receiving layer or a dye-fixing layer). Also, the light-sensitive element, in preferred embodiments, comprises a combination of a blue-sensitive emulsion layer, green-sensitive emulsion layer and red-sensitive emulsion layer, a combination of a green-sensitive emulsion layer, red-sensitive emulsion layer and infrared-light-sensitive emulsion layer or a combination of a blue-sensitive emulsion layer, red-sensitive emulsion layer and infrared-light-sensitive emulsion layer. Moreover, a yellow dye image-forming compound (a dye image-forming compound containing the color-developing agent and coupler of the present invention), a magenta dye image-forming compound (a dye image-forming compound containing the color-developing agent and coupler of the present invention) and a cyan dye image-forming compound (a dye image-forming compound containing the color-developing agent and coupler of the present invention) are respectively combined with the above emulsion layers. Thus, the image-forming system of the present invention is structured (Here, the "infrared-light-sensitive emulsion layer" means an emulsion layer possessing sensitivity to light of 700 nm or more and especially 740 nm or more). Each of these light-sensitive emulsion layers may be divided into two or more layers as required. in addition, a white reflecting layer containing a solid dye, e.g., titanium oxide, is formed between the mordant layer and the light-sensitive layer or the dye image-forming compound (the dye image-forming compound containing the color-developing agent and coupler of the present invention) so as to observe the transferred image through the transparent support. A shading layer may be further formed between the white reflecting layer and the light-sensitive layer so as to complete developing treatment in light fields. Also, as desired, a peelable layer may be formed at a proper position to peel all or a part of the light-sensitive element from the image-receiving element (embodiments like this are described in JP-A-56-67840 and C.A. Patent No. 674,082).

In other types which do not need peeling, the light-sensitive element is formed by application on one transparent support, a white reflecting layer is formed by application on the light-sensitive element and an image-receiving layer is further laminated on the white reflecting layer. The type in which an image-receiving element, a white reflecting layer, a peelable layer and a light-sensitive element are laminated on the same support and the light-sensitive element is intentionally peeled from the image-receiving element is described in U.S. Pat. No. 3,730,718. On the other hand, the typical types in which the light-sensitive element and the image-receiving element are separately formed by application on two supports are loosely divided into two categories: one category is a peelable type and another category is a peeling-needless type. To mention these types in detail, in a preferred embodiment of the peelable film unit, a light-reflecting layer is provided on the backface of a support and at least one image-receiving layer is formed by application on the surface of the support. Also, the light-sensitive element is formed by application on a support provided with a shading layer. This embodiment is devised such that the surface of the applied light-sensitive layer does not face the surface of the applied mordant layer until the exposure is finished, but the surface of the applied light-sensitive layer is overturned so that it faces the surface of the applied mordant layer after the exposure was finished (for instance, during developing). The light-sensitive element is peeled from the image-receiving element immediately after the transferred image is completed.

In a preferred embodiment of the peeling-needless film unit, at least one mordant layer is formed on a transparent support and a light-sensitive element is formed by application on a support provided with a transparent or shading layer and the surface of the applied light-sensitive layer and the surface of the applied mordant layer are facing and are overlapped on each other.

The aforementioned modes may be applied to both of a system of development using an alkaline solution which is developed (expanded) in a light-sensitive material, and a heat development system. In, particularly, the former system, a container (treating element) which contains the process alkaline solution and can be burst may be combined. In, among these systems, the peeling-needless film unit in which an image-receiving element and a light-sensitive element are laminated on one support, the treating unit is preferably disposed between the light-sensitive element and a cover sheet which is overlapped on the light-sensitive element. Also, in the type in which a light-sensitive element and an image-receiving element are separately formed by application on two supports, the treating element are preferably disposed between the light-sensitive element and the image-receiving element during the developing time at the latest. Preferably the treating element contains a shading agent (e.g., carbon black and dyes which are changed in color depending upon pH) and/or a white pigment (titanium oxide) according to the type of film unit. In a film unit of the type which develops using a process alkali solution, preferably a neutralization-timing mechanism consisting of a combination of a neutralization layer and a neutralization timing layer is incorporated into the cover sheet, the image-receiving element or the light-sensitive element.

As the mordant agent used in the aforementioned image-receiving element or the dye-fixing element explained later, a polymer mordant agent is preferable. Here, the polymer mordant agents are, for example, polymers containing a tertiary amino group, polymers containing a nitrogen-containing heterocyclic portion and polymers containing a quaternary cationic group.

Specific examples of these polymer mordant agents are described in JP-A-61-147244, pp98–100 and U.S. Pat. No. 4,500,626, 57th–60th columns.

When the present invention is applied to a heat-developable light-sensitive material, the silver halide may be used together with an organic metal salt as an oxidizing agent. In this case, it is necessary that the light-sensitive silver halide and the organic metal salt are in contact with each other or close to each other.

Among these organic metal salts, organic silver salts are used particularly preferably.

Examples of organic compounds which may be used to produce the above oxidized product of organic silver salt include compounds described in JP-A-61-107240, pp37–39 and U.S. Pat. No. 4,500,626, 52th–53th columns. Silver salts of carboxylic acid having an alkinyl group, such as silver phenylpropiolate, described in JP-A-60-113235 and silver acetylide described in JP-A-61-249044 are also useful. organic silver salts may be used in combinations of two or more.

Among such organic metal salts, organic silver salt is particularly preferably used.

As the organic compound that can be used to form the above organic silver salt oxidizing agent, compounds described in JP-A-61-107240, columns 37 to 39, and those described in U.S. Pat. No. 4,500,626, columns 52 to 53, can be mentioned. Further, a silver salt of a carboxylic acid having an alkinyl group, such as silver phenylpropiolate, described in JP-A-60-113235, and silver acetylide described in JP-A-61-249044 are also useful. Organic silver salts may be used in combination of two or more.

The above organosilver salts may be used additionally in an amount of generally 0.01 to 10 mol, and preferably 0.01 to 1 mol, per mol of the light-sensitive silver halide. Suitably the total coating amount of the light-sensitive silver halide plus the organosilver salt is generally 50 mg to 10 g/m$^2$, in terms of silver.

Hydrophobic additives among the aforementioned additives may be introduced into the layers of the light-sensitive material according to a known method as described in U.S. Pat. No. 2,322,027. In this case, high-boiling point organic solvent as described in JP-A-59-83154, JP-A-59-178451, JP-A-59-178452, JP-A-59-178453, JP-A-59-178454, JP-A-59-178455 and JP-A-59-178457 may be used, as required, together with a low-boiling point organic solvent having a boiling point as low as 50° C. to 160° C.

Also, a dispersion method using a polymer as described in JP-B-51-39853 and JP-A-51-59943 may be used.

In the case of compounds which are substantially insoluble in water, they may be made into fine grains, which are dispersed in a binder instead of using the aforementioned methods.

When a hydrophobic material is dispersed in a hydrophilic colloid, various surfactants may be used. For example, those described as surfactants in JP-A-59-157636, pp37–38 may be used.

In the present invention, reducing materials may be desirably used in the light-sensitive element. The reducing materials generally include, other than those known as reducing agents, the aforementioned dye image-forming compound containing the color-developing agent used in the present invention. The reducing materials also include a reducing agent precursor which itself has no reducibility but develops reducibility by the effect of a nucleophilic agent or heat during a developing stage.

Examples of the reducing agent which can be utilized in the present invention include those described in U.S. Pat. No. 4,500,626, 49th–50th columns, U.S. Pat. No. 4,483,914, 30th–31th columns, JP-A-60-140335, pp17–18, JP-A-60-128438, JP-A-60-128436, JP-A-60-128439 and JP-A-60-128437. Reducing agent precursors described in JP-A-56-138736, JP-A-57-40245 and U.S. Pat. No. 4,330,617 may also be utilized.

Moreover, combinations of various reducing agents as described in U.S. Pat. No. 3,039,869 may be used.

In the present invention, the amount of the reducing agent to be added is 0.01 to 20 mols and particularly preferably 0.1 to 10 mols based on 1 mol of silver.

In the present invention, compounds which improve developing activity and the stability of an image may be used in the light-sensitive element. Specific compounds which are preferably used are described in U.S. Pat. No. 4,500,626, 51th–52th columns.

In the present invention, various fog-preventive agent and photographic stabilizers may be used. Examples of these agents which may be used in the present invention include azoles and azaindenes described in Journal of Research & Disclosure, the December issue, pp24–25 (1978), nitrogen-containing carboxylic acids and phosphoric acids described in JP-A-59-168442, mercapto compounds and their metal salts described in JP-A-59-111636 and acetylene compounds described in JP-A-62-87957.

In the present invention, the light-sensitive element may include an image color-adjusting agent as required. Specific examples of effective color-adjusting agents include compounds described in JP-A-61-147244, pp92–93.

The light-sensitive element used in the present invention may comprise, as required, various additives which are known as materials used for a heat developing light-sensitive element and layers other than the light-sensitive layer such as a protective layer, intermediate layer, antistatic layer, antihalation layer, peelable layer which makes peeling from a dye-fixing element easy and a matte layer. These various additives include plasticizers, matte agents, vividness-improving dyes, antihalation dyes, surfactants, fluorescent brighteners, antislip agents, antioxidized products, color fading preventive agents and diffusible dye trap agent, which are all described in Journal of Research & Disclosure, the June issue, pp9–15 (1978) and JP-A-61-88256.

Especially the protective layer is usually made to contain organic and inorganic matte agents to prevent adhesion. This protective layer may also include a mordant agent and a UV-ray absorber. The protective layer and the intermediate layer may be respectively structured of two or more layers.

Also, the intermediate layer may include a reducing agent, a UV-ray absorber and a white pigment, e.g., titanium dioxide to prevent color-fading and color mixing. The white pigment may be added not only to the intermediate layer but also to the emulsion layer to improve the sensitivity.

The dye-fixing element may be provided with auxiliary layers such as a protective layer, peelable layer and curling preventive layer as required. Particularly it is useful to provide the protective layer. One or more of the aforementioned layers may include hydrophilic heat solvents, plasticizers, color-fading preventive agents, UV-ray absorbers, anti-slip agents, matte agents, antioxidized products, disperse vinyl compounds for increasing dimentional stability, surfactants, luminescent whiteners and the like. Further, particularly, in the system wherein the heat development and the transfer of the dye are carried out simultaneously in the presence of a small amount of water, a base and/or a base precursor is preferably contained in the dye-fixing element, with a view to increasing the preservability of the light-sensitive element. Specific examples of these additives are described in JP-A-61-88256, pages 101 to 120.

In the light-sensitive element and/or the dye-fixing element according to the present invention, an image-forming promoter may be used. The image-forming promoter has an ability to promote a redox reaction between a silver salt oxidizing agent and a reducing agent, an ability to promote reactions to produce a dye from the dye image-forming compound containing the color-developing agent and coupler of the present invention, to decompose the dye and to release a diffusible dye from the dye image-forming compound and an ability to promote the transfer of the dye from the structural layer of the light-sensitive element to the dye-fixing layer. From the physicochemical abilities, the image-forming promoters are classified into bases or base precursors, nucleophilic compounds, high boiling point organic solvents (oil), heat solvents, surfactants, compounds which interact with silver or silver ions and the like. It is to be noted that these material groups usually have duplex abilities and possess some of the above promoting effects in general. The details of these materials are described in JP-A-61-93451, pp67–71.

There are various methods for the production of a base. Compounds used in these methods are all useful as a base precursor. There are, for example, a method described in E.P. Patent No. 0210660A2 in which a base is generated by mixing a metal compound (e.g., metal salts), which is sparingly soluble in water, with a compound (a complex-forming compound or complexing agent) which can react with metal ions constituting the metal compound, which is sparingly soluble in water, to form a complex and a method described in JP-A-61-232451 in which a base is generated by electrolysis.

Especially, the former method is effective. Given as examples of the metal salt which is sparingly soluble in water are carbonates, hydroxides or oxides of zinc, aluminum, calcium or barium. The complex-forming compounds are explained in detail, for example, in "Critical Stability Constants" written jointly by "A. E. Martell, R. M. Smith, Vol No. 4 and Vol. No. 5, Plenum Press. Specific examples include salts of aminocarboxylic acids, iminodiacetic acids, pyridinecarboxylic acids, aminophosphoric acids, carboxylic acids (mono-, di-, tri-, tetra-carboxylic acids and compounds having each of substituents, e.g., a phosphono, hydroxy, oxo, ester, amide, alkoxy, mercapto, alkylthio or phosphino group), hydroxam acids, polyacrylates or polyphosphoric acids and alkali metals, guanidines, amidines or quaternary ammonium salts.

It is advantageous to add these metal compound which is sparing soluble in water and complex-forming compound to each of the light-sensitive element and dye-fixing element.

In the light-sensitive element and/or the dye-fixing element for use in the present invention, in order to obtain a constant image all the time, against fluctuation of the processing temperature and the processing time at the time of development, various development-stopping agents can be used.

Herein, the term "a development-stopping agent" means a compound that neutralizes bases quickly or reacts quickly with bases after proper development, to lower the base concentration in the film, to stop the development; or a compound that interacts with silver and silver salts, to inhibit the development. Specific examples include acid precursors that release an acid when heated, electrophilic compounds that undergo a substitution reaction with coexisting bases when heated, nitrogen-containing heterocyclic compounds, mercapto compounds, and their precursors (for example, compounds described in JP-A-60-108837, JP-A-60-192939, JP-A-60-230133, and JP-A-60-230134).

Also, compounds which release a mercapto compound by heating are also useful. These compounds are described in, for example, JP-A-61-67851, JP-A-61-147244, JP-A-61-124941, JP-A-61-185743, JP-A-61-182039, JP-A-61-185744, JP-A-61-184539,. JP-A-61-188540 and JP-A-61-53632.

As the binder of light-receiving element and/or dye-fixing element of the present invention, a hydrophilic binder is preferably used. Typically, the hydrophilic binder is a transparent or semitranparent hydrophilic binder. Specifically, examples include natural compounds such as proteins including gelatin, gelatin derivatives and the like, or polysaccharides including cellulose derivatives, starches, gum-arabic, dextrans, and the like; and synthetic polymer compounds such as water soluble polyvinyl compounds including polyvinyl pyrrolidones, and acrylamide polymers. A disperse vinyl compound which is used in the form of a latex and increase the dimentional stability of photographic materials may also be used. These binders may be used either singly or in combinations.

It is proper that the amount of the binder to be applied in the present invention is 20 g or less, preferably 10 g or less and more preferably 7 g or less per 1 $m^2$.

A proper ratio of a high-boiling point organic solvent dispersed in the binder together with hydrophobic compounds such as the color-developing agent and coupler of the present invention to the binder is as follows: the amount of the solvent is 1 cc or less, preferably 0.5 cc or less and more preferably 0.3 cc or less based on 1 g of the binder.

The light-sensitive element and/or the structural layer (e.g., a photographic emulsion layer and a dye-fixing layer) of the dye-fixing element in the present invention may contain an inorganic or organic hardener.

Specific examples of the hardener include those described in the specification of JP-A-61-147244, pp94–95 and in the specification of JP-A-59-157636, pp38. These compounds may be used either singly or in combination.

To accelerate the dye transfer, a system can be adopted wherein a hydrophilic heat solvent that is solid at normal temperatures and melts at a higher temperature is built in the light-sensitive element and/or the dye-fixing element. The heat solvent can be is built in any of light-sensitive element and dye-fixing element, and it may be built in both elements. Further, the layer wherein the hydrophilic heat solvent is built in may be any of the emulsion layer, the intermediate layer, the protective layer, and the dye-fixing layer, but preferably it is the dye-fixing layer and/or the layer adjacent thereto. Examples of the hydrophilic heat solvent include ureas, pyridines, amides, sulfonamides, imides, alcohols, oximes, and other heterocyclic compounds. Further, to accelerate the dye transfer, high-boiling organic solvent can be contained in a light-sensitive element and/or image-receiving element.

The support used for the light-sensitive element and/or the dye-fixing element can stand against treating temperature. As a usual support, glass, paper, polymer films, metals or similar materials may be used and also those described as supports in the specification of JP-A-61-147244, pp95–96 may be used.

The light-sensitive element and/or the dye-fixing element may be a type having a conductive exothermic body layer to be used as a heating means for heating development or the transfer of a dye.

A transparent or opaque exothermic element in this case may be made as a resistive exothermic body by making use of conventionally well-known techniques. As the method of producing the resistive exothermic body, there are a method which makes use of a thin film of an inorganic material exhibiting semiconductivity and a method which makes use of an organic thin film in which electroconductive fine grains are dispersed in a binder. As materials used in these methods, compounds described in the specification of JP-A-61-29835 may be used.

In the present invention, to apply a heat developing light-sensitive layer, protective layer, intermediate layer, undercoat layer, back layer, dye-fixing layer and other layers, a method described in U.S. Pat. No. 4,500,626, 55th–56th columns can be used.

As a light source for image exposure used to record an image in the light-sensitive element, radiation rays including visible light may be used. In general, light sources used in usual color printing, for instance, a tungsten lamp, mercury lamp, halogen lamps such as an iodine lamp, xenon lamp, laser light source, CRT light source or light emitting diode (LED), which are all described in JP-A-61-147244, pp100 and U.S. Pat. No. 4,500,626, 56th column, may be used.

In the image-forming method involving a heating step to which the present invention is applied, for example, a heat developing step and a dye-transfer step are carried out either separately or simultaneously. Also, both steps may be successive in the meaning of the fact that a transfer operation is carried out in succession to a developing operation in one step.

For instance, there are (1) a method in which an image is formed on the light-sensitive element by exposure, followed by heating, thereafter a dye-fixing element is overlapped on the light-sensitive element and, as required, heated to transfer a movable dye to the dye-fixing element and (2) a method in which an image is formed on the light-sensitive element by exposure and a dye-fixing element is overlapped on the light-sensitive element, followed by heating. The aforementioned methods (1) and (2) may be applied either in substantially the absence of water or in the presence of minute water.

The heating temperature in the heat developing step, although the development can be made at about 50 to 250° C., is preferably 70° C. to 180° C. and particularly preferably 75° C. to 150° C. In the case of heating in the presence of minute water, the upper limit of the heating temperature is below the boiling temperature. When the transfer step is performed after the heat developing step is finished, the heating temperature in the transfer step, though the transfer can be made in a temperature range between the temperature in the heat developing step and room temperature, is more preferably above 50° C. and lower than the temperature in the heat developing step by 10° C.

In a preferred image-forming method according to the present invention, an image is exposed or heating is performed in the presence of minute water and a base and/or a base precursor when an image is exposed and a diffusible dye generated in the parts corresponding or reversely corresponding to a silver image at the same time of developing is transferred to the dye-fixing layer. This method ensures that the production and releasing reactions of the diffusible dye run very quickly and hence the diffusible dye is transferred to the dye-fixing layer rapidly thereby to obtain a high density color image in a short period of time.

The amount of water to be used in this embodiment is as small as 0.1 times and preferably more than 0.1 times the weight of the total applied film of the light-sensitive element and dye-fixing layer and less than the amount (specifically, less than the amount calculated by subtracting the weight of the total applied film from the weight of the solvent corresponding to the maximum swelled volume of the total applied film) of the solvent corresponding to the maximum swelled volume of the total applied film.

The condition of the film during swelling is unstable and local bleeding is likely caused depending upon the condition. In order to evade this phenomenon, the amount of water is preferably smaller than the amount corresponding to the volume of the total applied film of the light-sensitive element and dye-fixing element when the film reaches a maximum swelling. Concretely, the amount of water is in a range between 1 and 50 g, preferably 2 and 35 g and more preferably 3 and 25 g.

A base and/or base precursor used in this embodiment may be incorporated into the light-sensitive element and the dye-fixing element. The base and/or base precursor may also be supplied after it is dissolved in water.

In the above embodiment, it is preferable that the image-forming reaction system be made to contain a metal compound (e.g., a basic metal compound which is sparing soluble in water), which is sparing soluble in water, as a base precursor and a compound (a complexing agent) which can react with a metal ion constituting the metal compound, which is sparing soluble in water, by using water as a medium to form a complex and an alkali be generated by the reaction of both compounds during heating to raise the pH of the system. Here, the image reaction system means the region where an image-forming reaction is caused. Given as specific example of the region are layers belonging to both of the light-sensitive element and dye-fixing element. In the case where two or more layers are present, the reaction system may be included in any of these layers.

It is necessary to add the metal compound which is sparing soluble in water and the complex-forming compound to at least separate layers to prevent the both from reacting with each other by the time of developing treatment. For example, in a so-called monosheet material in which the light-sensitive element and the dye-fixing element are formed in the same support, it is desirable that the layers to which the both are added separately and one or more layers are interposed between these separate layers. In a more preferred embodiment, the metal compound which is sparingly soluble in water and the complex-forming compound are respectively contained in each layer formed on separate supports. For example, it is desirable that the metal compound which is sparingly soluble in water be contained in the light-sensitive element and the complex-forming compound be contained in the dye-fixing element having a support different from that of the light-sensitive element. The complex-forming compound may be supplied after it is dissolved in water allowed to coexist. Preferably the metal compound which is sparingly soluble in water is contained in the form of a fine grain dispersion prepared according to the methods described in, for example, JP-A-56-17480 and JP-A-53-102733. Preferably the average grain size of the fine grain dispersion is 50μm or less and particularly 5 μm or less. The metal compound which is sparingly soluble in water may be added to any one of the light-sensitive layer, intermediate layer and protective layer of the light-sensitive element and may be added separately to two or more layers.

When the metal compound which is sparingly soluble in water or the complex-forming compound is to. be contained in a layer on a support, the amount of the compound depends on the type of compound, the grain size of the metal compound which is insoluble in water and the rate of reaction for forming a complex. The metal compound or the complex-forming compound is used preferably in an amount of 50% by weight or less and more preferably in an amount ranging from 0.01% by weight to 40% by weight. When the complex-forming compound is supplied after it is dissolved in water, its concentration is in a range preferably from 0.005 mols to 5 mols and particularly from 0.05 mols to 2 mols per 1 liter of the solution. In the present invention, the content of the complex-forming compound in the reaction system is preferably 1/100 times to 100 times and particularly preferably 1/10 times to 20 times the content of the compound, which is sparingly soluble in water, in terms of molar ratio.

A method of supplying water to the light-sensitive layer or the dye-fixing layer includes, for example, one described in JP-A-61-147244, pp101, line 9 to pp102, line 4.

As heating means in the developing step and/or transfer step, there are means described in JP-A-61-147244, pp102, line 14 to pp103, line 11, for example, a heating plate, iron and heat roller. A method may be adopted in which layers of conductive materials such as graphite, carbon black and metals are overlapped on the light-sensitive element and/or dye-fixing element and current is allowed to flow through the conductive layer to heat directly.

As pressure conditions and a method of applying pressure when the light-sensitive element and the dye-fixing element are overlapped on each other and stuck to each other, a method described in JP-A-61-147244, pp103 to 104 may be used.

To process the photographic elements for use in the present invention, any of various heat development apparatuses can be used. For example, apparatuses described, for example, in JP-A-59-75247, JP-A-59-177547, JP-A-59-181353, and JP-A-60-18951, unexamined published Japanese Utility Model Application (JU-A) No. 62-25944, and JP-A-6-130509, JP-A-6-95338, and JP-A-6-95267 are preferably used.

Employment of the color-developing agent in the present invention ensures that better color-developing ability(color-forming property) can be obtained even in a short developing time and a developed color image which has high stability against light, heat and humidity can be obtained.

Further, according to the color diffusion transfer type silver halide photographic material and image-forming method of the present invention, good color-developing ability can be obtained even in a short developing time and a transferred color image stable against light, heat and humidity can also be obtained by using the color-developing agent and the particular phenol type coupler.

EXAMPLES

Now, the present invention is described in more detail with reference to the following examples, but the present invention is not limited thereto.

Example 1

Image Receiving Element R101 having the constitution shown in Tables 1 and 2 was made.

TABLE 1

Constitution of Image Receiving Element R101

| Number of layer | Additive | Coated amount (mg/m$^2$) |
|---|---|---|
| Sixth layer | Water-soluble polymer(1) | 130 |
| | Water-soluble polymer(2) | 35 |
| | Water-soluble polymer(3) | 45 |
| | Potassium nitrate | 20 |
| | Anionic surfactant(1) | 6 |
| | Anionic surfactant(2) | 6 |
| | Amphoteric surfactant(1) | 50 |
| | Stain-preventing agent(1) | 7 |
| | Stain-preventing agent(2) | 12 |
| | Matting agent(1) | 7 |
| Fifth layer | Gelatin | 250 |
| | Water-soluble polymer(1) | 25 |
| | Anionic surfactant(3) | 9 |
| | Hardener(1) | 185 |
| Forth layer | Mordant(1) | 1870 |
| | Water-soluble polymer(2) | 260 |
| | Water-soluble polymer(4) | 1380 |
| | Dispersion of latex(1) | 600 |
| | Anionic surfactant(3) | 25 |
| | Nonionic surfactant(1) | 18 |
| | Guanidine picolinate | 2550 |
| | Sodium quinolinate | 350 |
| Third layer | Gelatin | 370 |
| | Mordant(1) | 300 |
| | Anionic surfactant(3) | 12 |
| Second layer | Gelatin | 700 |
| | Mordant(1) | 290 |
| | Water-soluble polymer(1) | 55 |
| | Water-soluble polymer(2) | 330 |
| | Anionic surfactant(3) | 30 |
| | Anionic surfactant(4) | 7 |
| | High-boiling organic solvent (1) | 700 |
| | Brightening agent(1) | 30 |
| | Stain-preventing agent(3) | 32 |
| | Guanidine picolinate | 360 |
| | Potassium quinolinate | 45 |
| First layer | Gelatin | 280 |
| | Water-soluble polymer(1) | 12 |
| | Anionic surfactant(1) | 14 |
| | Sodium metaborate | 35 |
| | Hardener(1) | 185 |

Base(1) Polyethylene-Laminated Paper Support (thickness 215 μm)
The coated amount of dispersion of latex is in terms of the coated amount of solid content of latex.

TABLE 2

Constitution of Support (Base (1))

| Name of layer | Composition | Film thickness (μm) |
|---|---|---|
| Surface undercoat layer | Gelatin | 0.1 |
| Surfact PE layer (Glossy) | Low-density polyethylene (Density 0.923): 90.2 parts Surface-processed titanium oxide: 9.8 parts Ultramarine: 0.001 parts | 36.0 |
| Pulp Layer | Fine quality paper (LBKP/NBKP = 6/4, Density 1.053) | 152.0 |
| Back-surface PE layer (Matte) | High-density polyethylene (Density 0.955) | 27.0 |
| Back-surface undercoat layer | Styrene/acrylate copolymer Colloidal silica Polystyrenesulfonic acid sodium salt | 0.1 |
| | | 215.2 |

Anionic surfactant (1)

$$NaO_3S-CH(CH_2COOCH(C_2H_5)C_4H_9)COOCH(C_2H_5)C_4H_9$$

Anionic surfactant (2)

$$C_8F_{17}O_2S-N(C_3H_7)-COOK$$

Anionic surfactant (3)

NaO$_3$S—C$_6$H$_4$—C$_n$H$_{2n+1}$,  n = 12.6

Anionic surfactant (4)

[structure with C$_8$H$_{17}$ groups, O(CH$_2$)$_4$SO$_3$Na and OH groups], x:y = 4:6, m = 6.8

Nonionic surfactant (1)

C$_8$H$_{17}$—C$_6$H$_4$—O(CH$_2$CH$_2$O)$_n$-H,  n = 85

Amphoteric sarfactant (1)

$$C_{13}H_{27}CONHCH_2CH_2CH_2-N^{\oplus}(CH_3)_2-CH_2COO^{\ominus}$$

Brightening agent (1)

[bis-benzoxazole thiophene structure with t-butyl substituents]

-continued

Mordant (1)

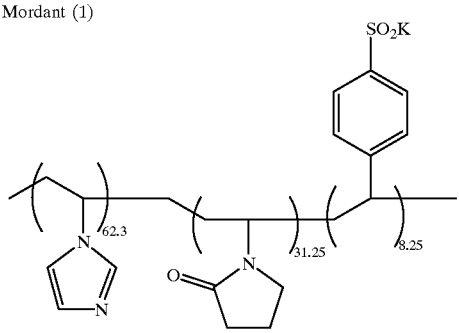

High-boiling solvent (1)
$C_{28}H_{46.9}Cl_{7.1}$ (EMPARA 40 (trade name: manufactured by Ajinomoto K.K.))

Stain-preventing agent (1)

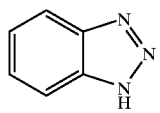

Stain-preventing agent (2)

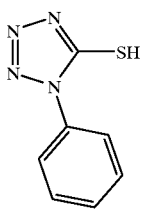

Stain-preventing agent (3)

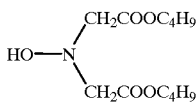

| Water-soluble polymer (1) | |
|---|---|
| Sumikagel L5-H | (trade name: manufactured by Sumitomo Kagaku CO.) |
| Water-soluble polymer(2) | |
| Dextran (molecular weight 70,000) | |
| Water-soluble polymer(3) | |
| κ(kappa)-Carrageenan | (trade name: manufactured by Taito Co.) |
| Water-soluble polymer(4) | |
| MP polymer MP-102 | (trade name: manufactured by Kuraray Co.) |
| Dispersion of latex(1) | |
| LX-438 | (trade name: manufactured by Nippon Zeon Co.) |
| Matting agent(1) | |
| SYLOID79 | (trade name: manufactured by Fuji Davisson Kagaku Co.) |

Hardener (1)

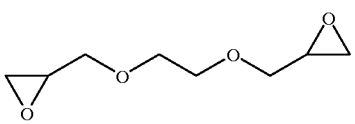

Next, the methods of preparing light-sensitive elements are described.

First, the methods of preparing light-sensitive silver halide emulsions are described. Light-Sensitive Silver Halide Emulsion (1) [for a red-sensitive emulsion layer]

Solution (I) having the composition shown in Table 4 was added to a well-stirred aqueous solution having the composition shown in Table 3, over 9 min at a constant flow rate, and before 10 sec of the addition of Solution (I), Solution (II) was added over 9 min 10 sec at a constant flow rate. Then, after 36 min, Solution (III) having the composition shown in Table 4 was added over 24 min at a constant flow rate, and simultaneously with the addition of Solution (III), Solution (IV) was added over 25 min at a constant flow rate.

After washing with water and desalting (at a pH of 4.0 using Settling Agent a) in a usual manner, 880 g of lime-processed ossein gelatin was added, the pH was adjusted to 6.0, and after the chemical sensitization was carried out optimally at 60° C. for 71 min by adding 12.8 g of a ribonucleic acid decomposition product and 32 mg of trimethylthiourea, then, 2.6 g of 4-hydroxy-6-methyl-1,3,3a,7-tetrazaindene, 3.2 g of Dye (a), 5.1 g of KBr, and 2,6 g of stabilizer ① were successively added, followed by cooling. In this way, 28.1 kg of a monodisperse cubic silver chlorobromide emulsion having an average grain size of 0.35 μm was obtained.

TABLE 3

| Composition | |
|---|---|
| $H_2O$ | 26300 cc |
| Lime-processed gelatin | 800 g |
| KBr | 12 g |
| NaCl | 80 g |
| Compound(a) | 1.2 g |
| Temperature | 53° C. |

TABLE 4

| | Solution (I) | Solution (II) | Solution (III) | Solution (IV) |
|---|---|---|---|---|
| $AgNO_3$ | 1200 g | none | 2800 g | none |
| KBr | none | 546 g | none | 1766 g |
| NaCl | none | 144 g | none | 96 g |
| $K_2IrCl_6$ | none | 3.6 mg | none | none |
| Total volume | water to make 6.5 liters | water to make 6.5 liters | water to make 10 liters | water to make 10 liters |

Compound (a)

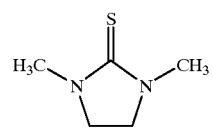

Dye (a)

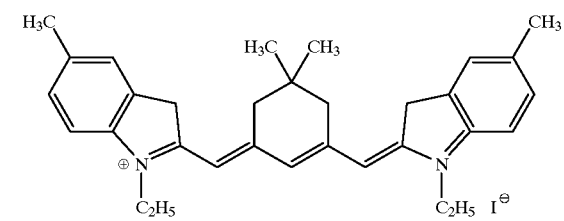

Stabilizer ①

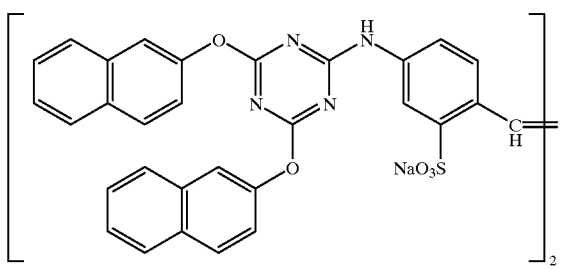

Light-Sensitive Silver Halide Emulsion (2) [for a green-sensitive emulsion layer]

Solutions (I) and (II) each having the composition shown in Table 6 were added simultaneously, to a well-stirred aqueous solution having the composition shown in Table 5, over 9 min at a constant flow rate. After 5 min, Solutions (IV) and (III) each having the composition shown in Table 6 were simultaneously added thereto, at a constant flow rate over 32 min. After the completion of the addition of Solutions (III) and (IV), 60 ml of a methanol solution of dyes (containing 360 mg of Dye (b1) and 73.4 mg of Dye (b2)) was added at a time.

After washing with water and desalting (at a pH of 4.0 using Settling Agent a) in a usual manner, 22 g of lime-processed ossein gelatin was added, the pH and the pAg were adjusted to 6.0 and 7.6 respectively, then the chemical sensitization was carried out optimally at 60° C. by adding 1.8 mg of sodium thiosulfate and 180 mg of 4-hydroxy-6-methyl-1,3,3a,7-tetrazaindene, and then 90 mg of Antifogging Agent (1) was added, followed by cooling. In this way, 635 g of a monodisperse cubic silver chlorobromide emulsion having an average grain size of 0.30 μm was obtained.

TABLE 5

| Composition | |
|---|---|
| $H_2O$ | 600 cc |
| Lime-processed gelatin | 20 g |
| KBr | 0.3 g |
| NaCl | 2 g |
| Compound(a) | 0.03 g |
| Sulfuric acid (1N) | 16 cc |
| Temperature | 46° C. |

TABLE 6

| | Solution (I) | Solution (II) | Solution (III) | Solution (IV) |
|---|---|---|---|---|
| $AgNO_3$ | 10.0 g | none | 90.0 g | none |
| KBr | none | 3.50 g | none | 57.1 g |
| NaCl | none | 1.72 g | none | 3.13 g |
| $K_2IrCl_6$ | none | none | none | 0.03 mg |

TABLE 6-continued

| | Solution (I) | Solution (II) | Solution (III) | Solution (IV) |
|---|---|---|---|---|
| Total volume | water to make 126 ml | water to make 131 ml | water to make 280 ml | water to make 289 ml |

Dye (b-1)

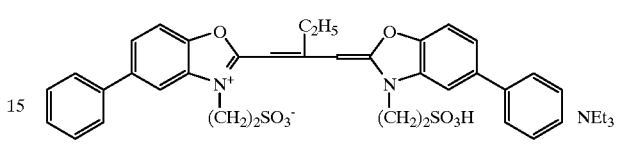

Dye (b-2)

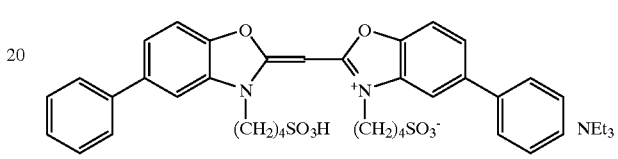

Settling agent a

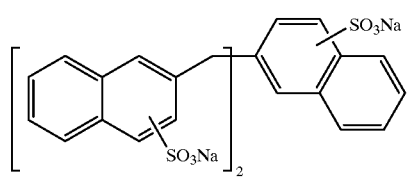

Antifoggant (1)

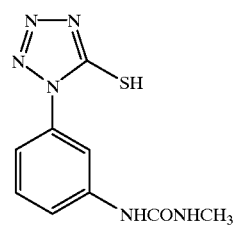

Light-Sensitive Silver Halide Emulsion (3) [for a blue-sensitive emulsion layer]

To a well-stirred aqueous solution having the composition shown in Table 7, was added Solution (II) having the composition shown in Table 8 over 30 min, and after 10 sec of the start of the addition of Solution (II) having the composition shown in Table 8 was added over 30 min. After 2 min of the completion of the adding of solution (I), Solution (V) was added, also after 5 min of the completion of the adding of Solution (II), Solution (IV) was added, and then after 10 sec, Solution (III) was added over 27 min 50 sec and Solution (IV) was added over 28 min.

Then, after washing with water and desalting (at a pH of 3.9 using Settling Agent b) in a usual manner, 1,230 g of lime-processed ossein gelatin and 2.8 mg of Compound (b) were added, and the pH and the pAg were adjusted to 6.1 and 8.4 respectively. Then, after the chemical sensitization was carried out at 60° C. for optimally by adding 24.9 mg of sodium thiosulfate, 13.1 g of Dye (c) and 118 ml of Compound (c) were added successively, followed by cooling. The silver halide grains of the resulting emulsion were potato-like grains and had an average grain size of 0.53 μm and the yield was 30,700 g.

TABLE 7

| Composition | |
|---|---|
| H$_2$O | 29200 cc |
| Lime-processed gelatin | 1582 g |
| KBr | 127 g |
| Compound(a) | 0.66 g |
| Temperature | 72° C. |

TABLE 8

| | Solution (I) | Solution (II) | Solution (III) | Solution (IV) | Solution (V) |
|---|---|---|---|---|---|
| AgNO$_3$ | 939 g | none | 3461 g | none | none |
| KBr | none | 572 g | none | 2464 g | none |
| KI | none | none | none | none | 22 g |
| Total volume | water to make 6690 ml | water to make 6680 ml | water to make 9700 ml | water to make 9740 ml | water to make 4400 ml |

Settling agent b

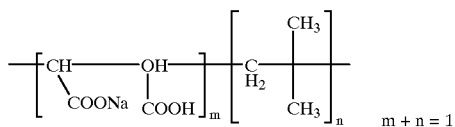

Dye (c)

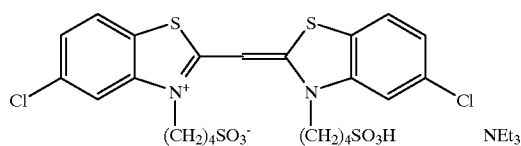

Compound (b)

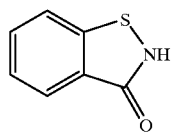

Compound (c)

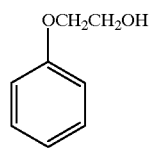

Next, the preparation methods of gelatin dispersions of hydrophobic additives are described.

A gelatin dispersion of each of a yellow coupler, a magenta coupler, and a cyan coupler, and a developing agent, whose formulation is shown in Table 9 was prepared, respectively. That is, the oil phase components were dissolved by heating to about 70° C. to form a uniform solution, and, to the resultant solution, was added the aqueous phase components that had been heated to about 60° C., followed by stirring to mix and dispersing by a homogenizer for 10 min at 10,000 rpm. To the resultant description, was added additional water, followed by stirring to obtain a uniform dispersion.

TABLE 9

| | Composition of dispersion | | |
|---|---|---|---|
| | Yellow | Magenta | Cyan |
| Oil phase | | | |
| Cyan coupler①  | none | none | 7.0 g |
| Magenta coupler①  | none | 7.0 g | none |
| Yellow coupler①  | 7.0 g | none | none |
| Developing agent①  | none | none | 5.6 g |
| Developing agent②  | none | 5.6 g | none |
| Developing agent③  | 5.6 g | none | none |
| Auxiliary developing agent①  | 0.51 g | 0.51 g | 0.51 g |
| Antifoggant⑤  | 0.25 g | none | none |
| Antifoggant②  | none | 0.25 g | 0.25 g |
| High-boiling solvent④  | 7.4 g | 7.4 g | 7.4 g |
| Ethyl acetate | 15 cc | 15 cc | 15 cc |
| Aqueous phase | | | |
| Lime-processed gelatin | 10.0 g | 10.0 g | 10.0 g |
| Calcium nitrate | 0.1 g | 0.1 g | 0.1 g |
| Surfactant①  | 0.7 g | 0.7 g | 0.7 g |
| Water | 110 cc | 110 cc | 110 cc |
| Additonal water | 110 cc | 110 cc | 110 cc |
| Antiseptic①  | 0.04 g | 0.04 g | 0.04 g |

A gelatin dispersion of Antifoggant ④ and Reducing Agent ① whose formulation is shown in Table 10 was prepared. That is, the oil phase components were dissolved by heating to about 60° C. to form a uniform solution, and, to the resultant solution, was added the aqueous phase components that had been heated to about 60° C., and after stirring and mixing them, the resultant mixture was dispersed for 10 min at 10,000 rpm by a homogenizer, to obtain a uniform dispersion.

TABLE 10

| | | Composition of dispersion |
|---|---|---|
| Oil phase | Antifoggant④  | 0.16 g |
| | Reducing agent①  | 1.3 g |
| | High-boiling solvent②  | 2.3 g |
| | High-boiling solvent⑤  | 0.2 g |
| | Surfactant①  | 0.5 g |
| | Surfactant④  | 0.5 g |
| | Ethyl acetate | 10.0 ml |
| Aqueous phase | Acid-processed gelatin | 10.0 g |
| | Antiseptic①  | 0.004 g |
| | Calcium nitrate | 0.1 g |
| | Water | 35.0 ml |
| | Additional water | 104.4 ml |

A dispersion of Polymer Latex (a) whose formulation is shown in Table 11 was prepared. That is, while a mixed solution of Polymer Latex (a), Surfactant ⑤, and water was stirred, Anionic Surfactant ⑥ was added thereto over 10 min, to obtain a uniform dispersion. The resulting dispersion was repeatedly diluted with water and concentrated using a ultrafiltration module (Ultrafiltration Module: ACV-3050, trade name, manufactured by Asahi Chemical Industry Co., Ltd.) to bring the salt concentration of the dispersion to 1/9, thereby obtaining a dispersion.

TABLE 11

|  | Composition of dispersion |
|---|---|
| Polymer Latex (a) aqueous solution (solid content 13%) | 108 ml |
| Surfactant(5) | 20 g |
| Surfactant(6) | 600 ml |
| Water | 1232 ml |

A gelatin dispersion of zinc hydroxide was prepared according to the formulation shown in Table 12. That is, after the components were mixed and dissolved, dispersing was carried out for 30 min in a mill using glass beads having an average particle diameter of 0.75 mm. Then the glass beads were separated and removed, to obtain a uniform dispersion.

TABLE 12

|  | Composition of dispersion |
|---|---|
| Zinc hydroxide | 15.9 g |
| Carboxymethyl cellulose | 0.7 g |
| Poly(sodium acrylate) | 0.07 g |
| Lime-processed gelatin | 4.2 g |
| Water | 100 ml |
| Antiseptic(2) | 0.4 g |

The preparation method of a gelatin dispersion of a matting agent that was added to the protective layer is described. A solution containing PMMA dissolved in methylene chloride was added, together with a small amount of a surfactant, to gelatin, to obtain a uniform dispersion having an average particle size of 4.3 µm.

Using the above materials, Light-Sensitive Element 101 shown in Tables 13 was prepared.

TABLE 13

Constitution of Main Materials of Light-Sensitive Element 101

| Number of layer | Name of layer | Additive | Added amount (mg/m²) |
|---|---|---|---|
| Seventh layer | Protective layer | Acid-processed gelatin | 387 |
|  |  | Matting agent (PMMA resin) | 17 |
|  |  | Surfactant(2) | 6 |
|  |  | Surfactant(3) | 20 |
|  |  | Dispersion of Polymer Latex (a) | 10 |
| Sixth layer | Intermediate layer | Lime-processed gelatin | 862 |
|  |  | Antifoggant(4) | 7 |
|  |  | Reducing agent(1) | 57 |
|  |  | High-boiling solvent(2) | 101 |
|  |  | High-boiling solvent(5) | 9 |
|  |  | Surfactant(1) | 21 |
|  |  | Surfactant(4) | 21 |
|  |  | Water-soluble polymer(1) | 5 |
|  |  | Zinc hydroxide | 558 |
|  |  | Calcium nitrate | 6 |
| Fifth layer | Blue-light-sensitive layer | Lime-processed gelatin | 587 |
|  |  | Light-sensitive silver halide emulsion(3) | 399 |
|  |  | Yellow coupler(1) | 410 |
|  |  | Color-developing agent(3) | 328 |
|  |  | Antifoggant(5) | 15 |
|  |  | High-boiling solvent(4) | 433 |
|  |  | Surfactant(1) | 12 |
|  |  | Water-soluble polymer(1) | 40 |
|  |  | Auxiliary developing agent(1) | 30 |

TABLE 13-continued

Constitution of Main Materials of Light-Sensitive Element 101

| Number of layer | Name of layer | Additive | Added amount (mg/m²) |
|---|---|---|---|
| Forth layer | Intermediate layer | Lime-processed gelatin | 862 |
|  |  | Antifoggant(4) | 7 |
|  |  | Reducing agent(1) | 57 |
|  |  | High-boiling solvent(2) | 101 |
|  |  | High-boiling solvent(5) | 9 |
|  |  | Surfactant(1) | 21 |
|  |  | Surfactant(4) | 21 |
|  |  | Water-soluble polymer(1) | 4 |
|  |  | Zinc hydroxide | 341 |
|  |  | Calcium nitrate | 8 |

TABLE 14

(continued from Table 13)
Constitution of Main Materials of Light-Sensitive Element 101

| Number of layer | Name of layer | Additive | Added amount (mg/m²) |
|---|---|---|---|
| Third layer | Green-light-sensitive layer | Lime-processed gelatin | 452 |
|  |  | Light-sensitive silver halide emulsion(2) | 234 |
|  |  | Magenta coupler(1) | 420 |
|  |  | Developing agent(2) | 336 |
|  |  | Antifoggant(2) | 15 |
|  |  | High-boiling solvent(4) | 444 |
|  |  | Surfactant(1) | 12 |
|  |  | Water-soluble polymer(1) | 10 |
|  |  | Auxiliary developing agent(1) | 30 |
| Second layer | Intermediate layer | Lime-processed gelatin | 862 |
|  |  | Antifoggant(4) | 7 |
|  |  | Reducing agent(1) | 57 |
|  |  | High-boiling solvent(2) | 101 |
|  |  | High-boiling solvent(5) | 9 |
|  |  | Surfactant(1) | 21 |
|  |  | Surfactant(4) | 21 |
|  |  | Water-soluble polymer(1) | 10 |
|  |  | Calcium nitrate | 6 |
| First layer | Red-light-sensitive layer | Lime-processed gelatin | 373 |
|  |  | Light-sensitive silver halide emulsion(1) | 160 |
|  |  | Cyan coupler(1) | 390 |
|  |  | Developing agent(1) | 312 |
|  |  | Antifoggant(2) | 14 |
|  |  | High-boiling solvent(4) | 412 |
|  |  | Surfactant(1) | 11 |
|  |  | Water-soluble polymer(2) | 25 |
|  |  | Hardener(1) | 45 |
|  |  | Auxiliary developing agent(1) | 30 |

Support (a support made by aluminum-evaporation on a PET of 20 µm and further surface-undercoating with gelatin.)

Antifoggant (5)

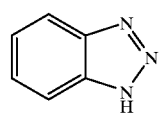

Antifoggant (2)

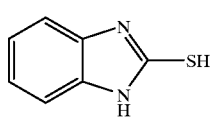

High-boiling solvent ④

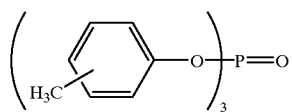

Antiseptic ①

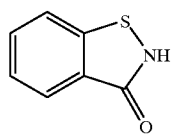

Surfactant ①

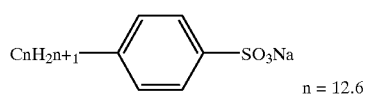

n = 12.6

Antifoggant ④

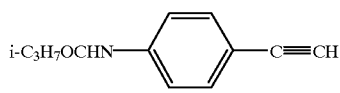

Surfactant ④

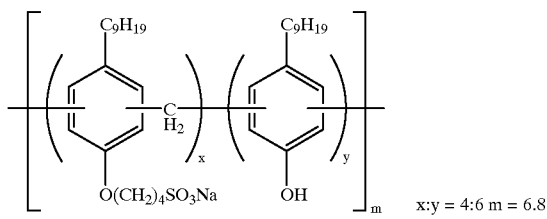

x:y = 4:6  m = 6.8

High-boiling solvent ②

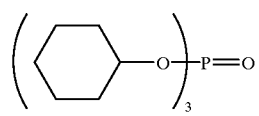

High-boiling solvent ⑤

$C_{18}H_{48.9}Cl_{7.1}$  (EMPARA 40 (trade name: manufactured by Ajinomoto K.K.))

Reducing agent ①

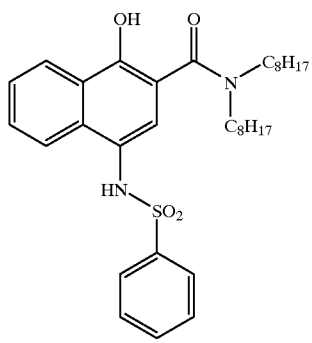

Polymer Latex (a)

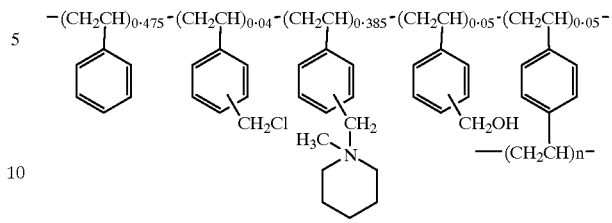

Surfactant ⑤

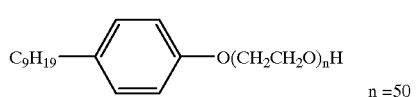

n = 50

Surfactant ⑥

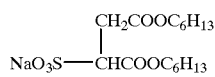

Antiseptic ②

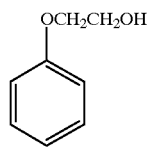

Surfactant ②

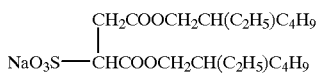

Surfactant ③

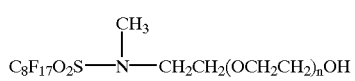

Water-soluble polymer ①

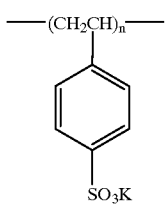

0.1N NaCl 30° C.
limitting viscosity = 1.6
molecular weight = 1,000,000

Water-soluble polymer ②

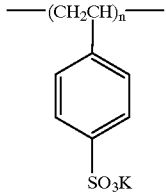

0.1N NaCl 30° C.
limitting viscosity = 0.8
molecular weight = 1,000,000

Hardener ①

-continued

Auxiliary developing agent ①

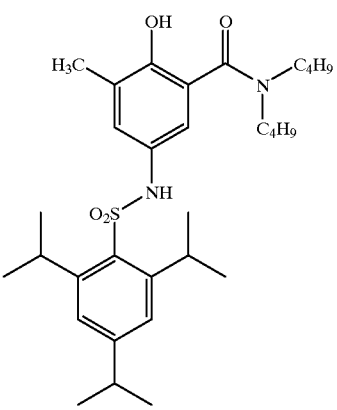

Developing agent ①

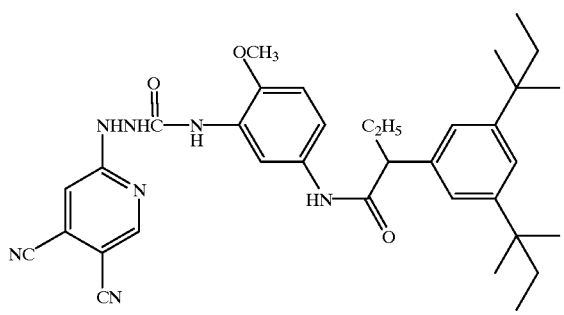

Compound (64) described in JP-A-09-152705

Developing agent ②

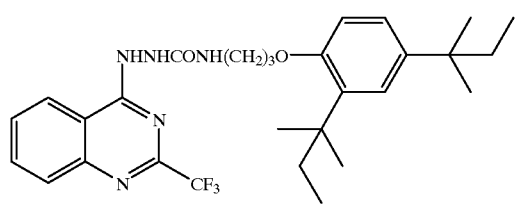

Compound (36) described in JP-A-09-152705

Developing agent ③

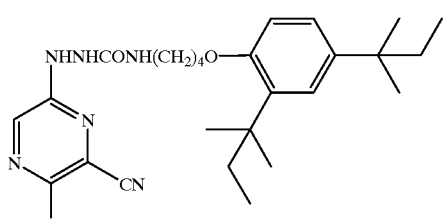

Compound (49) described in JP-A-09-152705

-continued

Yellow coupler ①

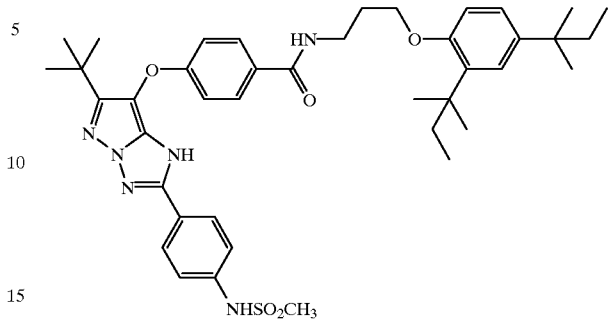

Compound (C-17) described in JP-A-09-152705

Magenta coupler ①

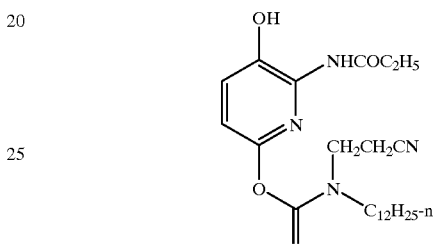

Compound (C-43) described in JP-A-09-152705

Cyan coupler ①

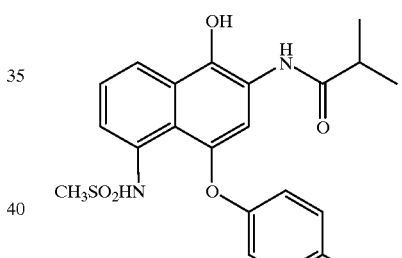

Compound (C-37) described in JP-A-09-152705

Next, light sensitive elements 103–108 were made in the same manner except that developing agents represented by the formula (1) of the present invention and couplers shown in Table 15 were used in place of the developing agent and coupler used in the first, third and fifth layers of the above light-sensitive material 101. The developing agents and couplers used here are shown in Table 15. In addition, a light-sensitive element 102 was made using compounds described in JP-A-09-152702.

Then, using each light-sensitive material and the image-receiving element R101, obtained as the above, an image was output at 83° C. for 10 seconds by a Pictrostat 330 (trade name) manufactured by Fuji Photo Film Co., Ltd.

The images output from the light-sensitive elements 103–108 were sharp (vivid) color images, indicating that the use of the compounds of the present invention ensured the provision of an image having high sharpness.

The maximum density and the minimum density, of the images thus obtained, were measured using a reflecting densitometer X-rite 304 manufactured by X-rite Co. The results are shown in Table 16.

When the compounds of the present invention were used, as is clear from Table 16, excellent color formation efficiency was obtained in a short developing time and the resulting image was stable under various conditions with respect to light, heat, humidity, and the like.

TABLE 15

| Light-sensitive material | Yellow Coupler | Yellow Developing agent | Magenta Coupler | Magenta Developing agent | Cyan Coupler | Cyan Developing agent |
|---|---|---|---|---|---|---|
| 101 | Yellow coupler ① | Developing agent ③ | Magenta coupler ① | Developing agent ② | Cyan coupler ① | Developing agent ① |
| 102 | Yellow coupler ① | a | Magenta coupler ① | a | Cyan coupler ① | a |
| 103 | Yellow coupler ① | R-1 | Magenta coupler ① | R-1 | Cyan coupler ① | R-1 |
| 104 | C-14 | R-2 | C-38 | R-2 | C-32 | R-2 |
| 105 | C-4 | R-4 | C-41 | R-1 | C-32 | R-4 |
| 106 | C-14 | R-5 | C-50 | R-1 | C-37 | R-5 |
| 107 | C-23 | R-7 | C-28 | R-16 | C-31 | R-16 |
| 108 | C-4 | R-1 | C-38 | R-1 | C-29 | R-1 |

Note) a represents a compound D-7 described in JP-A-9-152702.

TABLE 16

| Light-sensitive material | Yellow Maximum density | Yellow Minimum density | Magenta Maximum density | Magenta Minimum density | Cyan Maximum density | Cyan Minimum density | Remarks |
|---|---|---|---|---|---|---|---|
| 101 | 0.98 | 0.18 | 1.13 | 0.13 | 1.22 | 0.19 | Comparative example |
| 102 | 1.12 | 0.14 | 1.26 | 0.14 | 1.38 | 0.16 | Comparative example |
| 103 | 1.68 | 0.14 | 1.88 | 0.15 | 1.81 | 0.16 | This invention |
| 104 | 1.58 | 0.16 | 1.81 | 0.13 | 1.80 | 0.16 | This invention |
| 105 | 1.71 | 0.15 | 1.80 | 0.13 | 1.76 | 0.16 | This invention |
| 106 | 1.66 | 0.14 | 1.91 | 0.12 | 1.72 | 0.18 | This invention |
| 107 | 1.81 | 0.15 | 1.78 | 0.14 | 1.94 | 0.17 | This invention |
| 108 | 1.88 | 0.16 | 2.01 | 0.14 | 2.11 | 0.18 | This invention |

Example 2

Light-Sensitive Element 201 was prepared in the ing manner.

First, the method of preparing a light-sensitive silver halide emulsion is described. Light-Sensitive Silver Halide Emulsion (4) [For Fifth Layer (680 nm light-sensitive layer)]

To a well-stirred aqueous solution having the composition shown in Table 17, were added Solutions (I) and (I) each having the composition shown in Table 18, simultaneously over 13 min, and after 10 min, Solutions (III) and (IV) each having the composition shown in Table 18 were added over 33 min.

TABLE 17

| Composition | |
|---|---|
| $H_2O$ | 620 cc |
| Lime-processed gelatin | 20 g |
| KBr | 0.3 g |
| NaCl | 2 g |
| Silver halide solvent ① | 0.03 g |

TABLE 17-continued

| Composition | |
|---|---|
| Sulfuric acid (1N) | 16 cc |
| Temperature | 45° C. |

TABLE 18

| | Solution (I) | Solution (II) | Solution (III) | Solution (IV) |
|---|---|---|---|---|
| $AgNO_3$ | 30.0 g | none | 70.0 g | none |
| KBr | none | 13.7 g | none | 44.2 g |
| NaCl | none | 3.62 g | none | 2.4 g |
| $K_2IrCl_3$ | none | none | none | 0.039 mg |
| Total volume | water to make 126 ml | water to make 132 ml | water to make 254 ml | water to make 252 ml |

Silver halide solvent ①

$$H_3C-N \overset{S}{\underset{}{\|}} N-CH_3$$

Sensitizing dye ①

(structure with two naphthobenzothiazole groups connected by a =CH-C(C_2H_5)=CH- bridge, each N bearing (CH_2)_3SO_3^- / (CH_2)_3SO_3H, with NEt_3)

Further, after 13 min from the start of addition of solution (III), 150 cc of an aqueous solution containing 0.35% of sensitizing dye ① was added over 27 min.

After washing with water and desalting (that was carried out using Settling Agent a, at a pH of 4.1) in a usual manner, 22 g of lime-processed ossein gelatin was added, and after adjusting the pH and pAg to 6.0 and 7.9 respectively, the chemical sensitization was carried out at 60° C. The compounds used in the chemical sensitization are shown in Table 19. In this way, 630 g of a monodisperse cubic silver chlorobromide emulsion having a deviation coefficient of 10.2% and an average grain size of 0.20 μm was obtained.

Settling agent a

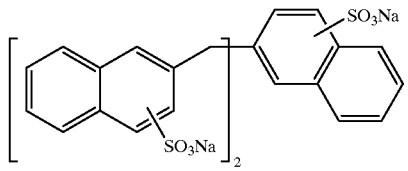

TABLE 19

| Chemicals used in chemical sensitization | Added amount |
|---|---|
| 4-hydroxy-6-methyl-1,3,3a,7-tetrazaindene | 0.36 g |
| Sodium thiosulfate | 6.75 mg |
| Antifoggant① | 0.11 g |
| Antiseptic① | 0.07 g |
| Antiseptic② | 3.31 g |

Antifoggant 1

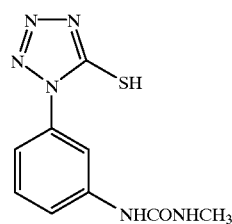

Antiseptic 1

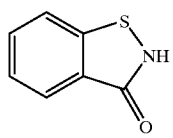

Antiseptic 2

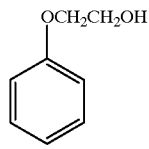

Light-Sensitive Silver Halide Emulsion (5) [For Third Layer (750-nm light-sensitive layer)]

To a well-stirred aqueous solution having the composition shown in Table 20, were added Solutions (I) and (II) each having the composition shown in Table 21, simultaneously over 18 min, and after 10 min, Solutions (III) and (IV) each having the composition shown in Table 21 were added over 24 min.

TABLE 20

| Composition | |
|---|---|
| $H_2O$ | 620 cc |
| Lime-processed gelatin | 20 g |
| KBr | 0.3 g |
| NaCl | 2 g |
| Silver halide solvent① | 0.03 g |
| Sulfuric acid (1N) | 16 cc |
| Temperature | 45° C. |

TABLE 21

| | Solution (I) | Solution (II) | Solution (III) | Solution (IV) |
|---|---|---|---|---|
| $AgNO_3$ | 30.0 g | none | 70.0 g | none |
| KBr | none | 13.7 g | none | 44.2 g |
| NaCl | none | 3.62 g | none | 2.4 g |
| $K_4[Fe(CN)_6]\cdot H_2O$ | none | none | none | 0.07 g |
| $K_2IrCl_3$ | none | none | none | 0.04 mg |
| Total volume | water to make 188 ml | water to make 188 ml | water to make 250 ml | water to make 250 ml |

After washing with water and desalting (that was carried out using Settling Agent b at a pH of 3.9) in a usual manner, 22 g of lime-processed ossein gelatin from which calcium had been removed (the calcium content: 150 ppm or less) was added, re-dispersing was made at 40° C., 0.39 g of 4-hydroxy-6-methyl-1,3,3a,7-tetrazaindene was added, and the pH and pAg were adjusted to 6.9 and 7.8 respectively. Thereafter the chemical sensitization was carried out at 70° C. using the chemicals shown in Table 22. At the end of the chemical sensitization, Sensitizing Dye ② in the form of a methanol solution (the solution having the composition shown in Table 23) was added. After the chemical sensitization, the temperature was lowered to 40° C. and then 200 g of a gelatin dispersion of the later-described Stabilizer ① was added, followed by stirring well, and in this way, 938 g of a monodisperse cubic silver chlorobromide emulsion having a deviation coefficient of 12.6% and an average grain size of 0.25 μm was obtained. In this connection, the emulsion for a 750 nm light-sensitive layer had spectral sensitivity of the J-band type.

TABLE 22

| Chemicals used in chemical sensitization | Added amount |
|---|---|
| 4-hydroxy-6-methyl-1,3,3a,7-tetrazaindene | 0.39 g |
| Triethylthiourea | 3.3 mg |
| Nucleic acid decomposition product | 0.39 g |
| NaCl | 0.15 g |
| KI | 0.12 g |
| Antifoggant② | 0.10 g |
| Antiseptic① | 0.07 g |

TABLE 23

| Composition of dye solution | Added amount |
|---|---|
| Sensitizing dye② | 0.19 g |
| Methanol | 18.7 cc |

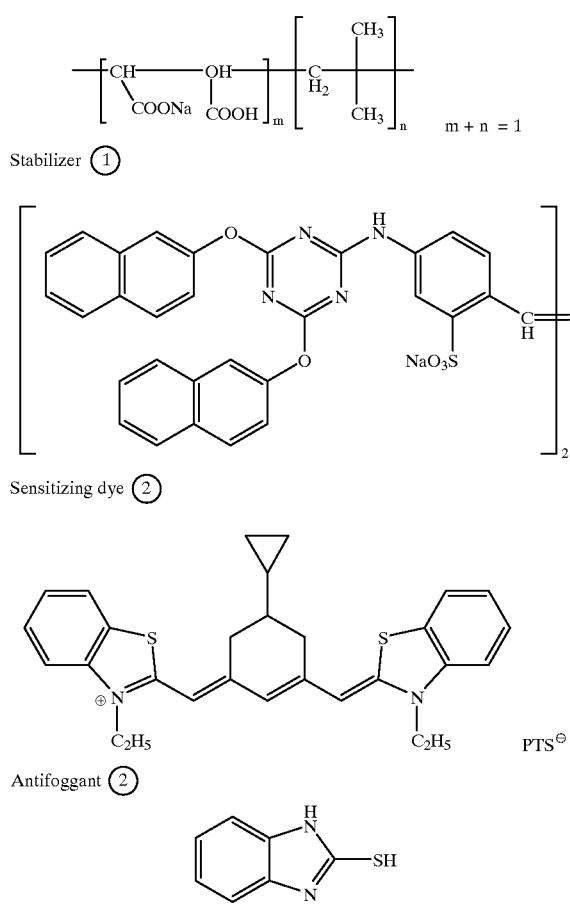

Settling agent b

Stabilizer ①

Sensitizing dye ②

Antifoggant ②

Light-Sensitive Silver Halide Emulsion (6) [For First Layer (810nm light-sensitive layer)]

To a well-stirred aqueous solution having the composition shown in Table 24, were added Solutions (I) and (II) each having the composition shown in Table 25, simultaneously over 18 min, and after 10 min, Solutions (III) and (IV) each having the composition shown in Table 25 were added over 24 min.

TABLE 24

| Composition | |
|---|---|
| H₂O | 620 cc |
| Lime-processed gelatin | 20 g |
| KBr | 0.3 g |
| NaCl | 2 g |
| Silver halide solvent① | 0.03 g |
| Sulfuric acid (1N) | 16 cc |
| Temperature | 50° C. |

TABLE 25

| | Solution (I) | Solution (II) | Solution (III) | Solution (IV) |
|---|---|---|---|---|
| AgNO₃ | 30.0 g | none | 70.0 g | none |
| KBr | none | 13.7 g | none | 44.1 g |
| NaCl | none | 3.62 g | none | 2.4 g |
| K₂IrCl₃ | none | none | none | 0.02 mg |

TABLE 25-continued

| | Solution (I) | Solution (II) | Solution (III) | Solution (IV) |
|---|---|---|---|---|
| Total volume | water to make 180 ml | water to make 181 ml | water to make 242 ml | water to make 250 ml |

After washing with water and desalting (that was carried out using Settling Agent a at a pH of 3.8) in a usual manner, 22 g of lime-processed ossein gelatin was added, and after adjusting the pH and pAg to 7.4 and 7.8 respectively, the chemical sensitization was carried out. The compounds used in the chemical sensitization are shown in Table 26. At the end of the chemical sensitization, Sensitizing Dye ③ in the form of a methanol solution (same way to Sensitizing Dye ② shown in Table 23) was added. In this way, 680 g of a monodisperse cubic silver chlorobromide emulsion having a deviation coefficient of 9.7% and an average grain size of 0.32 μm was obtained.

TABLE 26

| Chemicals used in chemical sensitization | Added amount |
|---|---|
| 4-hydroxy-6-methyl-1,3,3a,7-tetrazaindene | 0.38 g |
| Triethylthiourea | 3.1 mg |
| Antifoggant② | 0.19 g |
| Antiseptic① | 0.07 g |
| Antiseptic② | 3.13 g |

Sensitizing dye ③

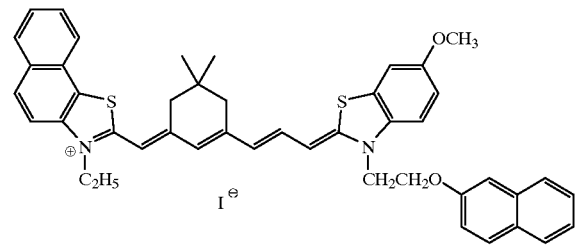

Next, the preparation method of a gelatin dispersion of colloidal silver is described.

To a well-stirred aqueous solution having the composition shown in Table 27, was added a Solution having the composition shown in Table 28, over 24 min. Thereafter, the washing with water using Settling Agent a was carried out, then 43 g of lime-processed ossein gelatin was added, and the pH was adjusted to 6.3. In this way, 512 g of a dispersion having average grain size of 0.02 μm, and containing silver 2% and gelatin 6.8% was obtained.

TABLE 27

| Composition | |
|---|---|
| H₂O | 620 cc |
| Dextrin | 16 g |
| NaOH (5N) | 41 cc |
| Temperature | 30° C. |

TABLE 28

| Composition | |
|---|---|
| H₂O | 135 cc |
| AgNO₃ | 17 g |

Next, the preparation methods of gelatin dispersions of hydrophobic additives are described.

A gelatin dispersion of each of a yellow coupler, a magenta coupler, a cyan coupler, and a color-developing agent whose formulation is shown in Table 29, was prepared, respectively. That is, the oil phase components were dissolved by heating to about 70° C., to form a uniform solution, and to the resultant solution, was added the aqueous phase components that had been heated to about 60° C., followed by stirring to mix and dispersing by a homogenizer for 10 min at 10,000 rpm. To the resultant dispersion, was added additional water, followed by stirring, to obtain a uniform dispersion.

TABLE 29

| | | Composition of dispersion | | |
|---|---|---|---|---|
| | | Yellow | Magenta | Cyan |
| Oil phase | Cyan coupler② | none | none | 7.0 g |
| | Magenta coupler② | none | 7.0 g | none |
| | Yellow coupler② | 7.0 g | none | none |
| | Developing agent④ | none | none | 5.6 g |
| | Developing agent④ | none | 5.6 g | none |
| | Developing agent④ | 5.6 g | none | none |
| | Auxiliary developing agent① | 0.51 g | 0.51 g | 0.51 g |
| | Antifoggant⑤ | 0.25 g | none | none |
| | Antifoggant② | none | 0.25 g | 0.25 g |
| | High-boiling solvent④ | 7.4 g | 7.4 g | 7.4 g |
| | Dye(a) | 1.1 g | none | 0.5 g |
| | Ethyl acetate | 15 cc | 15 cc | 15 cc |
| Aqueous phase | Lime-processed gelatin | 10.0 g | 10.0 g | 10.0 g |
| | Calcium nitrate | 0.1 g | 0.1 g | 0.1 g |
| | Surfactant① | 0.2 g | 0.2 g | 0.2 g |
| | Water | 110 cc | 110 cc | 110 cc |
| | Additional water | 110 cc | 110 cc | 110 cc |
| | Antiseptic① | 0.04 g | 0.04 g | 0.04 g |

A gelatin dispersion of Antifoggant ④ and Reducing Agent ① whose formulation is shown in Table 30 was prepared. That is, the oil phase components were dissolved by heating to about 60° C. to form a uniform solution, to the resultant solution, was added the aqueous phase components that had been heated to about 60° C., and after stirring and mixing them, the resultant mixture was dispersed for 10 min at 10,000 rpm by a homogenizer, to obtain a uniform dispersion.

TABLE 30

| | | Composition of dispersion |
|---|---|---|
| Oil phase | Antifoggant④ | 0.16 g |
| | Reducing agent① | 1.3 g |
| | High-boiling solvent② | 2.3 g |
| | High-boiling solvent⑤ | 0.2 g |
| | Surfactant① | 0.5 g |
| | Surfactant④ | 0.5 g |
| | Ethyl acetate | 10.0 ml |

TABLE 30-continued

| | | Composition of dispersion |
|---|---|---|
| Aqueous phase | Acid-processed gelatin | 10.0 g |
| | Antiseptic① | 0.004 g |
| | Calcium nitrate | 0.1 g |
| | Water | 35.0 ml |
| | Additional Water | 104.4 ml |

A gelatin dispersion of Reducing Agent ② whose formulation is shown in Table 31 was prepared. That is, the oil phase components were dissolved by heating to about 60° C. to form a uniform solution, to the resultant solution, was added the aqueous phase components that had been heated to about 60° C., and after stirring and mixing them, the resultant mixture was dispersed for 10 min at 10,000 rpm by a homogenizer, to obtain a uniform dispersion. From the thus-obtained dispersion, ethyl acetate was removed off using a vacuum organic solvent removing apparatus.

TABLE 31

| | | Composition of dispersion |
|---|---|---|
| Oil phase | Reducing agent② | 7.5 g |
| | High-boiling solvent① | 4.7 g |
| | Surfactant① | 1.9 g |
| | Ethyl acetate | 14.4 ml |
| Aqueous phase | Acid-processed gelatin | 10.0 g |
| | Antiseptic① | 0.02 g |
| | Gentamicin | 0.04 g |
| | Sodium bisulfite | 0.1 g |
| | Water | 136.7 ml |

A dispersion of Polymer Latex (a) whose formulation is shown in Table 32 was prepared. That is, while a mixed solution of Polymer Latex (a), Surfactant ⑤, and water whose amounts are shown in Table 32 was stirred, Anionic Surfactant ⑥ was added thereto, over 10 min, to obtain a uniform dispersion. The resulting dispersion was repeatedly diluted with water and concentrated using a ultrafiltration module (Ultrafiltration Module: ACV-3050, trade name, manufactured by Asahi Chemical Industry Co., Ltd.), to bring the salt concentration of the dispersion to 1/9, thereby obtaining a dispersion.

TABLE 32

| | Composition of dispersion |
|---|---|
| Polymer Latex (a) aqueous solution (solid content 13%) | 108 ml |
| Surfactant⑤ | 20 g |
| Surfactant⑥ | 600 ml |
| Water | 1232 ml |

A gelatin dispersion of Stabilizer ① whose formulation is shown in Table 33 was prepared. That is, the oil phase components were dissolved at room temperature to form a uniform solution, to the resultant solution, was added the aqueous phase components that had been heated to about 40° C., and after stirring and mixing them, the resultant mixture was dispersed for 10 min at 10,000 rpm by a homogenizer. To the resultant dispersion, was added additional water, followed by stirring, thereby obtaining a uniform dispersion.

TABLE 33

| | | Composition of dispersion |
|---|---|---|
| Oil phase | Stabilizer① | 4.0 g |
| | Sodium hydroxide | 0.3 g |
| | Methanol | 62.8 g |
| | Antiseptic② | 0.8 g |
| Aqueous phase | Gelatin from which calcium had been removed (Ca content 100 ppm or less) | 10.0 g |
| | Antiseptic① | 0.04 g |
| | Water | 320 ml |

A gelatin dispersion of zinc hydroxide was prepared according to the formulation shown in Table 34. That is, after the components were mixed and dissolved, dispersing was carried out for 30 min in a mill, using glass beads having an average particle diameter of 0.75 mm. Then the glass beads were separated and removed off, to obtain a uniform dispersion.

TABLE 34

| | Composition of dispersion |
|---|---|
| Zinc hydroxide | 15.9 g |
| Carboxymethyl cellulose | 0.7 g |
| Poly(sodium acrylate) | 0.07 g |
| Lime-processed gelatin | 4.2 g |
| Water | 100 ml |
| Antiseptic② | 0.4 g |

Next, the preparation method of a gelatin dispersion of a matting agent that was added to the protective layer is described. A solution containing PMMA dissolved in methylene chloride was added, together with a small amount of a surfactant, to gelatin, and obtained a uniform dispersion having an average particle size of 4.3 $\mu$m.

Using the above materials, Light-Sensitive Element 201 shown in Tables 35 was prepared.

TABLE 35

Constitution of Main Materials of Light-Sensitive Element 201

| Number of layer | Name of layer | Additive | Added amount (mg/m²) |
|---|---|---|---|
| Seventh layer | Protective layer | Acid-processed gelatin | 442 |
| | | Reducing agent② | 47 |
| | | High-boiling solvent① | 30 |
| | | Colloidal silver grains | 2 |
| | | Matting agent(PMMA resin) | 17 |
| | | Surfactant① | 16 |
| | | Surfactant② | 9 |
| | | Surfactant③ | 2 |
| Sixth layer | Intermediate layer | Lime-processed gelatin | 862 |
| | | Antifoggant④ | 7 |
| | | Reducing agent① | 57 |
| | | High-boiling solvent② | 101 |
| | | High-boiling solvent⑤ | 9 |
| | | Surfactant① | 21 |
| | | Surfactant④ | 21 |
| | | Dispersion of Polymer Latex a | 5 |
| | | Water-soluble polymer① | 4 |
| | | Calcium nitrate | 6 |

TABLE 35-continued

Constitution of Main Materials of Light-Sensitive Element 201

| Number of layer | Name of layer | Additive | Added amount (mg/m²) |
|---|---|---|---|
| Fifth layer | Red-light-sensitive layer | Lime-processed gelatin | 452 |
| | | Light-sensitive silver halide emulsion(4) | 301 |
| | | Magenta coupler② | 420 |
| | | Developing agent④ | 336 |
| | | Antifoggant② | 15 |
| | | High-boiling solvent④ | 444 |
| | | Surfactant① | 12 |
| | | Water-soluble polymer① | 10 |
| | | Auxiliary developing agent① | 30 |
| Forth layer | Intermediat layer | Lime-processed gelatin | 862 |
| | | Antifoggant④ | 7 |
| | | Reducing agent① | 57 |
| | | High-boiling solvent② | 101 |
| | | High-boiling solvent⑤ | 9 |
| | | Surfactant① | 21 |
| | | Surfactant④ | 21 |
| | | Dispersion of Polymer Latex a | 5 |
| | | Water-soluble polymer① | 4 |
| | | Calcium nitrate | 6 |

TABLE 36

(continued from Table 35)
Constitution of Main Materials of Light-Sensitive Element 201

| Number of layer | Name of layer | Additive | Added amount (mg/m²) |
|---|---|---|---|
| Third layer | Second infrared-light-sensitive layer | Lime-processed gelatin | 373 |
| | | Light-sensitive silver halide emulsion(5) | 106 |
| | | Cyan coupler② | 390 |
| | | Developing agent④ | 312 |
| | | Antifoggant② | 14 |
| | | High-boiling solvent④ | 412 |
| | | Surfactant① | 11 |
| | | Water-soluble polymer① | 11 |
| | | Auxiliary developing agent① | 30 |
| Second layer | Intermediate layer | Lime-processed gelatin | 862 |
| | | Antifoggant④ | 7 |
| | | Reducing agent① | 57 |
| | | High-boiling solvent② | 101 |
| | | High-boiling solvent⑤ | 9 |
| | | Surfactant① | 21 |
| | | Surfactant④ | 21 |
| | | Water-soluble polymer② | 25 |
| | | Zinc hydroxide | 750 |
| | | Calcium nitrate | 6 |
| First layer | First infrared-light-sensitive layer | Lime-processed gelatin | 587 |
| | | Light-sensitive silver halide emulsion(6) | 311 |
| | | Yellow coupler② | 410 |
| | | Developing agent④ | 328 |
| | | Antifoggant⑤ | 15 |
| | | High-boiling solvent④ | 433 |
| | | Surfactant① | 12 |
| | | Water-soluble polymer② | 40 |
| | | Hardener① | 45 |
| | | Auxiliary developing agent① | 30 |

Support(a support made by aluminum- evaporation on a PET of 20 $\mu$m and further surface-undercoating with gelatin.)

Dye (a)

[Structure: bis-indoline pentamethine cyanine dye with two 3,3-dimethyl-1-octylindoline units connected by –(CH=CH)₃–CH= chain]

Antifoggant ④ i-C₃H₇OCHN—C₆H₄—C≡CH

Antifoggant ⑤

[Structure: 1H-benzotriazole]

Reducing agent ①

[Structure: 1-hydroxy-N,N-di(octyl)-4-(phenylsulfonylamino)-2-naphthamide]

Reducing agent ②

[Structure: bis(2,5-dihydroxy-4-tert-butylphenyl)methane derivative with C₁₁H₂₃ on central methine]

Water-soluble polymer ①

—(CH₂CH)n— with para-SO₃K phenyl substituent 0.1N NaCl 30° C.
limitting viscosity = 0.8
molecular weight = 1,000,000

Water-soluble polymer ②

—(CH₂CH)n— with para-SO₃K phenyl substituent 0.1N NaCl 30° C.
limitting viscosity = 1.6
molecular weight = 1,000,000

Auxiliary developing agent ①

[Structure: 2-hydroxy-3-methyl-N,N-dibutyl-5-(2,4,6-triisopropylphenylsulfonylamino)benzamide]

surfactant ①

C₁₂H₂₅—C₆H₄—SO₃Na surfactant ②

NaO₃S—CH(COOCH(C₂H₅)C₄H₉)—CH₂COOCH(C₂H₅)C₄H₉ surfactant ③

C₈F₁₇O₂S—N(CH₃)—CH₂CH₂(OCH₂CH₂)nOH

Surfactant ④

[Structure: copolymer of 4-octylphenol units bridged by CH₂, with x:y ratio; one ring bears O(CH₂)₄SO₃Na, the other bears OH]  x:y = 4:6  m = 6.8 surfactant ⑤

C₈H₁₇—C₆H₄—O(CH₂CH₂O)n—H    n = 85 surfactant ⑥

NaO₃S—CH(COOC₆H₁₃)—CH₂COOC₆H₁₃

High-boiling solvent ①

(OH₂CHC(C₂H₅)C₄H₉)₃—P=O

High-boiling solvent ②

(cyclohexyl—O)₃P=O

High-boiling solvent (4)

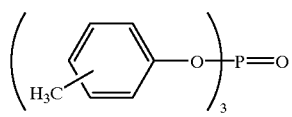

High-boiling solvent (5)

$C_{28}H_{46.9}Cl_{7.1}$  (EMPARA 40 (trade name: manufactured by Ajinomoto K.K.))

Hardener (1)

$CH_2=CHSO_2CH_2SO_2CH=CH_2$

Polymer Latex (a)

Developing agent (4)

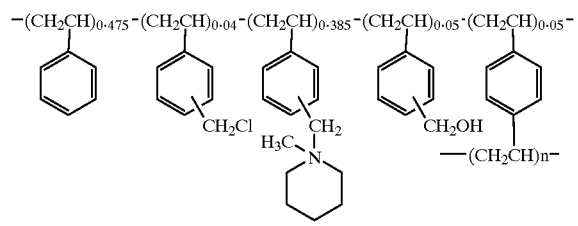

Compound (56) described in JP-A-152705

Yellow coupler (2)

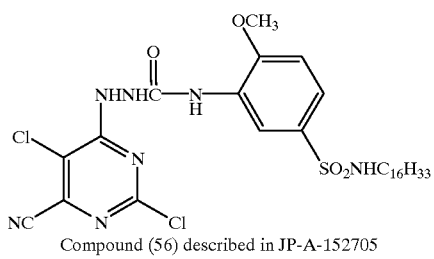

Compound (C-14) described in JP-A-09-152705

Magenta coupler (2)

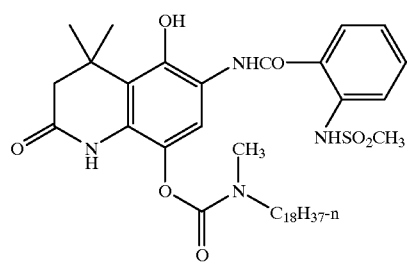

Compound (C-38) described in JP-A-09-152705

Cyan coupler (2)

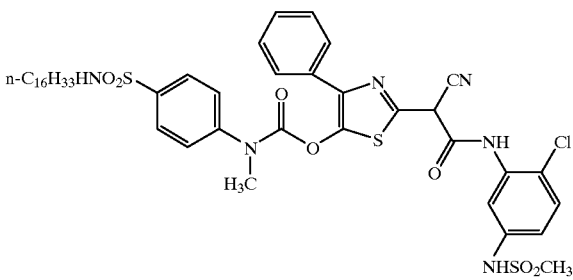

Compound (C-45) described in JP-A-09-152705

Next, light-sensitive elements 203–208 were made in the same manner except that developing agents represented by the formula (1) of the present invention and couplers shown in Table 37 were used in place of the developing agent and coupler used in the first, third and fifth layers of the above light-sensitive material 201. The developing agents and couplers used here are shown in Table 37. In addition, a light-sensitive element 202 was made using compounds described in JP-A-09-152702.

Then, using each light-sensitive material obtained as the above and the image-receiving element R101 prepared in the same manner as in Example 1, an image was output at 83° C. for 30 seconds by a PG-3000 (trade name) manufactured by Fuji Photo Film Co., Ltd.

The images output from the light-sensitive elements 203–208 were sharp(vivid) color images, indicating that the use of the compounds of the present invention ensured the provision of an image having high sharpness.

The maximum density and the minimum density, of the images thus obtained, were measured using a reflecting densitometer X-rite 304 manufactured by X-rite Co. The results are shown in Table 38.

When the compounds of the present invention were used, as is clear from Table 38, excellent color formation efficiency was obtained in a short developing time, the resulting image was stable under various conditions with respect to light, heat, humidity, and the like.

TABLE 37

| Light-sensitive material | Yellow | | Magenta | | Cyan | |
|---|---|---|---|---|---|---|
| | Coupler | Developing agent | Coupler | Developing agent | Coupler | Developing agent |
| 201 | Yellow coupler (2) | Developing agent (4) | Magenta coupler (2) | Developing agent (4) | Cyan coupler (2) | Developing agent (4) |
| 202 | Yellow coupler (2) | a* | Magenta coupler (2) | a | Cyan coupler (2) | a |
| 203 | Yellow coupler (2) | R-1 | Magenta coupler (2) | R-1 | Cyan coupler (2) | R-1 |
| 204 | C-14 | R-2 | C-38 | R-2 | C-32 | R-2 |
| 205 | C-4 | R-4 | C-41 | R-1 | C-32 | R-4 |
| 206 | C-14 | R-5 | C-50 | R-1 | C-37 | R-5 |
| 207 | C-23 | R-7 | C-28 | R-16 | C-31 | R-16 |
| 208 | C-4 | R-1 | C-38 | R-1 | C-29 | R-1 |

Note)*a is a compound D-7 described in JP-A-9-152702.

TABLE 38

| Light-sensitive material | Yellow Maximum density | Yellow Minimum density | Magenta Maximum density | Magenta Minimum density | Cyan Maximum density | Cyan Minimum density | Remarks |
|---|---|---|---|---|---|---|---|
| 201 | 1.20 | 0.16 | 1.28 | 0.14 | 1.40 | 0.16 | Comparative example |
| 202 | 1.22 | 0.14 | 1.36 | 0.14 | 1.38 | 0.15 | Comparative example |
| 203 | 1.80 | 0.14 | 1.95 | 0.14 | 1.88 | 0.15 | This invention |
| 204 | 1.78 | 0.13 | 1.96 | 0.14 | 1.89 | 0.15 | This invention |
| 205 | 1.81 | 0.16 | 1.99 | 0.13 | 1.81 | 0.16 | This invention |
| 206 | 1.80 | 0.16 | 2.01 | 0.14 | 1.95 | 0.16 | This invention |
| 207 | 2.00 | 0.15 | 1.88 | 0.16 | 2.00 | 0.16 | This invention |
| 208 | 2.08 | 0.15 | 2.11 | 0.14 | 2.14 | 0.15 | This invention |

Example 3

In the method described in Example 1 of JP-A-09-152702, the developing agents (Exemplified compounds R-1, R-2, R-5, R-11, R-15 and R-23) of the present invention were used in place of the compound example D-7 and an alkali treating solution was used to carry out developing treatment. As a consequence, images were obtained which were superior in color formation efficiency and had good storage stability, similar in the Examples 1 and 2.

Example 4

Light sensitive elements 401–406 were made in the same manner except that developing agents represented by the formula (2) of the present invention and couplers shown in Table 39 were used in place of the developing agent and coupler used in the first, third and fifth layers of the above light-sensitive material 101 used in Example 1. The developing agents and couplers used here are shown in Table 39. In addition, a light-sensitive element 102 was made using compounds described in JP-A-09-152702.

Then, using each light-sensitive material obtained as the above and the image-receiving element R101 prepared in the same manner as in Example 1, an image was output at 83° C. for 20 seconds by a Pictrostat 330 (trade name) manufactured by Fuji Photo Film Co., Ltd.

The images output from the light-sensitive elements 401–406 were sharp (vivid) color images, indicating that the use of the compounds of the present invention ensured the provision of an image having high sharpness.

The maximum density and the minimum density, of the images thus obtained, were measured using a reflecting densitometer X-rite 304 manufactured by X-rite Co. The results are shown in Table 40.

When the compounds of the present invention were used, as is clear from Table 40, excellent color formation efficiency was obtained in a short developing time and the resulting image was stable under various conditions with respect to light, heat, humidity, and the like.

TABLE 39

| Light-sensitive material | Yellow Coupler | Yellow Developing agent | Magenta Coupler | Magenta Developing agent | Cyan Coupler | Cyan Developing agent |
|---|---|---|---|---|---|---|
| 101 | Yellow coupler ① | Developing agent ③ | Magenta coupler ① | Developing agent ② | Cyan coupler ① | Developing agent ① |
| 102 | Yellow coupler ① | a* | Magenta coupler ① | a | Cyan coupler ① | a |
| 401 | Yellow coupler ① | R-101 | Magenta coupler ① | R-101 | Cyan coupler ① | R-101 |
| 402 | C-14 | R-102 | C-38 | R-102 | C-32 | R-102 |
| 403 | C-4 | R-103 | C-41 | R-101 | C-32 | R-114 |
| 404 | C-14 | R-106 | C-50 | R-111 | C-37 | R-123 |
| 405 | C-23 | R-107 | C-28 | R-111 | C-31 | R-116 |
| 406 | C-4 | R-101 | C-38 | R-101 | C-29 | R-101 |

Note)*a is a compound D-7 described in JP-A-9-152702.

TABLE 40

| Light-sensitive material | Yellow Maximum density | Yellow Minimum density | Magenta Maximum density | Magenta Minimum density | Cyan Maximum density | Cyan Minimum density | Remarks |
|---|---|---|---|---|---|---|---|
| 101 | 0.80 | 0.14 | 1.00 | 0.13 | 1.01 | 0.15 | Comparative example |
| 102 | 1.01 | 0.14 | 1.16 | 0.12 | 1.25 | 0.14 | Comparative example |
| 401 | 1.21 | 0.13 | 1.41 | 0.11 | 1.41 | 0.13 | This invention |
| 402 | 1.26 | 0.13 | 1.51 | 0.13 | 1.39 | 0.14 | This invention |
| 403 | 1.24 | 0.13 | 1.40 | 0.13 | 2.36 | 0.15 | This invention |

TABLE 40-continued

| Light-sensitive material | Yellow Maximum density | Yellow Minimum density | Magenta Maximum density | Magenta Minimum density | Cyan Maximum density | Cyan Minimum density | Remarks |
|---|---|---|---|---|---|---|---|
| 404 | 1.66 | 0.14 | 1.91 | 0.12 | 1.51 | 0.14 | This invention |
| 405 | 1.61 | 0.13 | 2.24 | 0.12 | 1.44 | 0.12 | This invention |
| 406 | 1.24 | 0.12 | 1.61 | 0.14 | 1.41 | 0.14 | This invention |

Example 5

Light sensitive elements 501–506 were made in the same manner except that developing agents represented by the formula (2) of the present. invention and couplers shown in Table 41 were used in place of the developing agent and coupler used in the first, third and fifth layers of the above light-sensitive material 201 used in Example 2. The developing agents and couplers used here are shown in Table 41. In addition, a light-sensitive element 202 was made using compounds described in JP-A-09-152702.

Then, using each light-sensitive material obtained as the above and the image-receiving element R101 prepared in the same manner as in Example 1, an image was output at 83° C. for 17 seconds by a PG-3000 (trade name) manufactured by Fuji Photo Film Co., Ltd.

The images output from the light-sensitive elements 501–506 were sharp(vivid) color images, indicating that the use of the compounds of the present invention ensured the provision of an image having high sharpness.

The maximum density and the minimum density, of the images thus obtained, were measured using a reflecting densitometer X-rite 304 manufactured by x-rite Co. The results are shown in Table 42.

When the compounds of the present invention were used, as is clear from Table 42, excellent color formation efficiency was obtained in a short developing time and the resulting image was stable under various conditions with respect to light, heat, humidity, and the like.

TABLE 41

| Light-sensitive material | Yellow Coupler | Yellow Developing agent | Magenta Coupler | Magenta Developing agent | Cyan Coupler | Cyan Developing agent |
|---|---|---|---|---|---|---|
| 201 | Yellow Coupler (2) | Developing agent (4) | Magenta coupler (2) | Developing agent (4) | Cyan coupler (2) | Developing agent (4) |
| 202 | Yellow coupler (2) | a* | Magenta coupler (2) | a | Cyan coupler (2) | a |
| 501 | Yellow coupler (2) | R-101 | Magenta coupler (2) | R-101 | Cyan coupler (2) | R-101 |
| 502 | C-14 | R-102 | C-38 | R-102 | C-32 | R-102 |
| 503 | C-4 | R-103 | C-41 | R-101 | C-32 | R-114 |
| 504 | C-14 | R-106 | C-50 | R-111 | C-37 | R-123 |
| 505 | C-23 | R-107 | C-28 | R-111 | C-31 | R-116 |
| 506 | C-4 | R-101 | C-38 | R-101 | C-29 | R-101 |

Note)*a is a compound D-7 described in JP-A-9-152702.

TABLE 42

| Light-sensitive material | Yellow Maximum density | Yellow Minimum density | Magenta Maximum density | Magenta Minimum density | Cyan Maximum density | Cyan Minimum density | Remarks |
|---|---|---|---|---|---|---|---|
| 201 | 0.91 | 0.14 | 1.14 | 0.13 | 1.14 | 0.15 | Comparative example |
| 202 | 1.13 | 0.14 | 1.25 | 0.12 | 1.36 | 0.14 | Comparative example |
| 501 | 1.31 | 0.13 | 1.64 | 0.14 | 1.61 | 0.12 | This invention |
| 502 | 1.33 | 0.12 | 1.81 | 0.13 | 1.62 | 0.13 | This invention |
| 503 | 1.30 | 0.13 | 1.63 | 0.13 | 2.55 | 0.15 | This invention |
| 504 | 1.71 | 0.14 | 2.11 | 0.12 | 1.81 | 0.14 | This invention |
| 505 | 1.88 | 0.13 | 2.38 | 0.12 | 1.64 | 0.12 | This invention |
| 506 | 1.41 | 0.12 | 1.84 | 0.14 | 1.49 | 0.14 | This invention |

Example 6

In the method described in Example 1 of JP-A-09-152702, the developing agents (Exemplified compounds R-101, R-102, R-106, R-107, R-111 and R-114) of the present invention were used in place of the compound example D-7 and an alkali treating solution was used to carry out developing treatment. As a consequence, images were obtained which were superior in color formation efficiency and had good storage stability, similar in the Examples 4 and 5.

Example 7

As shown in Table 43, light sensitive elements 701 to 707 were made in the same manner except that developing agents and couplers represented by the formula (3) and (4) as defined in the present invention were used in place of the developing agent and coupler used in the third layer of the above light-sensitive material 101 used in Example 1.

Then, using each light-sensitive material obtained as the above and the image-receiving element R101 prepared in the same manner as in Example 1, an image was output at 80° C. for 20 seconds by a Pictrostat 330 (trade name) manufactured by Fuji Photo Film Co., Ltd.

The images output from the light-sensitive elements 701–707 were sharp(vivid) color images, indicating that the use of the compounds as defined in the present invention ensured the provision of an image having high sharpness.

The magenta maximum density and magenta minimum density, of the images thus obtained, were measured using a reflecting densitometer X-rite 304 manufactured by X-rite Co. The results are shown in Table 43.

When the compounds as defined in the present invention were used, as is clear from Table 43, excellent color formation efficiency was obtained in a short developing time and the resulting image was stable under various conditions with respect to light, heat, humidity and the like.

TABLE 43

| Light-sensitive material | Developing agent for magenta color | Coupler for magenta color | Maximum density | Minimum density | Remarks |
|---|---|---|---|---|---|
| 101 | Developing agent② | Magenta coupler ① | 1.21 | 0.13 | Comparative example |
| 701 | R-201 | MC-1 | 1.75 | 0.12 | This invention |
| 702 | R-201 | MC-2 | 1.81 | 0.12 | This invention |
| 703 | R-201 | MC-16 | 2.00 | 0.13 | This invention |
| 704 | R-202 | MC-1 | 1.55 | 0.10 | This invention |
| 705 | R-202 | MC-2 | 1.51 | 0.11 | This invention |
| 706 | R-212 | MC-4 | 1.88 | 0.13 | This invention |
| 707 | R-213 | MC-17 | 1.65 | 0.11 | This invention |

Example 8

As shown in Table 44, light sensitive elements 801 to 807 were made in the same manner except that developing agents and couplers represented by the formula (3) and (4) as defined in the present invention were used in place of the developing agent and coupler used in the fifth layer of the above light-sensitive material 201 used in Example 2.

Then, using thus obtained each light-sensitive material obtained as the above and the image-receiving element R101 prepared in the same manner as in Example 1, an image was output at 83° C. for 30 seconds by a PG-3000 (trade name) manufactured by Fuji Photo Film Co., Ltd.

The images output from the light-sensitive elements 801–807 were sharp(vivid) color images, indicating that the use of the compounds of the present invention ensured the provision of an image having high sharpness.

The magenta maximum density and magenta minimum density, of the images thus obtained, were measured using a reflecting densitometer X-rite 304 manufactured by X-rite Co. The results are shown in Table 44.

When the compounds defined in the present invention were used, as is clear from Table 44, excellent color formation efficiency was obtained in a short developing time and the resulting image was stable under various conditions with respect to light, heat, humidity, and the like.

TABLE 44

| Light-sensitive material | Developing agent for magenta color | Coupler for magenta color | Maximum density | Minimum density | Remarks |
|---|---|---|---|---|---|
| 201 | Developing agent④ | Magenta coupler ② | 1.30 | 0.14 | Comparative example |
| 801 | R-201 | MC-1 | 1.80 | 0.12 | This invention |
| 802 | R-201 | MC-2 | 1.85 | 0.13 | This invention |
| 803 | R-201 | MC-16 | 1.95 | 0.10 | This invention |
| 804 | R-202 | MC-1 | 1.52 | 0.10 | This invention |
| 805 | R-202 | MC-2 | 1.46 | 0.11 | This invention |
| 806 | R-212 | MC-4 | 1.89 | 0.13 | This invention |
| 807 | R-213 | MC-17 | 1.62 | 0.12 | This invention |

Example 9

The developing agents (Exemplified compounds R-201, R-202, R-205, R-211, R-215 and R-223) and couplers (Exemplified compounds MC-1, MC-2, MC-4, MC-8, MC-11 and MC-16) which are defined in the present invention, were used in place of the compound example D-7 and ExM of the sample 202 according to the method described in an Example 1 of P-A-9-152702, and developing treatment was carried out using an alkali solution, to obtain a excellent image.

Having described our invention as related to the present embodiments, it is our intention that the invention not be limited by any of the details of the description, unless otherwise specified, but rather be construed broadly within its spirit and scope as set out in the accompanying claims.

What we claim is:

1. A color-developing agent represented by the following formula (1):

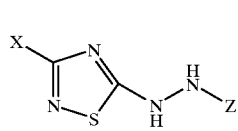

formula (1)

wherein X represents a substituent that has, as a substituent on the substituent, at least one substituent represented by —COOH, —NHSO$_2$R, —SO$_2$NHR, —SO$_2$NHCOR, —CONHSO$_2$R, in which R represents an alkyl group, an aryl group or an aromatic heterocyclic group, each of which may be substituted, and Z represents a carbamoyl group.

2. The color-developing agent as claimed in claim 1, wherein Z in the formula (1) is a carbamoyl group, which is a carbamoyl group having one or more hydrogen atoms bonded on the nitrogen atom of the carbamoyl group.

3. A color-developing agent represented by the following formula (2):

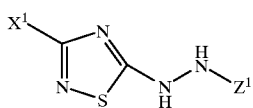

formula (2)

wherein $X^1$ represents a halogen atom, an alkylthio group, an alkylsulfonyl group, an arylthio group, an arylsulfonyl group or a sulfamoyl group, provided that a further substituent which can be substituted on $X^1$ excludes a hydroxy group, a carboxyl group, a mercapto group, an aminosulfonyl group, a carbonylaminosulfonyl group, a sulfonylamino group and a sulfonylaminocarbonyl group, $Z^1$ represents a carbamoyl group.

4. The color-developing agent as claimed in claim 3, wherein $Z^1$ in the formula (2) is a carbamoyl group, which is a carbamoyl group having one or more hydrogen atoms bonded on the nitrogen atom of the carbamoyl group.

* * * * *